US012674183B2

(12) United States Patent
Pinto Da Silva Matos et al.

(10) Patent No.: US 12,674,183 B2
(45) Date of Patent: Jul. 7, 2026

(54) PROCESS FOR THE RECOVERY OF LOW-BOILING POINT COMPONENTS FROM AN ETHANOL STREAM

(71) Applicant: Braskem S.A., Sao Paulo (BR)

(72) Inventors: Renata Pinto Da Silva Matos, Sao Paulo (BR); Thiago Bezerra Taketa, Sao Paulo (BR); Felipe Galzerani, Paulínia (BR); Adler Gomes Moura, Sao Paulo (BR)

(73) Assignee: Braskem S.A., Sao Paulo (BR)

( * ) Notice: Subject to any disclaimer, the term of this patent is extended or adjusted under 35 U.S.C. 154(b) by 371 days.

(21) Appl. No.: 18/237,170

(22) Filed: Aug. 23, 2023

(65) Prior Publication Data

US 2024/0067994 A1 Feb. 29, 2024

Related U.S. Application Data

(60) Provisional application No. 63/400,535, filed on Aug. 24, 2022.

(51) Int. Cl.

| | |
|---|---|
| *C12P 7/04* | (2006.01) |
| *B01D 3/34* | (2006.01) |
| *B01D 3/40* | (2006.01) |
| *C07C 29/80* | (2006.01) |
| *C07C 45/82* | (2006.01) |
| *C12P 7/28* | (2006.01) |

(52) U.S. Cl.
CPC ................ *C12P 7/04* (2013.01); *B01D 3/343* (2013.01); *B01D 3/40* (2013.01); *C07C 29/80* (2013.01); *C07C 45/82* (2013.01); *C12P 7/28* (2013.01)

(58) Field of Classification Search
CPC ... C12P 7/04; C12P 7/28; B01D 3/343; B01D 3/40; B01D 3/143; C07C 29/80; C07C 45/82; C07C 45/786; C07C 49/08; C07C 31/10
See application file for complete search history.

(56) References Cited

U.S. PATENT DOCUMENTS

| | | | |
|---|---|---|---|
| 9,957,530 B2 | 5/2018 | Mcbride et al. | |
| 10,150,974 B2 | 12/2018 | Green et al. | |
| 10,427,994 B2 * | 10/2019 | Thirasak | .................. B01D 3/40 |

(Continued)

FOREIGN PATENT DOCUMENTS

| | | | | |
|---|---|---|---|---|
| JP | H0763561 B2 * | 7/1995 | ................ | C12F 1/02 |
| WO | 2021163780 A1 | 8/2021 | | |

OTHER PUBLICATIONS

English machine translation of JP 7-63561 (Year: 1995).*

(Continued)

*Primary Examiner* — Renee Robinson
(74) *Attorney, Agent, or Firm* — Morgan, Lewis & Bockius LLP

(57) ABSTRACT

The disclosure provides a process for the production of ethanol and one or more low boiling compound from a fermentable carbon source. The ethanol and the low boiling compound(s) are produced using an ethanol-producing yeast modified to further produce the one or more low boiling point compounds. In one embodiment, the low boiling compound(s) are acetone, 1-propanol, and/or 2-propanol. Additionally, the disclosure provides a process for the isolation ad purification of the one or more low boiling compounds from ethanol.

20 Claims, 7 Drawing Sheets

(56) References Cited

U.S. PATENT DOCUMENTS

| | | | |
|---|---|---|---|
| 10,729,987 | B1 | 8/2020 | Andrade et al. |
| 10,961,489 | B2 | 3/2021 | Coupard et al. |
| 2010/0196979 | A1 | 8/2010 | Birkmire et al. |
| 2012/0252083 | A1* | 10/2012 | Koepke .................. C12N 15/74 |
| | | | 435/150 |
| 2013/0280775 | A1 | 10/2013 | Grotkjaer et al. |
| 2014/0377820 | A1 | 12/2014 | Pharkya et al. |
| 2018/0179558 | A1 | 6/2018 | Koch et al. |
| 2020/0216864 | A1 | 7/2020 | Magalhaes et al. |
| 2021/0261987 | A1* | 8/2021 | Galzerani ................. C12P 7/40 |
| 2021/0284592 | A1* | 9/2021 | Gillespie ............... B01D 3/002 |

OTHER PUBLICATIONS

Iulian Patraşcu et al., Eco-efficient butanol separation in the ABE fermentation process, Separation and Purification Technology, Apr. 28, 2017, vol. 177, pp. 49-61 (13 pages). doi.org/10.1016/j.seppur. 2016.12.008.

Hamid Amiri et al., Recent innovations for reviving the ABE fermentation for production of butanol as a drop-in liquid biofuel, Biofuel Research Journal, Dec. 2020, vol. 7, Issue 4, pp. 1256-1266 (11 pages). doi.org/10.18331/BRJ2020.7.4.4.

Swarnalatha Mailaram et al., Dual liquid-liquid extraction versus distillation for the production of bio-butanol from corn, sugarcane, and lignocellulose biomass: A techno-economic analysis using pinch technology, Fuel, Mar. 2022, vol. 312, 122932 (11 pages). doi.org/10.1016/j.fuel.2021.122932.

International Search Report and Written Opinion issued in corresponding International Patent Application No. PCT/BR2023/ 050277 dated Dec. 15, 2023.

Pauli Kallio et al., An engineered pathway for the biosynthesis of renewable propane, Nature Communications, Sep. 2, 2014, vol. 5, Article No. 4731 (8 pages). DOI: 10.1038/ncomms5731.

* cited by examiner

PROCESS FOR THE RECOVERY OF LOW-BOILING POINT COMPONENTS FROM AN ETHANOL STREAM

CROSS-REFERENCE TO RELATED APPLICATIONS

The present application claims priority to U.S. Provisional Patent Application No. 63/400,535, filed Aug. 24, 2022, which is incorporated by reference herein in its entirety.

BACKGROUND

The bio-based production of acetone and 2-propanol (i.e. isopropanol) from microbial sugar fermentation processes are well-known. In a typical process, *Clostridium* bacteria produce acetone and isopropanol alongside the major product, butanol, in a mixture with ethanol in a system referred to as an ABE (acetone-butanol-ethanol) or an IBE (isopropanol-butanol-ethanol) fermentation system. The ABE fermentation process was first commercialized in the UK in 1916 and spread out around the globe during the first and second world wars, mainly to produce acetone for munitions and butanol for paint lacquers. In the 1950s, with the advent of new petrochemical processes and low-cost crude oil, the ABE fermentation processes became economically unattractive and most of the commercial installations were shut down. None of the processes used to replace the ABE or IBE process can be applied to recover the low boiling point components in an energy efficient downstream process.

Due to the increase in oil price and concerns associated with the petroleum supply as well as climate change, the energy transition to more sustainable feedstocks is fostering the development and industrialization of technologies based on renewable materials, and the re-commercialization of the ABE fermentation system. However, despite of the many efforts to optimize the ABE fermentation system over the past decades, there is still a lack in terms of technology efficiency and cost-competitiveness of the bio-based acetone and butanol compared to their fossil-counterparties. Therefore, further improvements are needed to reach the commercial performance targets for economic viability. As described U.S. Pat. No. 10,150,974, the final total solvent titers from a typical ABE batch fermentation process are relatively low (18 g/L solvents in 72 hours) in comparison with industrial ethanol fermentation processes (for example >120 g/L ethanol in 48-60 hours for the industrial corn-ethanol), and this results in low volumetric productivities (0.25 g/L·h from ABE fermentation versus >2 g/L·h from ethanol fermentation). This is still a key technical drawback that needs to be somehow solved, which is in part caused by the presence of butanol as the main target product due to its toxicity effect to *Clostridium* cells at high concentrations. Additionally, the ABE fermentation processes have a higher downstream complexity because the low-boiling acetone and high-boiling butanol must be separated from ethanol.

The most common method to produce petrochemical acetone is directly or indirectly from propylene. More than 80% of global petrochemical acetone is produced via the cumene process, and as a result, the production of acetone is tied to the production of phenol. In the petrochemical production of acetone via the cumene process, benzene is alkylated with propylene producing cumene, which is further oxidized by air to produce phenol and acetone. Therefore, the petrochemical acetone has traces of the phenol, which is an undesirable product due to its toxicity effect to human beings and to the environment.

There remains a need to develop and deliver process to produce bio-based and environmentally safer chemicals of industrial relevance. The traditional downstream configuration of an ethanol producing mill is, however, inadequate to separate the low-boiling point compound(s) produce and mainly separate the low-boiling point compound(s) such as acetone, 2-propanol, and 1-propanol. Therefore, there exists a need in the art for improved methods of producing ethanol with one or more low boiling compounds from a single feedstock by the same microorganism. There is also a need in the art for improved methods of isolating the ethanol and low boiling compounds(s).

SUMMARY

In one aspect, the present disclosure provides a process for the isolation of one or more low boiling compounds from a fermentation broth and a fermentation off-gas, the process comprising: (a) flowing a fermentation off-gas coming from one or more fermenters through a product recovery unit wherein the flow of the off-gas is counter to a solvent flowing through the product recovery unit and obtaining a solvent stream comprising the one or more low boiling compounds and ethanol; (b) mixing the solvent stream of (a) with the fermentation broth and passing the resulting fermentation mixture through a first separation unit to form a high water content stream, comprising ethanol and the one or more low boiling compounds; (c) passing the high water content stream of (b) through a second separation unit to form an intermediate water content stream, comprising ethanol and the one or more low boiling compounds; (d) passing the ethanol intermediate water content stream of (c) through a dewatering unit to form a low water content stream; and (e) passing the low water content stream of (d) through one or more operational units, separating the ethanol and the one or more low boiling compounds. In one embodiment, the fermentation broth and fermentation off-gas comprise water, the one or more low boiling compounds, ethanol, and one or more contaminants. In one embodiment, the fermentation broth comprises between about 5 g/L and about 30 g/L, more preferably about 10 g/L to 20 g/L, of the one or more low boiling compounds and between about 40 g/L and about 140 g/L ethanol. In one embodiment, the fermentation off-gas of (a) comprises one or more incondensable gases, water, ethanol, and the one or more low boiling compounds. In one embodiment, the fermentation off-gas of (a) comprises about 80% w/w to about 98%, preferentially about 92% w/w to about 98% w/w, of an incondensable gas and about 0.5% w/w to about 15%, preferentially about 2% w/w to about 5% w/w, of the one or more low boiling compounds and ethanol. In one embodiment, the incondensable gas is primarily carbon dioxide. In one embodiment, the product recovery unit of (a) is an absorption column or a scrubber column. In one embodiment, the solvent of (a) is water at a temperature of about 5° C. to about 45° C., more preferably of about 15° C. to about 35° C. In one embodiment, the fermentation mixture of (b) is stored in a tank that is integrated with a stillage heat exchanger and the stillage heat exchanger preheats the fermentation mixture before it is passed through the first separation unit. In one embodiment, the first separation unit is an evaporator, a distillation column, a set of distillation columns, or a combination of a centrifuge and a distillation column. In one embodiment, the first separation unit removes an output stream comprising water, heavy components, and solids to a stillage tank. In one embodiment, the process further comprises recycling a gas stream output from the first separation unit by passing the gas stream output through steps (a) and (b). In one embodiment, the gas stream output comprises an incondensable gas which is removed as the gas stream is passed through steps (a) and (b) and wherein the gas stream further comprises the one or more low boiling compounds and ethanol which are recovered. In one embodiment, the gas stream output comprises about 20% w/w to about 95% w/w, preferentially about 40% w/w to about 85% w/w, of an incondensable gas and about 1% w/w to about 75% w/w, preferentially about 15% w/w to about 60% w/w, of the one or more low boiling compounds and ethanol. In one embodiment, the second separation unit of (c) is a rectifier column, a distillation column, or a set of distillation columns. In one embodiment, the second separation unit of (c) removes a bottom output stream comprising primarily water and a side output stream comprising fusel oil. In one embodiment, the process further comprises: recycling the bottom output stream of (c) to an upstream fermentation process which produces the fermentation broth; recycling the bottom output stream of (c) by passing the bottom output stream through step (c); or recycling the bottom output stream of (c) by passing the bottom output stream through steps (b) and (c). In one embodiment, the intermediate water content stream of (c) comprises ethanol, water, and the one or more low boiling compounds. In one embodiment, the intermediate water content stream of (c) comprises one or more high boiling compounds, in negligible amounts, that were present in the fermentation broth or a raw material from which the fermentation broth is obtained. In one embodiment, the intermediate water content stream of (c) comprises about 75% w/w to about 95% w/w ethanol, about 5% w/w to about 10% w/w water, and about 1% w/w to about 15% w/w of the one or more low boiling compounds. In one embodiment, the process further comprises removing a top vapor stream from the second separation unit of (c) and recycling the top vapor stream by combining the top vapor stream with the fermentation off-gas and passing the combined stream through steps (a), (b), and (c). In one embodiment, the dewatering unit of (d) is a membrane separation system or a molecular sieve system. In one embodiment, the low water content stream of (d) comprises less than about 2.5% w/w water or between about 0.5% w/w to about 2.5% w/w water. In one embodiment, the process further comprises recycling water removed by the dewatering unit of (d) by passing the removed water through steps (c) and (d). In one embodiment, the process further comprises removing a top vapor stream from the dewatering unit of (d) and recycling the top vapor stream by combining the top vapor stream with the fermentation off-gas and passing the combined stream through steps (a), (b), (c), and (d). In one embodiment, the one or more low boiling compounds are selected from a C3 alcohol, a C3 ketone, or a combination thereof. In one embodiment, the one or more low boiling compounds are selected from 1-propanol, 2-propanol, acetone, or a combination thereof. In one embodiment, the fermentation broth comprises C4 alcohols at a negligible amount compared to the amount of ethanol and the one or more low boiling compounds such that the amount of C4 alcohols does not justify their purification as target products. In one embodiment, the C4 alcohol is 1-butanol, 2-butanol, or a combination thereof.

In one embodiment, the low boiling compound is acetone and the one or more operational units of (e) is a pervaporation system, a single distillation column, a sequence of distillation columns, a vacuum column, or a combination thereof, which separates the ethanol from the acetone. In one embodiment, the pervaporation system, the single distillation column, the sequence of distillation columns, the vacuum column, or the combination thereof of (e) each independently optionally comprise a heat exchanger or a reboiler that can be heat integrated with the second separation unit of (c) or with any other process unit that has proper heat available. In one embodiment, the one or more operational units of (e) further separate a contaminant stream. In one embodiment, the contaminant stream comprises acetaldehyde and acetone. In one embodiment, the process further comprises combining the contaminant stream with one or more side streams from steps (b), (c), and/or (d), wherein the one or more side streams comprise contaminants, ethanol, and/or acetone. In one embodiment, the process further comprises passing the combined stream through an adsorption column to recover the ethanol and/or the acetone. In one embodiment, the process further comprises passing the recovered acetone and/or ethanol through steps (b), (c), (d), and (e) to purify the recovered acetone and/or ethanol to a desired purity.

In one embodiment, the low boiling compounds are acetone and 1-propanol and the one or more operational units of (e) are: (i) a first distillation system which separates 1-propanol from a mixture comprising ethanol and acetone, (ii) a second distillation system which purifies the 1-propanol from (i) to a desired purity, and (iii) a third distillation system which separates the mixture of (i) into ethanol and acetone to a desired purity. In one embodiment, the distillation systems (i) and (iii) each independently optionally comprise a reboiler that can be heat integrated with the second separation unit of (c) or with any other process unit that has proper heat available. In one embodiment, the acetone separated in distillation system (iii) comprises one or more contaminants and the one or more operational units of (e) further comprise (iv) a fourth distillation system which separates the acetone from the one or more contaminants. In one embodiment, the one or more contaminants comprise acetaldehyde. In one embodiment, the one or more contaminants further comprise one or more desired products selected from ethanol and acetone, and the process further comprises passing the one or more contaminants through steps (a), (b), (c), (d), and (e) to obtain the one or more desired products. In one embodiment, the one or more contaminants further comprise one or more desired products selected from ethanol, acetone, and 1-propanol and the process further comprises feeding the one or more contaminants into a scrubber and recovering the one or more desired products by adsorption with a solvent. In one embodiment, the one or more contaminants are also adsorbed by the solvent and the process further comprises passing the solvent through steps (b), (c), (d), and (e) to obtain the one or more desired products. In one embodiment, the process further comprises feeding one or more vapor streams from steps (a), (d), or (e) into the scrubber.

In one embodiment, the low boiling compounds are 1-propanol and 2-propanol and the one or more operational units of (e) are: (i) one or more distillation columns which separate 1-propanol from a mixture comprising ethanol and 2-propanol, (ii) an extractive distillation unit which uses a solvent to extract 2-propanol from a vapor phase mixture comprising ethanol and 2-propanol while obtaining a first fraction of ethanol at a desired purity and a second fraction comprising solvent, 2-propanol, and ethanol, (iii) one or more distillation columns which separate the second fraction of (ii) into solvent and a mixture of ethanol and 2-propanol, and (iv) one or more distillation columns which separate 2-propanol at a desired purity from the mixture of (iii), leaving a solution of primarily ethanol with 2-propanol, wherein the operational units (ii) to (iv) can be replaced with a system comprising two distillation columns operating under vacuum conditions. In one embodiment, the process further comprises recycling the solvent of (iii) for use in the extractive distillation unit of (ii). In one embodiment, the process further comprises: recycling the solution of (iv) by heating the solution to form a vapor and passing the vapor through the extractive distillation unit of (ii); or recycling the solution of (iv) by passing the solution through the extractive distillation unit of (ii). In one embodiment, distillation columns (i) and (iv) each independently optionally comprise a reboiler that can be heat integrated with the second separation unit of (c), the extractive distillation unit of (ii), a combination thereof, or with any other process unit that has proper heat available; or operational units (ii), (iii), and (iv) are replaced by two distillation columns operating under vacuum conditions which each independently optionally comprise a reboiler that can be heat integrated with a condenser of (c), a condenser of (i), or a combination thereof.

In one embodiment, the low boiling compound is 2-propanol and the one or more operational units of (e) comprise: (i) an extractive distillation unit which uses a solvent to extract 2-propanol from a vapor phase mixture comprising ethanol and 2-propanol while obtaining a first fraction of ethanol at a desired purity and a second fraction comprising solvent, 2-propanol, and ethanol, (ii) one or more distillation columns which separate the second fraction of (i) into solvent and a mixture of ethanol and 2-propanol, and (iii) one or more distillation columns which separate 2-propanol at a desired purity from the mixture of (ii), leaving a solution of primarily ethanol with 2-propanol, wherein the operational units (i) to (iii) can be replaced with a system comprising two distillation columns operating under vacuum conditions. In one embodiment, the process further comprises recycling the solvent of (ii) for use in the extractive distillation unit of (i). In one embodiment, the process further comprises: recycling the solution of (iii) by heating the solution to form a vapor and passing the vapor through the extractive distillation unit of (i); or recycling the solution of (iii) by passing the solution through the extractive distillation unit of (i). In one embodiment, distillation column (iii) comprises a reboiler that is optionally heat integrated with the extractive distillation unit of (i) or with any other process unit that has proper heat available; or operational units (i), (ii), and (iii) are replaced by two distillation columns under vacuum conditions which each independently optionally comprise a reboiler that can be heat integrated with a condenser of (c).

In one embodiment, the fermentation broth is obtained by a process comprising: contacting a fermentable carbon source with an ethanol-producing yeast in a fermentation medium; and fermenting the carbon source by the yeast in the fermentation medium, to produce a fermentation broth and a fermentation off-gas comprising ethanol and the one or more low boiling compounds. In one embodiment, ethanol is produced at a greater concentration in mg/mL than the one or more low boiling compounds. In one embodiment, the carbon source is a C5 sugar, a C6 sugar, or a C12 sugar. In one embodiment, the carbon source is derived from a renewable source used in an ethanol mill. In one embodiment, the carbon source is derived from sugarcane, corn, cellulose, beets, biomass, or biomass waste. In one embodiment, the ethanol-producing yeast is a genetically modified *Saccharomyces cerevisiae*. In one embodiment, the ethanol-producing yeast produces greater than about 40 g/L, about 60 g/L, about 80 g/L, about 100 g/L, about 120 g/L, about 140 g/L of ethanol after fermentation for less than about 72 hours, about 60 hours, about 55 hours, about 50 hours, about 10 hours, or about 5 hours at an industrial scale. In one embodiment, the ethanol-producing yeast produces greater than about 1 g/L, about 3 g/L, about 5 g/L, about 10 g/L, about 15 g/L or about 30 g/L of the one or more low boiling compounds after fermentation for less than about 72 hours, about 60 hours, about 55 hours, about 50 hours, about 10 hours, or about 5 at an industrial scale. In one embodiment, the ethanol-producing yeast produces greater than about 1 g/L, about 3 g/L, about 5 g/L, about 10 g/L, about 15 g/L or about 30 g/L of the one or more low boiling compounds after fermentation for less than about 72 hours, about 60 hours, about 55 hours, or about 10 hours, or about 5 hours at an industrial scale. In one embodiment, the low boiling compounds have, at a standard pressure of 100 kPa (1 bar), a boiling point of less than about 100° C., about 99° C., about 98° C., about 97° C., about 95° C., about 90° C., about 85° C., about 80° C., about 75° C., about 70° C., about 65° C., or about 60° C. In one embodiment, the one or more low boiling compounds are selected from a C3 alcohol, a C3 ketone, or a combination thereof. In one embodiment, the one or more low boiling compounds are selected from 1-propanol, 2-propanol, acetone, or a combination thereof. In one embodiment, the yeast produces negligible amounts of C4 compounds in comparison to ethanol. In one embodiment, the yeast does not produce 1-butanol and 2-butanol or produces 1-butanol and 2-butanol at a negligible amount compared to the amount of ethanol and the one or more low boiling compounds.

In another aspect, the present disclosure provides a process for the production and isolation of ethanol and one or more low boiling compounds, the process comprising: (a) contacting a fermentable carbon source with an ethanol-producing yeast in a fermentation medium; (b) fermenting the carbon source by the yeast in the fermentation medium of (a) to produce a fermentation broth and a fermentation off-gas comprising ethanol and the one or more low boiling compounds; (c) flowing a fermentation off-gas coming from one or more fermenters in (b) through a product recovery unit wherein the flow of the off-gas is counter to a solvent flowing through the product recovery unit and obtaining a solvent stream comprising the one or more low boiling compounds and ethanol; (d) mixing the solvent stream of (c) with the fermentation broth and passing the resulting fermentation mixture through a first separation unit to form a high water content stream comprising ethanol and the one or more low boiling compounds; (e) passing the high water content stream of (d) through a second separation unit to form an intermediate water content stream comprising ethanol and the one or more low boiling compounds; (f) passing the intermediate water content stream of (e) through a dewatering unit to form a low water content stream; and (g) passing the low water content stream of (f) through one or more operational units, separating the ethanol and the one or more low boiling compounds.

In yet another aspect, the present disclosure provides a solvent composition substantially free of aromatic compounds harmful to human health, the composition comprising one or more low boiling compounds isolated by the process described above. In one embodiment, the one or more low boiling compounds comprise acetone, 1-propanol, 2-propanol, or a combination thereof. In one embodiment, the composition is substantially free of benzene, phenol, or a combination thereof.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 1:
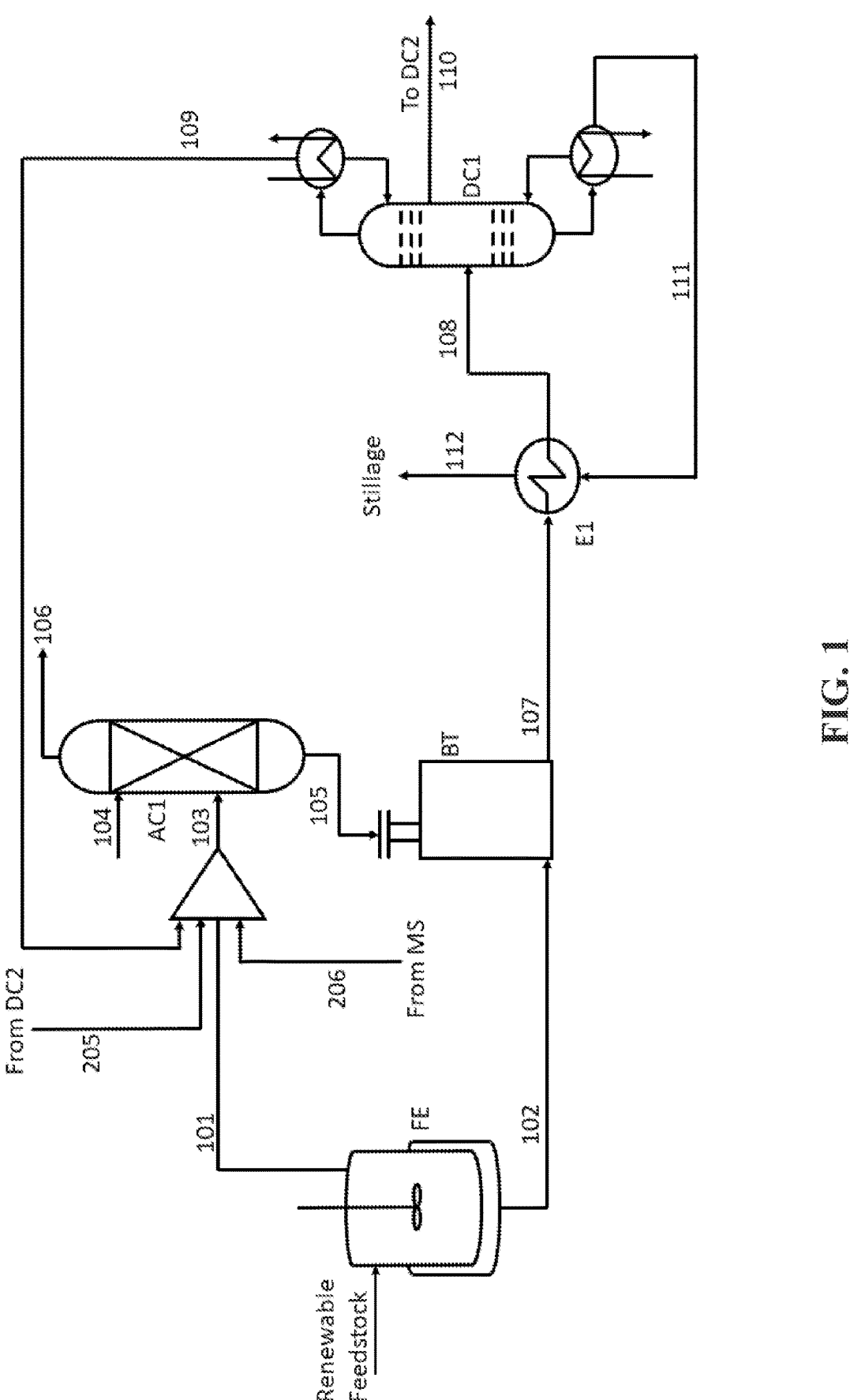
FIG. 1 is a process flowsheet representation for the first common part of the process in which products are recovered from off gas and carbon dioxide and other light compounds are removed. In this part, solids, heavy components and water are also removed at a distillation unit or set.

The present disclosure provides processes for the production of industrially important products using ethanol-producing yeasts that have been modified to use a portion of a fermentable carbon source to produce the product while continuing to produce ethanol. The present disclosure also provides the modified yeasts and methods for the separation of ethanol and the industrially important product(s). In one embodiment, the disclosed methods for the separation of ethanol and the industrially important product(s) are cost efficient and/or energy efficient. In one embodiment, the methods for the production and recovery of the industrially important product(s) are made cost efficient by leveraging existing industrial ethanol production and purification equipment. In one embodiment, the methods for separation are made energy efficient through energy integration, wherein residual heat from the pre-existing ethanol production process can be recovered to run the add-on equipment required for the separation of the industrially important product(s).

As used herein, the term "derived from" may encompass the terms originated from, obtained from, obtainable from, isolated from, and created from, and generally indicates that one specified material finds its origin in another specified material or has features that can be described with reference to another specified material.

As used herein, "exogenous polynucleotide" refers to any deoxyribonucleic acid that originates outside of the microorganism.

As used herein, the term "an expression vector" may refer to a DNA construct containing a polynucleotide or nucleic acid sequence encoding a polypeptide or protein, such as a DNA coding sequence (e.g. gene sequence) that is operably linked to one or more suitable control sequence(s) capable of affecting expression of the coding sequence in a host. Such control sequences include a promoter to affect transcription, an optional operator sequence to control such transcription, a sequence encoding suitable mRNA ribosome binding sites, and sequences which control termination of transcription and translation. The vector may be a plasmid, cosmid, phage particle, bacterial artificial chromosome, or simply a potential genomic insert. Once transformed into a suitable host, the vector may replicate and function independently of the host genome (e.g., independent vector or plasmid), or may, in some instances, integrate into the genome itself (e.g., integrated vector). The plasmid is the most commonly used form of expression vector. However, the disclosure is intended to include such other forms of expression vectors that serve equivalent functions and which are, or become, known in the art.

As used herein, the term "expression" may refer to the process by which a polypeptide is produced based on a nucleic acid sequence encoding the polypeptides (e.g., a gene). The process includes both transcription and translation.

As used herein, the term "gene" may refer to a DNA segment that is involved in producing a polypeptide or protein (e.g., fusion protein) and includes regions preceding and following the coding regions as well as intervening sequences (introns) between individual coding segments (exons).

As used herein, the term "heterologous," with reference to a nucleic acid, polynucleotide, protein or peptide, may refer to a nucleic acid, polynucleotide, protein or peptide that does not naturally occur in a specified cell, e.g., a host cell. It is intended that the term encompass proteins that are encoded by naturally occurring genes, mutated genes, and/or synthetic genes. In contrast, the term homologous, with reference to a nucleic acid, polynucleotide, protein or peptide, refers to a nucleic acid, polynucleotide, protein or peptide that occurs naturally in the cell.

As used herein, the term a "host cell" may refer to a cell or cell line, including a cell such as a microorganism which a recombinant expression vector may be transfected for expression of a polypeptide or protein (e.g., fusion protein). Host cells include progeny of a single host cell, and the progeny may not necessarily be completely identical (in morphology or in total genomic DNA complement) to the original parent cell due to natural, accidental, or deliberate mutation. A host cell may include cells transfected or transformed in vivo with an expression vector.

As used herein, the term "introduced," in the context of inserting a nucleic acid sequence or a polynucleotide sequence into a cell, may include transfection, transformation, or transduction and refers to the incorporation of a nucleic acid sequence or polynucleotide sequence into a eukaryotic or prokaryotic cell wherein the nucleic acid sequence or polynucleotide sequence may be incorporated into the genome of the cell (e.g., chromosome, plasmid, plastid, or mitochondrial DNA), converted into an autonomous replicon, or transiently expressed.

As used herein, the term "non-naturally occurring" or "modified" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Non-naturally occurring microbial organisms of the disclosure can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely. Those skilled in the art will understand that the genetic alterations, including metabolic modifications exemplified herein, are described with reference to a suitable host organism and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. Such genetic alterations include, for example, genetic alterations of species homologs, in general, and in particular, orthologs, paralogs or nonorthologous gene displacements.

As used herein, the term "operably linked" may refer to a juxtaposition or arrangement of specified elements that allows them to perform in concert to bring about an effect. For example, a promoter may be operably linked to a coding sequence if it controls the transcription of the coding sequence.

As used herein, "1-propanol" is intended to mean n-propanol with a general formula $CH_3CH_2CH_2OH$ (CAS number—71-23-8).

As used herein, "2-propanol" is intended to mean isopropyl alcohol with a general formula $CH_3CH_3CHOH$ (CAS number—67-63-0).

As used herein, the term "a promoter" may refer to a regulatory sequence that is involved in binding RNA polymerase to initiate transcription of a gene. A promoter may be an inducible promoter or a constitutive promoter. An inducible promoter is a promoter that is active under environmental or developmental regulatory conditions.

As used herein, the term "a polynucleotide" or "nucleic acid sequence" may refer to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Such polynucleotides or nucleic acid sequences may encode amino acids (e.g., polypeptides or proteins such as fusion proteins). Because the genetic code is degenerate, more than one codon may be used to encode a particular amino acid, and the present disclosure encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms polynucleotide, nucleic acid, and oligonucleotide are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S (thioate), P(S)S (dithioate), $(O)NR_2$ (amidate), P(O)R, P(O)OR', $COCH_2$ (formacetal), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, the term a "protein" or "polypeptide" may refer to a composition comprised of amino acids and recognized as a protein by those of skill in the art. The conventional one-letter or three-letter code for amino acid residues is used herein. The terms protein and polypeptide are used interchangeably herein to refer to polymers of amino acids of any length, including those comprising linked (e.g., fused) peptides/polypeptides (e.g., fusion proteins). The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, related proteins, polypeptides or peptides may encompass variant proteins, polypeptides or peptides. Variant proteins, polypeptides or peptides differ from a parent protein, polypeptide or peptide and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, the term "recovered," "isolated," "purified," and "separated" may refer to a material (e.g., a protein, peptide, nucleic acid, polynucleotide or cell) that is removed from at least one component with which it is naturally associated. For example, these terms may refer to a material which is substantially or essentially free from components which normally accompany it as found in its native state, such as, for example, an intact biological system.

As used herein, the term "recombinant" may refer to nucleic acid sequences or polynucleotides, polypeptides or proteins, and cells based thereon, that have been manipulated by man such that they are not the same as nucleic acids, polypeptides, and cells as found in nature. Recombinant may also refer to genetic material (e.g., nucleic acid sequences or polynucleotides, the polypeptides or proteins they encode, and vectors and cells comprising such nucleic acid sequences or polynucleotides) that has been modified to alter its sequence or expression characteristics, such as by mutating the coding sequence to produce an altered polypeptide, fusing the coding sequence to that of another coding sequence or gene, placing a gene under the control of a different promoter, expressing a gene in a heterologous organism, expressing a gene at decreased or elevated levels, expressing a gene conditionally or constitutively in manners different from its natural expression profile, and the like.

As used herein, the term "transfection" or "transformation" may refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into host cells. Examples of transfection techniques include, but are not limited to, calcium phosphate precipitation, DEAE-dextranmediated transfection, lipofection, electroporation, and microinjection.

As used herein, the term "transformed," "stably transformed," and "transgenic" may refer to a cell that has a non-native (e.g., heterologous) nucleic acid sequence or polynucleotide sequence integrated into its genome or as an episomal plasmid that is maintained through multiple generations.

As used herein, the term "vector" may refer to a polynucleotide sequence designed to introduce nucleic acids into one or more cell types. Vectors include cloning vectors, expression vectors, shuttle vectors, plasmids, phage particles, single and double stranded cassettes and the like.

As used herein, the term "wild-type," "native," or "naturally-occurring" proteins may refer to those proteins found in nature. The terms wild-type sequence refers to an amino acid or nucleic acid sequence that is found in nature or naturally occurring. In some embodiments, a wild-type sequence is the starting point of a protein engineering project, for example, production of variant proteins.

As used herein, the term "non-toxic concentrations" may refer to concentrations of a co-product that have no effect or only a minimal effect on the level of ethanol produced by a yeast modified to produce the co-product compared to the level of ethanol produced by an otherwise similar unmodified yeast. For example, when non-toxic concentrations are present, the level of ethanol produced by the modified yeast may be reduced by no more than 30%, 20%, or, most preferably, no more than 10% compared to the level of ethanol produced by an unmodified yeast.

Unless defined otherwise herein, all technical and scientific terms used herein have the same meaning as commonly understood by one of ordinary skill in the art to which this disclosure belongs. Singleton, et al., Dictionary of Microbiology and Molecular Biology, second ed., John Wiley and Sons, New York (1994), and Hale & Markham, The Harper Collins Dictionary of Biology, Harper Perennial, NY (1991) provide one of skill with a general dictionary of many of the terms used in this disclosure. Further, it will be understood that any of the substrates disclosed in any of the pathways herein may alternatively include the anion or the cation of the substrate.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Use of the term "about" or "approximately" when referring to a number or a numerical range means that the number or numerical range referred to is an approximation within experimental variability (or within statistical experimental error), and thus the number or numerical range may vary from, for example, between 1% and 15% of the stated number or numerical range. Numeric ranges provided herein are inclusive of the numbers defining the range. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Modified Yeast

The yeast used in the fermentation process described elsewhere herein may be modified (e.g., genetically engineered) by any method known in the art to comprise and/or express one or more polynucleotides coding for enzymes in a pathway that catalyze a conversion of a fermentable carbon source to one or more products. In some embodiments, a yeast may be modified (e.g., genetically engineered) by any method known in the art to comprise and/or express one or more polynucleotides coding for enzymes in a pathway that catalyze a conversion of a fermentable carbon source to intermediates in a pathway for the production of a co-product such as 1-propanol, acetone, and/or 2-propanol. In some embodiments, the yeast may comprise one or more exogenous polynucleotides encoding one or more enzymes in pathways for the production of the desired product(s), such as 1-propanol, acetone, 2-propanol, or a combination thereof from a fermentable carbon source.

In one embodiment, the modified yeast is an ethanol-producing yeast which has been modified to co-produce one or more low boiling point compounds. In some embodiments of each or any of the above or below mentioned embodiments, the ethanol-producing yeast is *Saccharomyces cerevisiae*. In some embodiments of each or any of the above or below mentioned embodiments, the *Saccharomyces cerevisiae* is an industrial strain. Suitable industrial ethanol producer strains include, but are not limited to, the *S. cerevisiae* PE-2, CAT-1, and Red strains. In some embodiments of each or any of the above or below mentioned embodiments, the *Saccharomyces cerevisiae* is any common strain used in ethanol industry, a typical laboratory strain, or any strain resulting from the typical method of crossing between strains. In some embodiments of each or any of the above or below mentioned embodiments, the *Saccharomyces cerevisiae* is an industrial strain already used in existing industrial ethanol processes, wherein such processes are based on sugar cane, sugar beets, or most preferably, corn as a raw material.

In some embodiments of each or any of the above or below mentioned embodiments, the ethanol-producing yeast is modified to express exogenous phosphoketolase to redirect part of the carbon flow from a renewable raw material (e.g., glucose) to intermediates (e.g., acetate, acetyl-CoA) and therefore to the low-boiling point compound of interest (e.g., acetone, isopropanol) through the pentose phosphate pathway (PPP).

In some embodiments of each or any of the above or below mentioned embodiments, the ethanol-producing yeast is modified to express exogenous phosphoenolpyruvate carboxykinase (PEPCK) kinase to redirect carbon flow from PEP to oxaloacetate. In some embodiments of each or any of the above or below mentioned embodiments, the ethanol-producing yeast is modified to express a phosphoenolpyruvate carboxykinase (PEPCK) to redirect the carbon flow from a renewable raw material (e.g., glucose) to intermediates (e.g., oxaloacetate, malonate semialdehyde) and therefore to the low-boiling point compound of interest (e.g., 1-propanol, acetone, isopropanol).

In some embodiments of each or any of the above or below mentioned embodiments, the ethanol-producing yeast is modified to knock-out endogenous genes and/or downregulate endogenous enzymes including, but not limited to, pyruvate decarboxylase (e.g., PDC1), pyruvate kinase (e.g., PYK1), and alcohol dehydrogenases. In some embodiments of each or any of the above or below mentioned embodiments, the downregulation of endogenous genes is carried out by a weak promoter (either natural or synthetic), natural or synthetic terminators, natural or synthetic transcription factors, degron peptides, iCRISPR, or any other technique known in the art for downregulation of genes in yeast. In some embodiments of each or any of the above or below mentioned embodiments, the weak promoter is pADH1, pCYC1, pSTE5, pREV1, pURA3, pRPLA1, pGAPl, pNUP57, or pMET25.

In some embodiments of each or any of the above or below mentioned embodiments, the co-products are produced at non-toxic concentrations for the ethanol-producing yeast. In some embodiments of each or any of the above or below embodiments, the engineered ethanol-producing yeast was genetically modified to co-produce the low-boiling point compound of interest (e.g., acetone, 1-propanol, 2-propanol, or a combination thereof) along with ethanol as the major product in the fermentation broth (see, e.g., U.S. Patent Application Publication No. 2021/0261987).

In some embodiments of each or any of the above or below mentioned embodiments, the engineered ethanol-producing yeast modified to produce the low-boiling point compound of interest (e.g., acetone, isopropanol, 1-propanol) remains the ethanol fermentation robustness and performance required for the industrial deployment. In some embodiments of each or any of the above or below mentioned embodiments, the recombinant yeast has most of the ethanol fermentation robustness and performance preserved compared to its mother industrial ethanol-producing yeast, enabling its use on already existing industrial ethanol processes.

A modified yeast as provided herein may comprise:

one or more polynucleotides coding for enzymes in a pathway that catalyzes a conversion of a fermentable carbon source to succinyl-CoA, one or more polynucleotides coding for enzymes in a pathway that catalyzes a conversion of a fermentable carbon source to 1,2-propanediol, one or more polynucleotides coding for enzymes in a pathway that catalyzes a conversion of a fermentable carbon source to lactate, one or more polynucleotides coding for enzymes in a pathway that catalyzes a conversion of a fermentable carbon source to β-alanine, one or more polynucleotides coding for enzymes in a pathway that catalyzes a conversion of a fermentable carbon source to threonine, one or more polynucleotides coding for enzymes in a pathway that catalyzes a conversion of a fermentable carbon source to citramalate, one or more polynucleotides coding for enzymes in a pathway that catalyzes a conversion of fermentable carbon source to malonate semialdehyde, one or more polynucleotides coding for enzymes in a pathway that catalyzes a conversion of succinyl-CoA to methylmalonyl-CoA, one or more polynucleotides coding for enzymes in a pathway that catalyzes a conversion of threonine to 2-ketobutyrate (2-kB), one or more polynucleotides coding for enzymes in a pathway that catalyzes a conversion of citramalate to 2-ketobutyrate (2-kB), one or more polynucleotides coding for enzymes in a pathway that catalyzes a conversion of 3-alanine to malonate semialdehyde, one or more polynucleotides coding for enzymes in a pathway that catalyzes a conversion of malonate semialdehyde to 3-hydroxypropionate (3-HP), one or more polynucleotides coding for enzymes in a pathway that catalyzes a conversion of lactate to acrylyl-CoA, one or more polynucleotides coding for enzymes in a pathway that catalyzes a conversion of 3-alanine to acrylyl-CoA, one or more polynucleotides coding for enzymes in a pathway that catalyzes a conversion of 3-HP to acrylyl-CoA, one or more polynucleotides coding for enzymes in a pathway that catalyzes a conversion of methylmalonyl-CoA to propionyl-CoA, one or more polynucleotides coding for enzymes in a pathway that catalyzes a conversion of 2-kB to propionyl-CoA, one or more polynucleotides coding for enzymes in a pathway that catalyzes a conversion of acrylyl-CoA to propionyl-CoA, one or more polynucleotides coding for enzymes in a pathway that catalyzes a conversion of propionyl-CoA to propionaldehyde, one or more polynucleotides coding for enzymes in a pathway that catalyzes a conversion of 1,2-propanediol to propionaldehyde, and/or one or more polynucleotides coding for enzymes in a pathway that catalyzes a conversion of propionaldehyde to 1-propanol.

A modified microorganism as provided herein may comprise:

one or more polynucleotides coding for enzymes in a pathway that catalyzes a conversion of fermentable carbon source to pyruvate, one or more polynucleotides coding for enzymes in a pathway that catalyzes a conversion of fermentable carbon source to malonate semialdehyde (MSA), one or more polynucleotides coding for enzymes in a pathway that catalyzes a conversion of pyruvate to acetyl-CoA, one or more polynucleotides coding for enzymes in a pathway that catalyzes a conversion of MSA to acetyl-CoA;

one or more polynucleotides coding for enzymes in a pathway that catalyzes a conversion of acetyl-CoA to acetoacetyl-CoA, one or more polynucleotides coding for enzymes in a pathway that catalyzes a conversion of acetyl-CoA to malonyl-CoA, one or more polynucleotides coding for enzymes in a pathway that catalyzes a conversion of malonyl-CoA to acetoacetyl-CoA, one or more polynucleotides coding for enzymes in a pathway that catalyzes a conversion of acetoacetyl-CoA to acetoacetate, one or more polynucleotides coding for enzymes in a pathway that catalyzes a conversion of acetoacetyl-CoA to hydroxymethylglutaryl-CoA (HMG-CoA), one or more polynucleotides coding for enzymes in a pathway that catalyzes a conversion of HMG-CoA to acetoacetate, one or more polynucleotides coding for enzymes in a pathway that catalyzes a conversion of acetoacetate to acetone, and/or one or more polynucleotides coding for enzymes in a pathway that catalyzes a conversion of acetone to 2-propanol.

A modified microorganism as provided herein may comprise:

one or more polynucleotides coding for enzyme that catalyzes a conversion of fermentable carbon source to acetyl-CoA through the pentose phosphate pathway (PPP), one or more polynucleotides coding for enzymes in a pathway that catalyzes a conversion of acetyl-CoA to acetoacetyl-CoA, one or more polynucleotides coding for enzymes in a pathway that catalyzes a conversion of acetoacetyl-CoA to acetoacetate, one or more polynucleotides coding for enzymes in a pathway that catalyzes a conversion of acetoacetate to acetone, and/or one or more polynucleotides coding for enzymes in a pathway that catalyzes a conversion of acetone to 2-propanol.

In some embodiments, the yeast is *Saccharomyces cerevisiae, Kluyveromyces lactis* or *Pichia pastoris*.

In some embodiments, the yeast is *Saccharomyces cerevisiae* and is an industrial ethanol producer yeast, i.e., the modified yeast derived from a yeast strain already used in existing industrial ethanol fermentation processes and assets, wherein such industrial yeast has appropriate and distinguished robustness and fermentation performance to the production of ethanol.

In some embodiments, the yeast is *Saccharomyces cerevisiae* and is an industrial ethanol producer yeast already used in existing industrial ethanol fermentation processes and assets, wherein such processes and assets are based on sugar cane, sugar beets or corn as a raw material.

In some embodiments, the yeast is *Saccharomyces cerevisiae* and is an industrial ethanol producer yeast derived from or industrially used in already existing corn-based ethanol fermentation processes and assets.

In some embodiments, the yeast is additionally modified to comprise one or more tolerance mechanisms including, for example, tolerance to a produced molecule (e.g., 1-propanol, acetone, 2-propanol), and/or organic solvents. A yeast modified to comprise such a tolerance mechanism may provide a means to increase titers of fermentations and/or may control contamination in an industrial scale process.

Host cells are transformed or transfected with the above-described expression or cloning vectors for production of one or more enzymes as disclosed herein or with polynucleotides coding for one or more enzymes as disclosed herein and cultured in conventional nutrient media modified as appropriate for inducing promoters, selecting transformants, or amplifying the genes encoding the desired sequences.

Host cells containing desired nucleic acid sequences coding for the disclosed enzymes may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44, (1979); Barnes et al., Anal. Biochem. 102: 255 (1980); U.S. Pat. Nos. 4,767,704; 4,657, 866; 4,927,762; 4,560,655; or 5,122,469; WO 90/103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Pathways for Production of 1-Propanol

In one embodiment, the modified yeast produces the low boiling point compound 1-propanol. Metabolic pathways for the production of 1-propanol include pathways that produce 1-propanol from intermediates including, but not limited to, malonate semialdehyde, 3-hydroxypropionic acid, 1,2-propanediol, 2-ketobutyrate (2-kB), succinyl-CoA, and acrylyl-CoA. Specifically, the 2-kB, succinyl-CoA, and acrylyl-CoA intermediates converge into propionyl-CoA. Both propionyl-CoA and 1,2-propanediol are converted to propionaldehyde and to 1-propanol by a bi-functional aldehyde/alcohol dehydrogenase or by the action of an aldehyde dehydrogenase (acetylating) in combination with an alcohol dehydrogenase.

In one pathway, 1-propanol is produced via the succinyl-CoA route whereby a sugar source is converted to succinyl-CoA via glycolysis and the citric acid cycle (TCA cycle), followed by the isomerization of succinyl-CoA to methylmalonyl-CoA by a methylmalonyl-CoA mutase, and the decarboxylation of methylmalonyl-CoA to propionyl-CoA by a methylmalonyl-CoA decarboxylase. Aldehyde and alcohol dehydrogenases catalyze additional conversions to convert propionyl-CoA to propionaldehyde and propional-dehyde to 1-propanol (see, e.g., U.S. Patent Application Publication No. 2013/0280775). In another pathway, 1-pro-panol is produced via 1,2-propanediol whereby a sugar source undergoes multiple conversions catalyzed by a meth-ylglyoxal synthase, an aldo-ketoreductase or a glyoxylate reductase and an aldehyde reductase. Hydrolase and dehy-drogenases catalyze additional conversions to convert 1,2-propanediol to propanal and propanal to 1-propanol (see, e.g., U.S. Pat. No. 9,957,530).

In another pathway, 1-propanol is produced from a 2-kB intermediate via conversions from threonine and/or citra-malate. For example, 2-kB can be converted to propionyl-CoA or directly to propionaldehyde by a 2-oxobutanoate dehydrogenase or a 2-oxobutanoate decarboxylase, respec-tively (see, e.g., U.S. Patent Application Publication No. 2014/0377820).

In another pathway, 1-propanol is produced from oxalo-acetate, β-alanine, and malonate semialdehyde intermedi-ates that converted to 3-hydroxypropionate (3-HP), 3-HP-CoA, acrylyl-CoA, propionyl-CoA and then 1-propanol (see, e.g., U.S. Patent Application Publication No. 2020/0216864).

In other pathways, 1-propanol is produced from β-ala-nine, oxaloacetate, lactate, or 3-hydroxypropionate (3-HP) intermediates that are converge to acrylyl-CoA, which is converted to propionyl-CoA by an acrylyl-CoA reductase (see, e.g., U.S. Patent Application Publication No. 2014/0377820). As described above, propionyl-CoA can be con-verted to 1-propanol by aldehyde and alcohol dehydroge-nases.

Pathways for Production of 1-Propanol, Acetone, and/or 2-Propanol

In one embodiment, the modified yeast produces the low boiling point compound(s) 1-propanol, 2-propanol, acetone, or a combination thereof. In one embodiment, the modified yeast produces the low boiling point compound 1-propanol, acetone, 2-propanol, or a combination thereof through dif-ferent metabolic pathways and intermediates. Acetone can be generated from several pathways, including but not limited to primary and secondary metabolism reactions, as glycolysis, terpenoid biosynthesis, atrazine degradation and cyanoamino acid metabolism. In one pathway, acetyl-CoA can be derived from pyruvate and/or malonate semialdehyde by a pyruvate dehydrogenase and a malonate semialdehyde dehydrogenase, respectively. Acetyl-CoA is converted to acetoacetyl-CoA by a thiolase or an acetyl-CoA acetyltrans-ferase (see, e.g., U.S. Patent Application Publication No. 2018/0179558). Alternatively, acetoacetyl-CoA can be formed through malonyl-CoA by acetoacetyl-CoA synthase. Once acetoacetyl-CoA is formed, its conversion to acetoac-etate can be done by an acetoacetyl-CoA transferase or through HMG-CoA by hydroxymethylglutaryl-CoA syn-thase and hydroxymethylglutaryl-CoA lyase. Acetoacetate conversion to acetone is done by an acetoacetate decarboxy-lase.

In another pathway, 2-propanol is produced from propane and/or acetone as precursors. As described above, acetone is generated from acetyl-CoA by multiple reactions and is converted to isopropanol by an isopropanol dehydrogenase (see, e.g., U.S. Patent Application Publication No. 2018/0179558). In another pathway, propane is produced from a butyrate intermediate and isopropanol is generated by a propane 2-monooxygenase. Biosynthesis of propane in

*Escherichia coli* from glucose having butyrate as interme-diate is described in Kallio et al. (2014) Nat Commun, 5 (4731).

In one embodiment, acetone and/or isopropanol is pro-duced through a metabolic pathway comprising one or more polynucleotide coding for enzymes with phosphoketolase activity that enables the conversion of a renewable carbon source (e.g., glucose) into intermediates (e.g., acetyl-CoA) and further into acetone and/or isopropanol. In one embodi-ment, the engineered metabolic pathway is the pentose phosphate pathway (PPP). In one embodiment, the engi-neered metabolic pathway comprises the conversion of D-xylulose 5-phosphate to D-glyceraldehyde 3-phosphate and acetyl phosphate, or the conversion of D-fructose 6-phosphate to D-erythrose 4-phosphate and acetyl phos-phate. In some embodiments, D-xylulose 5-phosphate is converted to D-glyceraldehyde 3-phosphate and acetyl phosphate by a phosphoketolase. In some embodiments, D-fructose 6-phosphate is converted to D-erythrose 4-phos-phate and acetyl phosphate by a phosphoketolase. Phospho-ketolases include enzymes classified as (EC) 4.1.2.9 and (EC) 4.1.2.22. In one embodiment, phosphoketolase is from *Bifidobacterium animalis, Bifidobacterium longum, Bifido-bacterium adolescentis, Bifidobacterium breve, Aspergillus nidulans, Aspergillus niger, Clostridium acetobutylicum, Leuconostoc mesenteroides, Lactobacillus plantarum, Lac-tobacillus casei, Lactobacillus pentosum* and *Lactobacillus acidophilus.* In some embodiments, the engineered meta-bolic pathway comprises the conversion of acetyl phosphate to acetate by one or more native and/or heterologous phos-phatases. In some embodiments, the engineered metabolic pathway comprises the conversion of acetate to acetyl-CoA by a native and/or heterologous acetyl-CoA synthetase. In yet another embodiment, the modified yeast comprises a combination of enzymes to convert the acetyl-CoA into acetoacetyl-CoA, acetoacetate, acetone and/or isopropanol.

Method for the Co-Production of Ethanol and a Low Boiling Compound

In another aspect, the present disclosure provides a pro-cess for the co-production of ethanol and one or more low boiling compounds, the process comprising: contacting a fermentable carbon source with an ethanol-producing yeast in a fermentation medium; and fermenting the carbon source by the yeast in the fermentation medium to produce a fermentation broth and a fermentation off-gas comprising ethanol and the one or more low boiling compounds.

In one embodiment, the fermentable carbon source is contacted with an ethanol-producing yeast comprising one or more polynucleotides coding for enzymes in a pathway that catalyzes a conversion of the fermentable carbon source to any of the intermediates in the production of the low boiling point compound(s) and one or more polynucleotides coding for enzymes in a pathway that catalyze a conversion of the one or more intermediates to the low boiling point compound(s) in a fermentation media; and expressing the one or more polynucleotides coding for the enzymes in the pathway that catalyzes a conversion of the fermentable carbon source to the one or more intermediates in the production of the low boiling point compound(s) and one or more polynucleotides coding for enzymes in a pathway that catalyze a conversion of the one or more intermediates to the low boiling point compound(s). In one embodiment, ethanol and the one or more low boiling point compounds are produced by contacting any of the genetically modified yeasts provided herein with the fermentable carbon source. In one embodiment, the ethanol-producing yeast is a geneti-cally modified *Saccharomyces cerevisiae.*

In one embodiment, the fermentation products of the disclosure may be prepared by conventional processes for industrial sugarcane, wheat, cassava, sweet sorghum, sugar beet, beet, or corn ethanol production. In one embodiment, the fermentable carbon source comprises a C5, C6, or C12 sugar. In one embodiment, the C5, C6, or C12 sugar originates from a renewable source that already used in a conventional ethanol mill. Therefore, in some embodiments, the C5, C6, or C12 sugar source is sugarcane, corn, wheat, cassava, sweet sorghum, sugar beets, beets, cellulose, biomass, or biomass waste. In one embodiment, the sugar is a C6 sugar. In one embodiment, the C6 sugar is glucose. In one embodiment, the low boiling compounds have, at a standard pressure of 100 kPa (1 bar), a boiling point of less than about 100° C., about 99° C., about 98° C., about 97° C., about 95° C., about 90° C., about 85° C., about 80° C., about 75° C., about 70° C., about 65° C., or about 60° C. In one embodiment, the low boiling compounds have, at a standard pressure of 100 kPa (1 bar), a boiling point of less than about 100° C. In one embodiment, the one or more low boiling compounds have a boiling point that is less than the boiling point of water, under standard atmospheric conditions. In one embodiment, the low boiling compound is a low boiling ketone and/or alcohol. In one embodiment, the one or more low boiling compounds are selected from a C3 alcohol, a C3 ketone, or a combination thereof. In one embodiment, the low boiling compound is 1-propanol, 2-propanol, and/or acetone.

In one embodiment, an aqueous stream comprising the C5, C6, or C12 sugar fermentable carbon source enters a fermentation unit and is contacted with the ethanol-producing yeast. In one embodiment, a solution comprising the C5, C6, or C12 sugar enters the fermenter by a renewable feedstock pipe. In one embodiment, the C5, C6, or C12 sugar solution comprises from about 65% w/w to about 85% w/w of water, about 10% w/w to about 25% w/w of C5, C6, or C12 sugar, about 1% w/w to about 3.5% w/w of celluloses, and about 0% to about 5% w/w of residual biomass, depending on the feedstock. In one embodiment, the C5, C6, or C12 sugar solution comprises about 75% w/w water, about 18% w/w of C5, C6, or C12 sugar, about 2.4% w/w celluloses, and about 0% to 5% w/w of residual biomass. In one embodiment, the sugar is a C6 sugar. In one embodiment, the C6 sugar is glucose. In one embodiment, the fermentation media may additionally contain suitable minerals, salts, cofactors, buffers and other components suitable for the growth and maintenance of the cultures.

In one embodiment, the mixture of genetically modified yeast and the C5, C6, or C12 sugar undergoes a fermentation step, wherein the genetically modified yeast produces the target low-boiling compound(s) like acetone, 1-propanol, and 2-propanol along with ethanol. In one embodiment, the fermentation step is carried out either in accordance with a batch operation mode, a multi-stage batch operation mode, a semi-continuous operational mode (or "fed-batch" mode), or in accordance with an operational mode known as a continuous mode; these are well known to the person skilled in the art.

In one embodiment, the fermentation step may be conducted by different engineered yeast strains, keeping the industrial ethanol performance (titer, yield, productivity) similar to what is expected or already obtained by the ethanol millers, all always producing ethanol in larger quantities than the target low-boiling compound(s). In one embodiment, the fermentation step is carried out at a temperature of about 30° C. to about 37° C. In one embodiment, the process of producing the ethanol and the one or more low boiling point compounds can be implemented in existing industrial ethanol mills with little or ideally no modification in the industrial fermentation area.

In one embodiment, the step of fermentation produces greater than about 90 g/L, about 100 g/L, about 110 g/L, about 120 g/L, about 130 g/L, about 140 g/L, or about 150 g/L of ethanol after fermentation for less than about 72 hours, about 60 hours, about 55 hours, about 50 hours, about 45 hours, or about 40 hours, or about 10 hours, or about 5 hours at an industrial scale. In one embodiment, the step of fermentation produces greater than about 2.5 g/L, about 5 g/L, about 10 g/L, about 15 g/L, about 20 g/L or about 30 g/L of the one or more low boiling compounds after fermentation for less than about 72 hours, about 60 hours, about 55 hours, about 50 hours, about 45 hours, or about 40 hours, or about 10 hours, or about 5 hours at an industrial scale. In one embodiment, the one or more low boiling compounds are C3 compounds.

In one embodiment, the fermentation step reaches a high titer of greater than about 110 g/L, about 120 g/L, about 130 g/L, about 140 g/L, about 150 g/L, or about 160 g/L of total solvents. In one embodiment, the fermentation step reaches a high titer of greater than about 140 g/L of total solvents. In one embodiment, the fermentation step reaches a productivity of greater than about 1.0 g/L·h, about 1.5 g/L·h, about 2.0 g/L·h, about 2.5 g/L·h, about 3.0 g/L·h, about 3.5 g/L·h, about 4.0 g/L·h, about 4.5 g/L·h, or about 5.0 g/L·h of solvents. In one embodiment, the term "total solvents" refers to the combination of ethanol and the one or more low boiling point compounds. In one embodiment the fermentation step reaches a productivity of greater than about 2.5 g/L·h of solvents.

In one embodiment, the yeast produces at least about 2.5 g/L, about 5 g/L, about 7.5 g/L, about 10 g/L, about 12.5 g/L, about 15 g/L, about 17.5 g/L, or about 20 g/L acetone alongside with at least about 80 g/L, about 90 g/L, about 100 g/L, about 110 g/L, about 120 g/L, about 130 g/L, about 140 g/L, or about 150 g/L ethanol in about 50 to about 60 hours of fermentation time, reaching high titer (>140 g/L of total solvents) and productivity (>2.5 g/L·h of solvents). In some embodiments, the yeast produces at least about 5 g/L acetone alongside with at least about 135 g/L ethanol in about 50 to about 60 hours of fermentation time, reaching high titer (>140 g/L of total solvents) and productivity (>2.5 g/L·h of solvents). In another embodiment, the yeast produces at least about 10 g/L acetone alongside with at least about 130 g/L ethanol in about 50 to about 60 hours of fermentation time reaching, high titer (>140 g/L of total solvents) and productivity (>2.5 g/L·h of solvents). In another embodiment, the yeast produces at least about 15 g/L acetone alongside with at least about 125 g/L ethanol in about 50 to about 60 hours of fermentation time, reaching high titer (>140 g/L of total solvents) and productivity (>2.5 g/L·h of solvents).

In one embodiment, the yeast does not produce compounds with more than 3 carbon atoms. In one embodiment, the yeast does not produce 1-butanol and 2-butanol or produces 1-butanol and 2-butanol at a negligible amount compared to the amount of ethanol and the one or more low boiling compounds.

In one embodiment, the ethanol and the one or more low boiling compounds in the fermentation broth is separated by a process described herein.

Separation of Ethanol and Low Boiling Compounds

In another aspect, the present disclosure relates to a process for the isolation of one or more low boiling compounds from a fermentation broth and a fermentation off-gas, the process comprising:

(a) flowing a fermentation off-gas coming from one or more fermenters through a product recovery unit wherein the flow of the off-gas is counter to a solvent flowing through the product recovery unit and obtaining a solvent stream comprising the one or more low boiling compounds and ethanol;

(b) mixing the solvent stream of (a) with the fermentation broth and passing the resulting fermentation mixture through a first separation unit to form a high water content stream, comprising ethanol and the one or more low boiling compounds;

(c) passing the high water content stream of (b) through a second separation unit to form an intermediate water content stream, comprising ethanol and the one or more low boiling compounds;

(d) passing the ethanol intermediate water content stream of (c) through a dewatering unit to form a low water content stream; and (e) passing the low water content stream of (d) through one or more operational units, separating the ethanol and the one or more low boiling compounds.

The isolation process can treat an alcoholic fermentation broth comprising the one or more low boiling compounds described herein diluted in ethanol and water. In some embodiments, the concentration of the one or more low boiling products in the fermentation broth ranges from about 5 g/L to 30 g/L, and ethanol as the main product from a concentration of about 40 g/L to 140 g/L. In one embodiment, the concentration of the low boiling compound(s) and ethanol depends on the feedstock used for the industrial ethanol fermentation processes (e.g. corn, wheat, sugar beets, sugarcane, or other biomass materials). The output of this fermentation process leaves the fermenter either in the off-gas (vapor phase) or in the broth (liquid phase).

In one embodiment, the fermentation off-gas of (a) contains one or more incondensable gases, water, ethanol, and the one or more low boiling compounds. In one embodiment, the fermentation off-gas comprises between about 80% w/w to about 98% w/w, about 85% w/w to about 98% w/w, about 90% w/w to about 98% w/w, or about 92% w/w to about 98% w/w of an incondensable gas. In one embodiment, the fermentation off-gas comprises between about 0.5% w/w to about 15% w/w, about 0.5% w/w to about 12% w/w, about 0.5% w/w to about 10% w/w, about 1% w/w to about 10% w/w, about 1% w/w to about 8% w/w, about 1% w/w to about 6% w/w, or about 2% w/w to about 5% of ethanol and the one or more low boiling compounds. In one embodiment, the fermentation off-gas comprises between about 0.01% w/w to about 15% w/w, about 0.01% w/w to about 12% w/w, about 0.01% w/w to about 10% w/w, about 0.01% w/w to about 8% w/w, about 0.01% w/w to about 6% w/w, about 0.1% w/w to about 6% w/w, about 0.1% w/w to about 4% w/w, or about 0.5% w/w to 3% w/w water. In one embodiment, the incondensable gas is primarily carbon dioxide.

In one embodiment, the fermentation broth of (a) comprises water, the low boiling compound(s), ethanol, and one or more contaminants or congeners. In one embodiment, the fermentation broth comprises the low-boiling compound(s) in a concentration between about 0.5 g/L and about 100 g/L, about 0.5 g/L and about 90 g/L, about 0.5 g/L and about 80 g/L, about 0.5 g/L and about 70 g/L, about 0.5 g/L and about 60 g/L, about 0.5 g/L and about 50 g/L, about 1 g/L and about 40 g/L, or about 5 g/L and about 30 g/L. In one embodiment, ethanol is the main product in the fermentation broth at a concentration of between about 10 g/L and about 200 g/L, about 20 g/L and about 180 g/L, about 30 g/L and about 160 g/L, or about 40 g/L and about 140 g/L. In one embodiment, the fermentation broth comprises less than about 30 g/L, about 25 g/L, about 20 g/L, about 15 g/L, about 10 g/L or about 5 g/L of volatile contaminants or congeners that have to be removed to purify the target products (e.g., acetone). In one embodiment, the congeners were already present in the feedstock or were produced by the fermentation process, and may be organic acids, organic alcohols, and other organic compounds. In one embodiment, the congeners may include, but are not limited to, aldehydes (e.g. acetaldehyde and acetal), ketones (e.g. diketone, ethyl methyl ketone, and 2-butanone), esters (e.g. ethyl formate, ethyl acetate, propyl acetate, 2-methylpropyl acetate, 3-methylbutyl acetate, ethyl hexanoate, hexyl acetate, ethyl lactate, ethyl isovalerate, ethyl-alpha-methylbutyrate, 2-methylpropyl hexanoate, ethyl lactate, 2-methylpropyl hexanoate, ethyl octanoate, 3-methylbutyl hexanoate, ethyl phenylacetate, phenyl ethyl acetate, ethyl decanoate, ethyl dodecanoate, and ethyl tetradecanoate), alcohols (e.g. methanol, 2-methylbutan-1-ol, 3-methylbutan-1-ol, 1-pentanol, 2-phenylethan-1-ol, and glycerol), and organic acids (e.g. acetic acid, lactic acid, propionic acid, i-butyric acid, butyric acid, valeric acid, i-valeric acid, hexanoic acid, octanoic acid, decanoic acid, and dodecanoric acid).

In one embodiment, in the product recovery unit of (a), the products present in the off-gas are absorbed by the water added at the top of the unit. In one embodiment, the product recovery unit is an absorption column or a scrubber column. In one embodiment, between about 0.25 parts to about 4 parts of solvent flow counter to about one part of off-gas on a mass basis. In another embodiment, about 0.5 part to 2 parts solvent flow counter to about one part of off-gas on a mass basis. In one embodiment, the solvent is at a temperature of about 5° C. to about 100° C., about 5° C. to about 90° C., about 5° C. to about 80° C., about 5° C. to about 70° C., about 5° C. to about 60° C., about 5° C. to about 50° C., about 5° C. to about 50° C., or about 5° C. to about 45° C. In one embodiment, the solvent is at a temperature of about 30° C.

It would be possible to use other organic solvents as done in ABE or IBE processes described by IFP Energies Nouvelles U.S. Pat. No. 10,961,489 B2, in which the solvent may be selected from hydrocarbon compounds with a linear or branched chain, aromatic hydrocarbon compounds, carboxylic acids, alcohols, or esters. However, the use of such solvents would require a solvent regeneration unit prior to mixing recovered products with the liquid phase of the bioreactor in order to avoid DDGS or other solids in broth contamination. Therefore, this unit would require more capital expenditures and avoidable changes in existing ethanol mills. Environmental risks associated with the hydrocarbons are an additional disadvantage of this process.

In one embodiment, step (a) yields a solvent stream comprising the one or more low boiling compounds and ethanol as well as a purified gas stream. In one embodiment, the purified gas stream comprises more than about 70%, about 75%, about 80%, about 85%, about 90%, or about 95% incondensable gases and less than about 30%, about 25%, about 20%, about 15%, about 10%, about 5%, about 1%, or about 0.5% of ethanol and the low boiling compound(s).

In one embodiment, the fermentation mixture of (b) is stored in a tank. In one embodiment, the fermentation mixture tank is integrated with a stillage heat exchanger and the stillage heat exchanger preheats the fermentation mixture before it is passed through the first separation unit of (b). In one embodiment, the fermentation mixture of (b) is called "beer" and is stored in a beer tank. In one embodiment, the first separation unit is an evaporator, a distillation column, a set of distillation columns, a combination of a centrifuge and a distillation column, or a combination of a centrifuge and a set of distillation columns. In one embodiment, the distillation column is capable of treating solids, usually called beer or mash column. In one embodiment, the high water content stream of (b) comprises ethanol, the low boiling compound(s), and water. In one embodiment, the high water content stream comprises between about 10% w/w to about 90% w/w, about 25% w/w to about 90% w/w, about 30% w/w to about 90% w/w, about 30% w/w to about 85% w/w, about 35% w/w to about 85% w/w, or about 35% w/w to 80% w/w of water. In one embodiment, the high water content stream comprises about 10% w/w to about 90% w/w, about 10% w/w to about 85% w/w, about 10% w/w to about 80% w/w, about 15% w/w to about 70% w/w, about 15% w/w to about 65% w/w, or 20% w/w to 65% w/w of ethanol and the low boiling compound(s). In one embodiment, the high water content stream is maintained at a temperature of between about 40° C. and about 180° C., about 40° C. and about 170° C., about 40° C. and about 160° C., about 50° C. and about 160° C., about 50° C. and about 150° C., about 60° C. and about 150° C., about 60° C. and about 140° C., or about 70° C. to about 135° C.

In one embodiment, if a distillation column is used in (b), the column operates at a pressure of between about 0.1 bar and about 5 bar or about 0.1 bar and about 3 bar. In one embodiment, prior to distillation the beer is heated to a temperature of between about 40° C. and 150° C., about 45° C. and about 145° C., about 50° C. and about 140° C., about 55° C. and about 135° C., about 60° C. and about 130° C., about 65° C. and about 125° C., or about 70° C. and about 115° C. In one embodiment, heat integrations with the distillation column condensers will depend on the products being separated and operating conditions of the other separation units.

In one embodiment, the first separation unit removes an output "stillage" stream comprising water, heavy components, and solids to a stillage tank. In one embodiment, the stillage can have different end uses, according to the feedstock selected, and may have a content of about 55% w/w to about 99% w/w of water, about 60% w/w to about 99% w/w of water, or about 65% w/w to about 99% w/w of water and the rest will be composed of solids present in the feedstock and C5, C6, or C12 sugars that were not consumed during fermentation, in the range of about 45% w/w or less. In one embodiment, the stillage stream leaves the first separation unit at a temperature of about 30° C. and about 200° C., about 30° C. and about 190° C., about 30° C. and about 180° C., about 40° C. and about 180° C., about 50° C. and about 180° C., about 50° C. and about 170° C., about 50° C. and about 160° C., about 60° C. and about 160° C., about 60° C. and about 150° C., or about 65° C. and about 140° C.

In one embodiment, the process further comprises recycling a gas stream output from the first separation unit of (b) by passing the gas stream output through steps (a) and (b). In one embodiment, the gas stream output comprises an incondensable gas which is removed as the gas stream is passed through steps (a) and (b) and wherein the gas stream further comprises the one or more low boiling compounds which are recovered. In one embodiment, the gas stream output comprises between about 20% w/w to about 95% w/w, about 25% w/w to about 95% w/w, about 30% w/w to about 95% w/w, about 35% w/w to about 90% w/w, or about 40% w/w to about 85% w/w incondensable gas. In one embodiment, the gas stream output comprises between about 1% w/w to about 75% w/w, about 1% w/w to about 75% w/w, about 1% w/w to about 75% w/w, about 5% w/w to about 70% w/w, about 5% w/w to about 65% w/w, about 10% w/w to about 65% w/w, or about 15% w/w to about 60% w/w of ethanol and the one or more low boiling compounds. In one embodiment, the incondensable gas comprises $CO_2$. In one embodiment, the gas stream leaves the first separation unit at a temperature of about 10° C. and about 160° C., about 15° C. and about 155° C., about 20° C. and about 150° C., about 25° C. and about 145° C., about 30° C. and about 140° C., about 30° C. and about 130° C., about 30° C. and about 120° C., about 30° C. and about 110° C., about 30° C. and about 105° C., or about 30° C. and about 100° C.

In one embodiment, the second separation unit of (c) is a rectifier column, a distillation column, or a set of distillation columns.

In one embodiment, the second separation unit of (c) is a distillation column known as a rectifier column. In one embodiment, the second separation unit removes an output stream comprising primarily water. In one embodiment, the output stream comprises between about 70% w/w to about 100% w/w, about 75% w/w to about 100% w/w, or about 80% w/w to about 100% w/w water. In one embodiment, the output stream is maintained at a temperature of about 40° C. to about 200° C., about 45° C. to about 195° C., about 45° C. to about 185° C., about 45° C. to about 185° C., about 45° C. to about 175° C., about 50° C. to about 170° C., about 50° C. to about 160° C., about 55° C. to about 155° C., about 60° C. to about 150° C., about 60° C. to about 140° C., or about 65° C. to about 135° C. In one embodiment, the process further comprises the step of recycling the water stream output of (c) to an upstream fermentation process which produces the fermentation broth of (a). In one embodiment, this recycling reduces the water consumption of the process described herein. In another embodiment, the process further comprises the step of recycling the bottom output stream of (c) by passing the bottom output stream through step (c). In yet another embodiment, the process further comprises the step of recycling the water stream output of (c) back to (b).

In one embodiment, the second separation unit removes a side stream comprising fusel oil. In one embodiment, the side stream is at a temperature of between about 15° C. and about 180° C., about 20° C. to about 175° C., about 25° C. to about 170° C., about 30° C. to about 165° C., about 35° C. to about 160° C., about 40° C. to about 155° C., about 45° C. to about 150° C., about 45° C. to about 140° C., about 50° C. to about 135° C., about 50° C. to about 125° C., or about 55° C. to about 120° C.

In one embodiment, the intermediate water content stream of (c) comprises ethanol, water, and the one or more low boiling compounds. In one embodiment, the intermediate water content stream comprises between about 60% w/w to about 95% w/w, about 65% w/w to about 95% w/w, about 70% w/w to about 95% w/w, or about 75% w/w to about 95% w/w ethanol. In one embodiment, the intermediate water content stream further comprises between about 5% w/w to about 30% w/w, about 5 w/w to about 25% w/w, about 5% w/w to about 20% w/w, about 5% w/w to about 15% w/w, or about 5% w/w to about 10% w/w water. In one embodiment, the intermediate water content stream further comprises between about 0.1 w/w to about 25% w/w, about 5% w/w to about 20% w/w, or about 1% w/w to about 15% w/w of the one or more low boiling compounds. In one embodiment, the intermediate water content stream is maintained at a temperature of between about 15° C. and 180° C., about 20° C. and about 175° C., about 20° C. to about 165°

C., about 25° C. to about 160° C., about 30° C. to about 155° C., about 35° C. to about 150° C., about 35° C. to about 140° C., about 40° C. to about 135° C., about 40° C. to about 125° C., about 45° C. to about 115° C., or about 50° C. to about 110° C. In one embodiment, the rectifier operates at a pressure of between about 0.1 bar to about 5 bar or about 0.1 bar to about 3 bar.

In one embodiment, the process further comprises recycling a vent gas stream output from the rectifier column of (c) by passing the vent gas stream output through step (a) to reduce product loss.

In one embodiment, the process further comprises removing a top vapor stream from the second separation unit of (c) and recycling the top vapor stream by combining the top vapor stream with the fermentation off-gas. In one embodiment, the process further comprises passing the combined stream comprising the top vapor stream and the fermentation off-gas through step (a). In another embodiment, the process further comprises passing the combined stream comprising the top vapor stream and the fermentation off-gas through steps (a) and (b). In yet another embodiment, the process further comprises passing the combined stream comprising the top vapor stream and the fermentation off-gas through steps (a), (b), and (c).

In one embodiment, the dewatering unit of (d) is a membrane separation system or a molecular sieve system. In one embodiment, the low water content stream of (d) comprises between about 15% w/w and 0.5%, about 10% w/w and 0.5% w/w, about 5% w/w and 0.5% w/w, or about 2.5% w/w and 0.5% w/w water. Although not wishing to be limited by theory, it is believed that the presence of the dewatering step before the separation of the ethanol from the other target products is key to the operating expense reduction, the preservation of product specification, and the economic viability of the process described herein. In one embodiment, the dewatering step is critical for the process when propanol is present because the presence of higher amounts of water will complicate the separation of ethanol from propanol. In one embodiment, the process further comprises the step of recycling a water stream output from the dewatering unit of (d) by passing the water stream output through steps (c) and (d). In some embodiments, recycling the water stream output through steps (c) and (d) functions to recover any desired ethanol or low boiling point compound(s) which are present in the water stream output.

In one embodiment, the process further comprises removing a top vapor stream from the dewatering unit of (d) and recycling the top vapor stream by combining the top vapor stream with the fermentation off-gas. In one embodiment, the process further comprises passing the combined stream comprising the top vapor stream and the fermentation off-gas through step (a). In another embodiment, the process further comprises passing the combined stream comprising the top vapor stream and the fermentation off-gas through steps (a) and (b). In another embodiment, the process further comprises passing the combined stream comprising the top vapor stream and the fermentation off-gas through steps (a), (b), and (c). In yet another embodiment, the process further comprises passing the combined stream comprising the top vapor stream and the fermentation off-gas through steps (a), (b), (c), and (d).

In one embodiment, the one or more low boiling compounds are selected from a C3 alcohol, a C3 ketone, or a combination thereof. In one embodiment, the one or more low boiling compounds are selected from 1-propanol, 2-propanol, acetone, or a combination thereof. In one embodiment, the fermentation broth comprises C4 alcohols at negligible amounts. In one embodiment, the fermentation broth does not comprise 1-butanol and 2-butanol or comprises 1-butanol and 2-butanol at a negligible amount compared to the amount of ethanol and the one or more low boiling compounds.

Isolation of Ethanol and Acetone

In one embodiment, the low boiling compound is acetone and the one or more operational units of (e) is a pervaporation system or at least one distillation column which separates the ethanol from the acetone. In one embodiment, the pervaporation system or the at least one distillation column of (e) optionally comprise a heat exchanger or reboiler that can be heat integrated with the second separation unit of (c) or with any other process unit that has proper heat available. In one embodiment, the at least one distillation column of (e) operates at a pressure of between about 0.1 bar to about 5 bar, about 0.1 bar to about 3.0 bar, or about 0.1 bar to about 2 bar. In one embodiment, ethanol leaves the bottom of the at least one distillation column at a concentration of between about 80% w/w to about 100% w/w, about 85% w/w to about 100% w/w, about 90% w/w to about 100% w/w, or about 95% w/w to about 100% w/w. In one embodiment, the acetone leaves the top or at the side of the distillation column at a concentration of between about 80% w/w to about 100% w/w, about 85% w/w to about 100% w/w, about 90% w/w to about 100% w/w, or about 95% w/w to about 100% w/w.

In one embodiment, the presence of congeners (e.g., acetaldehyde, methanol) alongside with ethanol and the low boiling point compound (e.g., acetone) may require a sequence of distillation equipment to enable the recovery of the ethanol and the low boiling compound(s) within the desired market specification.

In one embodiment, the low boiling compound is acetone, and one or more operational units are required to recover acetone at the desired product specification. In one embodiment, the low boiling compound is acetone, and one or more distillation columns are required to recover and purify acetone at the desired product specification. In one embodiment, the low boiling compound is acetone, and two distillation columns are required to recover and purify acetone at the desired product specification.

In one embodiment, the one or more operational units further separate a contaminant stream. In one embodiment, the contaminant stream comprises acetaldehyde and acetone. In one embodiment, the contaminant stream is combined with one or more side streams from steps (b), (c), and/or (d), wherein the one or more side streams comprise contaminants as well as ethanol, and/or acetone. In one embodiment, the combined stream is passed through an adsorption column to recover the ethanol and/or the acetone. In one embodiment, the ethanol and/or acetone are recovered by adding water to the adsorption column and recovering the ethanol and/or acetone in an aqueous solution at the bottom of the column. In one embodiment, the recovered acetone and/or ethanol are passed through step (b) to purify the recovered acetone and/or ethanol to a desired purity. In another embodiment, the recovered acetone and/or ethanol are passed through steps (b) and (c) to purify the recovered acetone and/or ethanol to a desired purity. In another embodiment, the recovered acetone and/or ethanol are passed through steps (b), (c), and (d) to purify the recovered acetone and/or ethanol to a desired purity. In yet another embodiment, the recovered acetone and/or ethanol are passed through steps (b), (c), (d), and (e) to purify the recovered acetone and/or ethanol to a desired purity.

In one embodiment, the process further comprises recycling a vent gas stream output from the one or more operational units of (e) by passing the vent gas stream output through step (a) to reduce product loss.

Isolation of Ethanol, Acetone, and 1-Propanol

In another embodiment, the low boiling compounds are acetone and 1-propanol. In one embodiment, an operational unit of at least one distillation column or a set of two or more distillation columns is required at step (e) to obtain the three products at the purity required for final application. In one embodiment, a set of two or more distillation columns is required at step (e) to obtain the three products at the purity required for final application. In one embodiment, the distillation columns of (e) are: (i) a first distillation system which separates 1-propanol from a mixture of ethanol and acetone, (ii) a second distillation system which purifies the 1-propanol from (i) to a desired purity, and (iii) a third distillation system which separates the mixture of (i) into ethanol and acetone. In some embodiments, the acetone separated in the third distillation system comprises one or more light contaminants. In one embodiment, the one or more light contaminants comprise acetaldehyde, methanol, or a mixture thereof. In one embodiment, the mixture of acetone and light contaminant(s) enters a fourth distillation system which separates the acetone to a desired purity. In one embodiment, the distillation columns (i) and (iii) each independently optionally comprise a reboiler that can be heat integrated with the second separation unit of (c) or with any other process unit that has proper heat available. In one embodiment, when the temperature between the reboilers of distillation columns (i) and (iii) does not allow a heat integration, vacuum can be applied on them. In one embodiment, each of the first, second, and third distillation systems operate at mild pressure and temperature conditions.

In one embodiment, the first distillation column removes most of the 1-propanol at the bottom, at a high purity. In one embodiment, the first distillation column comprises a membrane system separation followed by a distillation unit. In some embodiments, this combination of a membrane system and a distillation unit is used when the low boiling point compound forms a mixture with ethanol that is difficult to separate by conventional distillation. In one embodiment, the second distillation column polishes the 1-propanol to desired purity and then it leaves at the bottom stream of this column. In one embodiment, the third distillation column is a specification column. In one embodiment, a gaseous mixture of ethanol and acetone leaves the top of the first distillation column. In one embodiment, the gaseous mixture is condensed before it enters the third distillation column. In one embodiment, the specification column receives condensed mixture of primarily ethanol with small amounts of acetone. In one embodiment, acetone is isolated as a side product in the specification column, with incondensable gases leaving at the top, and purified ethanol at bottom. In one embodiment, the second and third distillation columns are a single distillation column. In another embodiment, the second and/or third distillation columns are a set of distillation columns. In one embodiment, the presence of congeners alongside with ethanol and the low boiling point compound may require a sequence of distillation equipment to enable the recovery of the ethanol and the low boiling compound(s) within the desired market specification.

In one embodiment, the acetone separated in distillation system (iii) comprises one or more contaminants (referred to as "lights"). In one embodiment, the one or more operational units of (e) further comprise (iv) a fourth distillation system which separates the acetone from the one or more contaminants/"lights." In one embodiment, the one or more contaminants/"lights" comprise acetaldehyde. In one embodiment, the contaminants/"lights" further comprise one or more desired products, such as ethanol, acetone, and/or 1-propanol and the process further comprises recycling the one or more contaminants/"lights" by passing the one or more contaminants/"lights" through step (a) to obtain the one or more desired products. In one embodiment, the contaminants/"lights" further comprise one or more desired products, such as ethanol, acetone, and/or 1-propanol and the process further comprises recycling the one or more contaminants/"lights" by passing the one or more contaminants/"lights" through steps (a) and (b) to obtain the one or more desired products. In one embodiment, the contaminants/"lights" further comprise one or more desired products, such as ethanol, acetone, and/or 1-propanol and the process further comprises recycling the one or more contaminants/"lights" by passing the one or more contaminants/ "lights" through steps (a), (b), and (c) to obtain the one or more desired products. In one embodiment, the contaminants/"lights" further comprise one or more desired products, such as ethanol, acetone, and/or 1-propanol and the process further comprises recycling the one or more contaminants/"lights" by passing the one or more contaminants/ "lights" through steps (a), (b), (c), and (d) to obtain the one or more desired products. In one embodiment, the contaminants/"lights" further comprise one or more desired products, such as ethanol, acetone, and/or 1-propanol and the process further comprises recycling the one or more contaminants/"lights" by passing the one or more contaminants/ "lights" through steps (a), (b), (c), (d), and (e) to obtain the one or more desired products.

In another embodiment, the acetone separated in distillation system (iii) comprises one or more contaminants/ "lights," wherein the contaminants/"lights further comprise one or more desired products, such as ethanol, acetone, and/or 1-propanol and the process further comprises feeding the one or more contaminants/"lights" into a scrubber. In one embodiment, the scrubber is a scrubber column. In one embodiment, the one or more desired products are recovered from the one or more contaminants/"lights" by adsorption with a solvent in the scrubber. In one embodiment, the solvent comprises water. In another embodiment, the one or more desired products are recovered with the one or more contaminants/"lights" by adsorption with a solvent in the scrubber and the process further comprises recycling the solvent comprising the one or more desired products and the one or more contaminants by passing the solvent through step (b). In another embodiment, the one or more desired products are recovered with the one or more contaminants/ "lights" by adsorption with a solvent in the scrubber and the process further comprises recycling the solvent comprising the one or more desired products and the one or more contaminants by passing the solvent through steps (b) and (c). In another embodiment, the one or more desired products are recovered with the one or more contaminants/ "lights" by adsorption with a solvent in the scrubber and the process further comprises recycling the solvent comprising the one or more desired products and the one or more contaminants by passing the solvent through steps (b), (c), and (d). In yet another embodiment, the one or more desired products are recovered with the one or more contaminants/ "lights" by adsorption with a solvent in the scrubber and the process further comprises recycling the solvent comprising the one or more desired products and the one or more contaminants by passing the solvent through steps (b), (c), (d), and (e). In one embodiment, the process further comprises feeding one or more vapor streams from steps (a), (d), or (e) into the scrubber. In one embodiment, the one or more vapor streams from steps (a), (d), or (e) comprise one or more desired products, such as ethanol, acetone, and/or 1-propanol, and the one or more desired products are recovered by adsorption with a solvent in the scrubber.

Isolation of Ethanol, 1-Propanol, and 2-Propanol

In yet another embodiment, the low boiling compounds are 1-propanol and 2-propanol. In one embodiment, at least one distillation column or a set of two or more distillation columns is required as the operational unit of step (e) to obtain the three products at purity required for the final application. In one embodiment, the one or more distillation columns of (e) are: (i) one or more first distillation columns which separate 1-propanol from a mixture of ethanol and 2-propanol, (ii) an extractive distillation unit which uses a solvent to extract 2-propanol from a vapor phase mixture of ethanol and 2-propanol while obtaining a first fraction of pure ethanol and a second fraction comprising solvent, 2-propanol, and ethanol, (iii) one or more second distillation columns which separate the second fraction of (ii) into solvent and a mixture of ethanol and 2-propanol, and (iv) one or more third distillation columns which separate pure 2-propanol from the mixture of (iii), leaving a solution of primarily ethanol with a small amount of 2-propanol. In one embodiment, operational units (ii) to (iv) can be replaced with a system comprising two distillation columns operating under vacuum conditions. In one embodiment, the process further comprises the step of recycling the solvent of (iii) for use in the extractive distillation unit of (ii). In one embodiment, the process further comprises the step of recycling the solution of (iv) by heating the solution to form a vapor and passing the vapor through the extractive distillation unit of (ii). In one embodiment, the process further comprises the step of recycling the solution of (iv) by passing the solution through the extractive distillation unit of (ii). In one embodiment, distillation columns (i) and (iii) each independently comprise a reboiler. In one embodiment, the reboiler of the distillation column of (i) is heat integrated with the second separation unit of (c) and/or the extractive distillation unit of (ii). In another embodiment, the reboiler of the distillation column of (iii) is heat integrated with the second separation unit of (c) and/or the extractive distillation unit of (ii). In another embodiment the reboilers of both distillation columns (i) and (iii) are heat integrated with the second separation unit of (c) and/or the extractive distillation unit of (ii). In another embodiment, the reboiler of distillation column of (i) is heat integrated with any other process unit that has proper heat available. In another embodiment, the reboiler of the distillation column of (iii) is heat integrated with any other process unit that has proper heat available. In another embodiment, the reboilers of both distillation columns (i) and (iii) are heat integrated with any other process unit that has proper heat available. In another embodiment, operational units (ii), (iii), and (iv) are replaced by two distillation columns operating under vacuum conditions which each independently optionally comprise a reboiler that can be heat integrated with a condenser of (c), a condenser of (i), or a combination thereof.

In one embodiment, 1-propanol is isolated at the bottom of the first distillation column since 1-propanol has a higher boiling point than ethanol and 2-propanol. In one embodiment, ethanol and 2-propanol leave at the top of the first distillation column. In one embodiment, the extractive distillation unit uses a solvent with more affinity for 2-propanol than ethanol is used to extract 2-propanol from a vapor phase mixture of ethanol and 2-propanol. In one embodiment, the solvent is limonene. In one embodiment, the vapor phase mixture of ethanol and 2-propanol and the solvent is fed as liquid at the top of the extractive distillation unit. In one embodiment, first fraction of (ii) is obtained at desired purity at the top of the extractive distillation unit while the second fraction of (ii) leaves at the bottom. In another embodiment, the extractive distillation unit of (ii) is replaced with a vacuum distillation unit. In one embodiment, wherein the extractive distillation unit of (ii) is replaced with a vacuum distillation unit, the second distillation column of (iii) is absent and the mixture of ethanol and 2-propanol obtained from the vacuum distillation unit is passed through the third distillation column of (iv).

In one embodiment, the solvent of (ii) can be recovered at the bottom of the second distillation column of (iii) and recycled to the extractive distillation unit of (ii). In one embodiment, the mixture of ethanol and 2-propanol in (iii) leaves the top of the second distillation column. In one embodiment, 2-propanol is obtained at the bottom of the third distillation column of (iv). In one embodiment, a mixture of the ethanol with some 2-propanol is also obtained from the third distillation column of (iv) and is recycled to the extractive distillation unit of (ii). In one embodiment, the first distillation column of (i) and the third distillation column of (iii) are single distillation columns. In another embodiment, the first distillation column of (i) and/or the third distillation column of (iii) are a set of distillation columns. In one embodiment, the presence of congeners alongside with ethanol and the low boiling compound(s) requires a sequence of distillation columns in (i) and/or (iii) to enable the recovery of ethanol and the one or more low boiling compound(s) within the desired market specification.

Isolation of Ethanol and 2-Propanol

In yet another embodiment, the low boiling compound is 2-propanol and one or more distillation columns is required as the operational unit of step (e) to obtain the two products at purity required for the final application. In one embodiment, the one or more distillation columns of (e) comprise: (i) an extractive distillation unit which uses a solvent to extract 2-propanol from a vapor phase mixture of ethanol and 2-propanol while obtaining a first fraction of pure ethanol and a second fraction comprising solvent, 2-propanol, and ethanol, (ii) one or more first distillation columns which separate the second fraction of (i) into solvent and a mixture of ethanol and 2-propanol, and (iii) one or more second distillation columns which separate pure 2-propanol from the mixture of (ii), leaving a solution of primarily ethanol with a small amount of 2-propanol. In one embodiment, the process further comprises the step of recycling the solvent of (ii) for use in the extractive distillation unit of (i). In one embodiment, the process further comprises the step of recycling the solution of (iii) by passing the solution through the extractive distillation unit of (i). In one embodiment, the process further comprises the step of recycling the solution of (iii) by heating the solution to form a vapor and passing the vapor through the extractive distillation unit of (i). In one embodiment, distillation column (iii) comprises a reboiler that is heat integrated with the extractive distillation unit of (i) or with any other process unit that has proper heat available.

In one embodiment, operational units (i), (ii), and (iii) are replaced by two distillation columns under vacuum conditions which each independently optionally comprise a reboiler that can be heat integrated with a condenser of (c).

Industrial Plant Separation of Ethanol and Low Boiling Compounds

In another aspect, the present disclosure relates to an industrial plant process for the isolation of one or more low boiling compounds from a fermentation broth and a fermentation off-gas, the process comprising steps (a)-(e) described elsewhere herein.

In one embodiment, the one or more fermenters of (a) were operated at a temperature of between about 20° C. and 50° C., about 25° C. and 45° C., about 30° C. and 40° C., or about 35° C. In one embodiment, the one or more fermenters of (a) were operated at a pressure of between about 0.1 bar and 2.0 bar, about 0.2 bar and 1.9 bar, about 0.3 bar and 1.8 bar, about 0.4 bar and 1.7 bar, about 0.5 bar and 1.6 bar, about 0.6 bar and 1.5 bar, about 0.7 bar and 1.4 bar, about 0.8 bar and 1.3 bar, about 0.9 bar and 1.2 bar, about 1.0 bar and 1.2 bar, or about 1.1 bar of absolute pressure. In one embodiment, the fermenters of (a) produce ethanol. In one embodiment, the fermenters of (a) further produce one or more minor fermentative products selected from acetaldehyde, acetone, methanol, ethyl-acetate, isopropyl alcohol, 1-propanol, isoamyl alcohol, and acetic acid.

In one embodiment, the fermentation off-gas of (a) comprises one or more incondensable gases, water, ethanol, and the one or more low boiling compounds. In one embodiment, the fermentation off-gas comprises between about 80% w/w to about 98% w/w, about 85% w/w to about 98% w/w, about 90% w/w to about 98% w/w, or about 92% w/w to about 98% w/w, or about 94% of an incondensable gas. In one embodiment, the fermentation off-gas comprises between about 0.5% w/w to about 15% w/w, about 0.5% w/w to about 12% w/w, about 0.50% w/w to about 10% w/w, about 10% w/w to about 10% w/w, about 10% w/w to about 8% w/w, about 1% w/w to about 6% w/w, or about 2% w/w to about 5% of ethanol and the one or more low boiling compounds. In one embodiment, the fermentation off-gas comprises between about 0.01% w/w to about 15% w/w, about 0.01% w/w to about 12% w/w, about 0.01% w/w to about 10% w/w, about 0.01% w/w to about 8% w/w, about 0.01% w/w to about 6% w/w, about 0.1% w/w to about 6% w/w, about 0.1% w/w to about 4% w/w, or about 0.5% w/w to 3% w/w water. In one embodiment, the incondensable gas is primarily carbon dioxide.

In one embodiment, the fermentation off-gas of is mixed with a recycle off-gas stream from the first separation unit of (b) and a recycle off-gas stream from the second separation unit of (c). In one embodiment, the mixture of the fermentation off-gas with the off-gas from (b) and (c) is flowed through the product recovery unit of (a). In one embodiment, the mixture of the fermentation off-gas with the off-gas from (b) and (c) is flowed through the bottom the product recovery unit of (a). In one embodiment, the product recovery unit operates at between about 0.1 bar and 2.0 bar, about 0.2 bar and 1.9 bar, about 0.3 bar and 1.8 bar, about 0.4 bar and 1.7 bar, about 0.5 bar and 1.6 bar, about 0.6 bar and 1.5 bar, about 0.7 bar and 1.4 bar, about 0.8 bar and 1.3 bar, about 0.8 bar and 1.2 bar, about 0.9 bar and 1.1 bar, or about 1.0 bar of absolute pressure. In one embodiment, the product recovery unit contains 10 stages for the recovery of the products present in the mixture of the fermentation off-gas with the off-gas from (b) and (c). In one embodiment, water is fed into the top of the product recovery unit. In one embodiment, water is flowed into the top of the product recovery unit at a rate of about 1 t/h to 50 t/h, about 5 t/h to 45 t/h, about 10 t/h to 40 t/h, about 15 t/h to 35 t/h, about 20 t/h to 30 t/h, or about 26 t/h. In one embodiment, the solvent used in the product recovery unit absorbs the one or more low boiling compounds and ethanol, forming a solvent stream which is mixed with the fermentation broth in step (b).

In one embodiment, the fermentation broth is discharged from the one or more fermenters at a flow rate of between about 25 t/h and 250 t/h, about 35 t/h and 240 t/h, about 45 t/h and 230 t/h, about 55 t/h and 220 t/h, about 65 t/h and 210 t/h, about 75 t/h and 200 t/h, about 85 t/h and 190 t/h, about 95 t/h and 180 t/h, about 105 t/h and 170 t/h, about 115 t/h and 160 t/h, about 125 t/h and 150 t/h, about 130 t/h and 140 t/h, or about 135 t/h. In one embodiment, the fermentation broth comprises between about 0.1 wt. % to 40 wt. %, about 0.1 wt. % to 30 wt. %, about 0.1 wt. % to 20 wt. %, about 1 wt. % to 20 wt. %, about 5 wt. % to 20 wt. %, about 10 wt. % to 5 wt. %, or about 13 wt. % of the one or more low boiling compounds and ethanol. In one embodiment, the fermentation broth is mixed with the solvent stream of (a) in step (b), forming a fermentation mixture. In one embodiment, the fermentation broth is mixed with the solvent stream of (a) by feeding both into a beer tank simultaneously, resulting in the fermentation mixture of step (b).

In one embodiment, the fermentation mixture of step (b) has a temperature of between about 15° C. to 150° C., about 15° C. to 140° C., about 15° C. to 130° C., about 15° C. to 120° C., about 15° C. to 110° C., about 15° C. to 100° C., about 15° C. to 90° C., about 15° C. to 80° C., about 15° C. to 70° C., about 15° C. to 60° C., about 25° C. to 60° C., about 25° C. to 50° C., about 30° C. to 45° C., or about 36° C. In one embodiment, the fermentation mixture is preheated in a heat exchanger where it exchanges heat with a bottom stream from the first separation unit of (b). In one embodiment, during heat exchange, the fermentation mixture reaches a temperature of between about 50° C. to 200° C., about 50° C. to 190° C., about 50° C. to 180° C., about 50° C. to 170° C., about 50° C. to 160° C., about 50° C. to 150° C., about 60° C. to 140° C., about 70° C. to 130° C., about 80° C. to 120° C., about 90° C. to 110° C., or about 100° C. In one embodiment, after heat exchange, the fermentation mixture is fed into the first separation unit of (b). In one embodiment, the first separation unit comprises a distillation column. In one embodiment, the distillation column comprises 32 stages. In one embodiment, the distillation column operates at between about 0.1 bar and 3.0 bar, about 0.5 bar and 3.0 bar, about 1.0 bar and 3.0 bar, about 1.2 bar and 2.8 bar, about 1.4 bar and 2.6 bar, about 1.6 bar and 2.4 bar, about 1.8 bar and 2.2 bar, or about 2.0 bar in absolute top pressure.

In one embodiment, in the first separation unit, incondensable gases are removed as a top stream. In one embodiment, the incondensable gases are recycled to the product recovery unit of step (a) to recover the one or more low boiling compounds and/or ethanol. In one embodiment, a high water content stream is obtained from the first separation unit which comprises ethanol and the one or more low boiling compounds. In one embodiment, the high water content stream of (b) comprises between about 10 wt. % to 80 wt. %, about 20 wt. % to 80 wt. %, about 30 wt. % to 80 wt. %, about 40 wt. % to 80 wt. %, about 40 wt. % to 70 wt. %, about 50 wt. % to 70 wt. %, about 50 wt. % to 60 wt. %, or about 56 wt. % ethanol. In one embodiment, the high water content stream of (b) comprises about 0.1 wt. % to 20 wt. %, about 0.1 wt. % to 15 wt. %, about 0.1 wt. % to 10 wt. %, about 1 wt. % to 10 wt. %, about 2 wt. % to 6 wt. %, or about 4 wt. % acetone. In one embodiment, the high water content stream is passed through the second separation unit of (c). In one embodiment, the high water content stream has a flow rate of between about 1 t/h and 100 t/h, about 1 t/h and 90 t/h, about 1 t/h and 80 t/h, about 1 t/h and 70 t/h, about 1 t/h and 60 t/h, about 1 t/h and 50 t/h, about 10 t/h and 50 t/h, about 20 t/h and 50 t/h, about 20 t/h and 40 t/h, about 25 t/h and 35 t/h, or about 31 t/h. In one embodiment, a bottom stream is obtained which comprises solids, heavy components, and the majority of the water. In one embodiment, the bottom stream is used to preheat the fermentation mixture of (b).

In one embodiment, the second separation unit of step (c) operates at between about 0.1 bar and 3.0 bar, about 0.1 bar and 2.8 bar, about 0.1 bar and 2.6 bar, about 0.1 bar and 2.4 bar, about 0.4 bar and 2.4 bar, about 0.6 bar and 2.4 bar, about 0.8 bar and 2.4 bar, about 0.8 bar and 2.2 bar, about 0.8 bar and 2.0 bar, about 1.0 bar and 2.0 bar, about 1.2 bar and 2.0 bar, about 1.4 bar and 2.0 bar, about 1.4 bar and 1.8 bar, or about 1.6 bar in absolute top pressure. In one embodiment, the second separation unit comprises a distillation column. In one embodiment, the distillation column comprises 60 stages. In one embodiment, the intermediate water content stream of (c) is obtained as a side stream from the second separation unit. In one embodiment, volatile contaminants are removed from the second separation unit as at a top stream. In one embodiment, the volatile contaminants are recycled to the product recovery unit of step (a) to obtain the one or more low boiling compounds and/or ethanol. In one embodiment, the intermediate water content stream comprises about 0.1 wt. % to 30 wt. %, about 0.1 wt. % to 25 wt. 5, about 0.1 wt. % to 20 wt. %, about 0.1 wt. % to 15 wt. %, about 1 wt. % to 15 wt. %, about 5 wt. % to 15 wt. %, about 5 wt. % to 10 wt. %, or about 8 wt. % water.

In one embodiment, the intermediate water content stream is passed through the dewatering unit of step (d). In one embodiment, the intermediate water content stream is superheated before it is passed through the dewatering unit. In one embodiment, a low water content stream is formed from step (d). In one embodiment, the low water content stream comprises between about 75 wt. % to 99 wt. %, about 80 wt. % to 99 wt. %, about 85 wt. % to 99 wt. %, about 90 wt. % to 99 wt. %, about 90 wt. % to 95 wt. %, or about 93 wt. % ethanol. In one embodiment, the low water content stream comprises between about 0.1 wt. % to 25 wt. %, about 0.1 wt. % to 20 wt. %, about 0.1 wt. % to 15 wt. %, about 1 wt. % to 15 wt. %, about 1 wt. % to 10 wt. %, or about 6 wt. % acetone. In one embodiment, the low water content stream comprises less than about 5% w/w, about 4% w/w, about 3% w/w, about 2% w/w, about 1% w/w, about 0.75% w/w, or 0.5% w/w water. In one embodiment, the low water content stream comprises about 0.5% w/w water. In one embodiment, the low water content stream has a flow rate of between about 1 t/h to 40 t/h, about 1 t/h to 35 t/h, about 1 t/h to 30 t/h, about 1 t/h to 25 t/h, about 5 t/h to 25 t/h, about 10 t/h to 25 t/h, about 15 t/h to 25 t/h, or about 19 t/h.

In one embodiment, a second stream is formed from step (d). In one embodiment, the second stream comprises between about 30 wt. % to 80 wt. %, about 35 wt. % to 80 wt. %, about 35 wt. % to 75 wt. %, about 40 wt. % to 75 wt. %, about 45 wt. % to 75 wt. %, about 50 wt. % to 75 wt. %, about 55 wt. % to 75 wt. %, about 60 wt. % to 75 wt. %, about 60 wt. % to 70 wt. %, or about 67 wt. % ethanol. In one embodiment, the second stream comprises between about 0.1 wt. % to 25 wt. %, about 0.1 wt. % to 20 wt. %, about 0.1 wt. % to 15 wt. %, about 1 wt. % to 15 wt. %, about 1 wt. % to 10 wt. %, or about 5 wt. % acetone. In one embodiment, the second stream comprises about 1 wt. % to 50 wt. %, about 1 wt. % to 45 wt. %, about 5 wt. % to 45 wt. %, about 5 wt. % to 40 wt. %, about 10 wt. % to 40 wt. %, about 10 wt. % to 35 wt. %, about 15 wt. % to 35 wt. %, about 20 wt. % to 35 wt. %, about 25 wt. % to 35 wt. %, about 25 wt. % to 30 wt. %, or about 28 wt. % water. In one embodiment, the second stream is recycled to the second separation unit of step (c). In one embodiment, the second stream is recycled to the second separation unit at a flow rate of between about 0.1 t/h to 25 t/h, about 0.1 t/h to 20 t/h, about 0.1 t/h to 15 t/h, about 5 t/h to 15 t/h, about 5 t/h to 10 t/h, or about 7 t/h.

In one embodiment, the low water content stream of step (d) comprises a negligible amount of 1-propanol. In one embodiment, the low water content stream comprises less than about 2 wt. %, about 1.5 wt. %, about 1 wt. %, about 0.5 wt. %, about 0.1 wt. %, or about 0.05 wt. % 1-propanol. In one embodiment, the low water content stream comprises primarily ethanol and acetone and is thus sent to a distillation column of step (e). In one embodiment, the distillation column comprises 55 stages. In one embodiment, the distillation column operates at between about 0.1 bar and 3.0 bar, about 0.1 bar and 2.5 bar, about 0.1 bar and 2.0 bar, about 0.1 bar and 1.5 bar, about 0.1 bar and 1.0 bar, about 0.5 bar and 1.0 bar, or about 0.7 absolute top pressure. In one embodiment, anhydrous ethanol is obtained at the bottom of the distillation column. In one embodiment, the anhydrous ethanol comprises greater than 95 wt. %, 95 wt. %, 97 wt. %, 98 wt. %, 99 wt. %, or 99.5 wt. % ethanol. In one embodiment, the anhydrous ethanol comprises about 99 wt. % ethanol. In one embodiment, the anhydrous ethanol has a flow rate of between about 1 t/h to 50 t/h, about 1 t/h to 45 t/h, about 1 t/h to 40 t/h, about 1 t/h to 35 t/h, about 1 t/h to 30 t/h, about 5 t/h to 30 t/h, about 5 t/h to 25 t/h, about 10 t/h to 25 t/h, about 15 t/h to 25 t/h, about 15 t/h to 20 t/h, or about 18 t/h. In one embodiment, a contaminant stream comprising one or more contaminants and acetone is obtained at the top of the distillation column. In one embodiment, the contaminant stream is fed into a second distillation column to further purify and obtain the acetone.

In one embodiment, the contaminant stream is fed into the second distillation column at a flow rate of about 0.1 t/h to 16 t/h, about 0.1 t/h to 14 t/h, about 0.1 t/h to 12 t/h, about 0.1 t/h to 10 t/h, about 0.1 t/h to 8 t/h, about 0.1 t/h to 6 t/h, about 0.1 t/h to 4 t/h, about 0.1 t/h to 2 t/h, about 0.5 t/h to 1.5 t/h, or about 1.2 t/h. In one embodiment, the second distillation comprises 45 stages. In one embodiment, the second distillation column operates at between about 0.1 bar and 3.0 bar, about 0.1 bar and 2.8 bar, about 0.2 bar and 2.8 bar, about 0.4 bar and 2.6 bar, about 0.6 bar and 2.4 bar, about 0.8 bar and 2.2 bar, about 1.0 bar and 2.2 bar, about 1.2 bar and 2.2 bar, about 1.4 bar and 2.2 bar, about 1.6 bar and 2.2 bar, about 1.6 bar and 2.0 bar, or about 1.8 bar top absolute pressure. In one embodiment, acetone is recovered at the bottom of the second distillation column. In one embodiment, the acetone has a flow rate of between about 0.1 t/h to 16 t/h, about 0.1 t/h to 14 t/h, about 0.1 t/h to 12 t/h, about 0.1 t/h to 10 t/h, about 0.1 t/h to 8 t/h, about 0.1 t/h to 6 t/h, about 0.1 t/h to 4 t/h, about 0.1 t/h to 2 t/h, about 0.5 t/h to 1.5 t/h, or about 1.2 t/h. In one embodiment, the acetone has a purity of greater than 95 wt. %, 95 wt. %, 97 wt. %, 98 wt. %, 99 wt. %, or 99.5 wt. %. In one embodiment, the acetone has a purity of about 99.5 wt. %. In one embodiment, the one or more contaminants are removed at the top of the second distillation column. In one embodiment, the contaminants comprise between about 50 wt. % and 99 wt. %, about 55 wt. % and 99 wt. %, about 60 wt. % and 99 wt. %, about 65 wt. % and 99 wt. %, about 70 wt. % and 99 wt. %, about 75 wt. % and 99 wt. %, about 75 wt. % and 95 wt. %, about 80 wt. % and 95 wt. %, about 80 wt. % and 90 wt. %, about 85 wt. % and 90 wt. %, or about 87 wt.

% acetaldehyde. In one embodiment, the contaminants are removed at a flow rate of about 5 kg/h to 50 kg/h, about 10 kg/h to 45 kg/h, about 15 kg/h to 40 kg/h, about 20 kg/h to 35 kg/h, about 25 kg/h to 35 kg/h, or about 30 kg/h.

Pilot Plant Separation of Ethanol and Low Boiling Compounds

In another aspect, the present disclosure relates to a pilot plant process for the isolation of one or more low boiling compounds from a fermentation broth and a fermentation off-gas, the process comprising steps (a)-(e) described elsewhere herein.

In one embodiment, the one or more fermenters of (a) are operated at a temperature of between about 20° C. and 50° C., about 25° C. and 45° C., about 30° C. and about 40° C., or about 35° C. In one embodiment, the one or more fermenters of (a) are operated at a pressure of between about 0.1 bar and 2.0 bar, about 0.2 bar and 1.9 bar, about 0.3 bar and 1.8 bar, about 0.4 bar and 1.7 bar, about 0.5 bar and 1.6 bar, about 0.6 bar and 1.5 bar, about 0.7 bar and 1.4 bar, about 0.8 bar and 1.3 bar, about 0.9 bar and 1.2 bar, about 1.0 bar and 1.2 bar, or about 1.1 bar of absolute pressure. In one embodiment, the fermenters of (a) produce ethanol. In one embodiment, the fermenters of (a) further produce one or more minor fermentative products selected from acetaldehyde, acetone, methanol, ethyl-acetate, isopropyl alcohol, 1-propanol, isoamyl alcohol, and acetic acid.

In one embodiment, the fermentation off-gas of (a) comprises one or more incondensable gases, water, ethanol, and the one or more low boiling compounds. In one embodiment, the fermentation off-gas comprises between about 80% w/w to about 98% w/w, about 85% w/w to about 98% w/w, about 90% w/w to about 98% w/w, or about 92% w/w to about 98% w/w, or about 94% of an incondensable gas. In one embodiment, the incondensable gas is primarily carbon dioxide.

In one embodiment, the fermentation off-gas is flowed through the product recovery unit of step (a). In one embodiment, the fermentation off-gas is flowed at a flow rate of between about 10 kg/h to 100 kg/h, about 20 kg/h to 90 kg/h, about 30 kg/h to 80 kg/h, about 40 kg/h to 80 kg/h, about 50 kg/h to 80 kg/h, about 50 kg/h to 70 kg/h, about 55 kg/h to 65 kg/h, or about 62 kg/h. In one embodiment, the product recovery unit operates at between about 0.1 bar and 2.0 bar, about 0.2 bar and 1.9 bar, about 0.3 bar and 1.8 bar, about 0.4 bar and 1.7 bar, about 0.5 bar and 1.6 bar, about 0.6 bar and 1.5 bar, about 0.7 bar and 1.4 bar, about 0.8 bar and 1.3 bar, about 0.8 bar and 1.2 bar, about 0.9 bar and 1.1 bar, or about 1.0 bar of absolute pressure. In one embodiment, the product recovery unit contains 10 stages for the recovery of the products present in the fermentation off-gas. In one embodiment, the solvent used in the product recovery unit absorbs the one or more low boiling compounds and ethanol, forming a solvent stream which is mixed with the fermentation broth in step (b).

In one embodiment, the fermentation broth is discharged from the one or more fermenters at a flow rate of between about 50 kg/h and 800 kg/h, about 100 kg/h and 750 kg/h, about 150 kg/h and 700 kg/h, about 200 kg/h and 650 kg/h, about 250 kg/h and 600 kg/h, about 300 kg/h and 550 kg/h, about 300 kg/h and 500 kg/h, about 300 kg/h and 450 kg/h, about 300 kg/h and 400 kg/h, about 325 kg/h and 375 kg/h, or about 366 kg/h. In one embodiment, the fermentation broth comprises between about 0.1 wt. % to 40 wt. %, about 0.1 wt. % to 30 wt. %, about 0.1 wt. % to 20 wt. %, about 1 wt. % to 20 wt. %, about 5 wt. % to 20 wt. %, about 10 wt. % to 5 wt. %, or about 13 wt. % of the one or more low boiling compounds and ethanol. In one embodiment, the fermentation broth is mixed with the solvent stream of (a) in step (b), forming a fermentation mixture. In one embodiment, the fermentation broth is mixed with the solvent stream of (a) by feeding both into a beer tank simultaneously, resulting in the fermentation mixture of step (b).

In one embodiment, the fermentation mixture of step (b) has a temperature of between about 15° C. to 150° C., about 15° C. to 140° C., about 15° C. to 130° C., about 15° C. to 120° C., about 15° C. to 110° C., about 15° C. to 100° C., about 15° C. to 90° C., about 15° C. to 80° C., about 15° C. to 70° C., about 15° C. to 60° C., about 25° C. to 60° C., about 25° C. to 50° C., about 30° C. to 45° C., or about 36° C. In one embodiment, the fermentation mixture is preheated in a heat exchanger where it exchanges heat with a bottom stream from the second separation unit of (c). In one embodiment, during heat exchange, the fermentation mixture reaches a temperature of between about 50° C. to 200° C., about 50° C. to 190° C., about 50° C. to 180° C., about 50° C. to 170° C., about 50° C. to 160° C., about 50° C. to 150° C., about 60° C. to 140° C., about 70° C. to 130° C., about 80° C. to 120° C., about 90° C. to 110° C., or about 100° C. In one embodiment, after heat exchange, the fermentation mixture is fed into the first separation unit of (b). In one embodiment, the first separation unit comprises a distillation column. In one embodiment, the distillation column comprises 6 stages. In one embodiment, the distillation column operates at between about 0.1 bar and 2.0 bar, about 0.2 bar and 1.9 bar, about 0.3 bar and 1.8 bar, about 0.4 bar and 1.7 bar, about 0.5 bar and 1.6 bar, about 0.6 bar and 1.5 bar, about 0.7 bar and 1.4 bar, about 0.8 bar and 1.3 bar, about 0.8 bar and 1.2 bar, about 0.9 bar and 1.2 bar, or about 1.1 bar of absolute pressure.

In one embodiment, in the first separation unit, incondensable gases are removed as a top stream. In one embodiment, the incondensable gases are recycled to the product recovery unit of step (a) to recover the one or more low boiling compounds and/or ethanol. In one embodiment, a high water content stream is obtained from the first separation unit which comprises ethanol and the one or more low boiling compounds. In one embodiment, the high water content stream of (b) comprises between about 0.01 wt. % and 50 wt. %, about 0.01 wt. % and 45 wt. %, about 0.01 wt. % and 40 wt. %, about 0.01 wt. % and 30 wt. %, about 0.1 wt. % and 30 wt. %, about 0.1 wt. % and 25 wt. %, about 0.1 wt. % and 20 wt. %, about 0.1 wt. % and 15 wt. %, about 1 wt. % and 15 wt. %, or about 10 wt. % ethanol. In one embodiment, the high water content stream of (b) comprises about 0.01 wt. % to 15 wt. %, about 0.01 wt. % to 10 wt. %, about 0.01 wt. % to 8 wt. %, about 0.01 wt. % to 6 wt. %, about 0.1 wt. % to 6 wt. %, about 0.1 wt. % to 4 wt. %, about 0.1 wt. % to 2 wt. %, or about 1 wt. % acetone.

In one embodiment, the high water content stream is passed through the second separation unit of (c). In one embodiment, the high water content stream has a flow rate of between about 50 kg/h and 1000 kg/h, about 100 kg/h and 950 kg/h, about 150 kg/h to 900 kg/h, about 200 kg/h to 850 kg/h, about 250 kg/h to 800 kg/h, about 300 kg/h to 750 kg/h, about 350 kg/h to 700 kg/h, about 350 kg/h to 600 kg/h, about 400 kg/h to 550 kg/h, about 400 kg/h to 500 kg/h, about 450 kg/h to 475 kg/h, or about 460 kg/h.

In one embodiment, the second separation unit of step (c) operates at between about 0.1 bar and 3.0 bar, about 0.1 bar and 2.8 bar, about 0.1 bar and 2.6 bar, about 0.1 bar and 2.4 bar, about 0.4 bar and 2.4 bar, about 0.6 bar and 2.4 bar, about 0.8 bar and 2.4 bar, about 0.8 bar and 2.2 bar, about 0.8 bar and 2.0 bar, about 1.0 bar and 2.0 bar, about 1.2 bar and 2.0 bar, about 1.4 bar and 2.0 bar, about 1.4 bar and 1.8 bar, or about 1.7 bar in absolute top pressure. In one embodiment, the second separation unit comprises a distillation column. In one embodiment, the distillation column comprises 22 stages. In one embodiment, the second separation unit of step (c) comprises two distillation columns, wherein the first distillation column is described above. In one embodiment, the top stream of the first distillation column of step (c) is bottom fed into the second distillation column of (c). In one embodiment, the top stream of the first distillation column comprises between about 5 wt. % and 75 wt. %, about 5 wt. % and 70 wt. %, about 10 wt. % and 70 wt. %, about 10 wt. % and 65 wt. %, about 15 wt. % and 65 wt. %, about 15 wt. % and 60 wt. %, about 20 wt. % and 60 wt. %, about 20 wt. % and 55 wt. %, about 20 wt. % and 50 wt. %, about 20 wt. % and 45 wt. %, about 20 wt. % and 40 wt. %, about 20 wt. % and 35 wt. %, about 25 wt. % and 35 wt. %, or about 30 wt. % ethanol. In one embodiment, the top stream of the first distillation column comprises between about 0.01 wt. % and 20 wt. %, about 0.01 wt. % and 15 wt. %, about 0.01 wt. % and 10 wt. %, about 0.1 wt. % and 10 wt. %, about 1 wt. % and 10 wt. % about 1 wt. % and 5 wt. %, or about 2 wt. % acetone.

In one embodiment, the top stream of the first distillation column of step (c) enters the bottom of the second distillation column of step (c). In one embodiment, the second distillation column comprises 28 stages. In one embodiment, the second distillation column operates at between about 0.1 bar and 2.0 bar, about 0.2 bar and 1.9 bar, about 0.3 bar and 1.8 bar, about 0.4 bar and 1.7 bar, about 0.5 bar and 1.6 bar, about 0.6 bar and 1.5 bar, about 0.7 bar and 1.4 bar, about 0.8 bar and 1.3 bar, about 0.8 bar and 1.2 bar, about 0.9 bar and 1.2 bar, or about 1.1 bar of top absolute pressure.

In one embodiment, the intermediate water content stream of (c) is obtained as a side stream from the second distillation column of the second separation unit in step (c). In one embodiment, volatile contaminants are removed from the second distillation column of the second separation unit as at a top stream. In one embodiment, a bottom stream from the second distillation column of the second separation unit in step (c) is recycled to the first distillation column of the second separation unit in step (c) to obtain the one or more low boiling compounds and/or ethanol.

In one embodiment, the intermediate water content stream obtained in step (c) comprises about 0.1 wt. % to 30 wt. %, about 0.1 wt. % to 25 wt. 5, about 0.1 wt. % to 20 wt. %, about 0.1 wt. % to 15 wt. %, about 1 wt. % to 15 wt. %, about 5 wt. % to 15 wt. %, about 5 wt. % to 10 wt. %, or about 8 wt. % water. In one embodiment, the intermediate water content stream is passed through the dewatering unit of step (d). In one embodiment, the intermediate water content stream is superheated before it is passed through the dewatering unit. In one embodiment, a low water content stream is formed from step (d). In one embodiment, the low water content stream comprises between about 75 wt. % to 99 wt. %, about 80 wt. % to 99 wt. %, about 85 wt. % to 99 wt. %, about 90 wt. % to 99 wt. %, about 90 wt. % to 95 wt. %, or about 93 wt. % ethanol. In one embodiment, the low water content stream comprises between about 0.1 wt. % to 25 wt. %, about 0.1 wt. % to 20 wt. %, about 0.1 wt. % to 15 wt. %, about 1 wt. % to 15 wt. %, about 1 wt. % to 10 wt. %, or about 5 wt. % acetone. In one embodiment, the low water content stream comprises less than about 5% w/w, about 4% w/w, about 3% w/w, about 2% w/w, about 1% w/w, about 0.75% w/w, or 0.5% w/w water. In one embodiment, the low water content stream comprises about 0.5% w/w water. In one embodiment, the low water content stream has a flow rate of between about 1 kg/h to 100 kg/h, about 1 kg/h to 90 kg/h, about 10 kg/h to 90 kg/h, about 10 kg/h to 80 kg/h, about 20 kg/h to 80 kg/h, about 20 kg/h to 70 kg/h, about 30 kg/h to 70 kg/h, about 30 kg/h to 60 kg/h, about 40 kg/h to 60 kg/h, about 45 kg/h to 55 kg/h, or about 50 kg/h.

In one embodiment, a second stream is formed from step (d). In one embodiment, the second stream comprises between about 30 wt. % to 80 wt. %, about 35 wt. % to 80 wt. %, about 35 wt. % to 75 wt. %, about 40 wt. % to 75 wt. %, about 45 wt. % to 75 wt. %, about 50 wt. % to 75 wt. %, about 55 wt. % to 75 wt. %, about 60 wt. % to 75 wt. %, about 60 wt. % to 70 wt. %, or about 68 wt. % ethanol. In one embodiment, the second stream comprises between about 0.1 wt. % to 25 wt. %, about 0.1 wt. % to 20 wt. %, about 0.1 wt. % to 15 wt. %, about 1 wt. % to 15 wt. %, about 1 wt. % to 10 wt. %, or about 4 wt. % acetone. In one embodiment, the second stream comprises about 1 wt. % to 50 wt. %, about 1 wt. % to 45 wt. %, about 5 wt. % to 45 wt. %, about 5 wt. % to 40 wt. %, about 10 wt. % to 40 wt. %, about 10 wt. % to 35 wt. %, about 15 wt. % to 35 wt. %, about 20 wt. % to 35 wt. %, about 25 wt. % to 35 wt. %, about 25 wt. % to 30 wt. %, or about 28 wt. % water. In one embodiment, the second stream is recycled to the second distillation column of the second separation unit in step (c). In one embodiment, the second stream is recycled to the second separation unit at a flow rate of between about 1 kg/h to 50 kg/h, about 1 kg/h to 40 kg/h, about 1 kg/h to 30 kg/h, about 10 kg/h to 30 kg/h, about 15 kg/h to 25 kg/h, or about 17 kg/h.

In one embodiment, the low water content stream of step (d) comprises a negligible amount of 1-propanol. In one embodiment, the low water content stream comprises primarily ethanol and acetone and is thus sent to a distillation column of step (e). In one embodiment, the distillation column comprises 29 stages. In one embodiment, the distillation column operates at between about 0.1 bar and 3.0 bar, about 0.1 bar and 2.5 bar, about 0.1 bar and 2.0 bar, about 0.1 bar and 1.5 bar, about 0.1 bar and 1.0 bar, about 0.5 bar and 1.0 bar, or about 0.7 absolute top pressure. In one embodiment, anhydrous ethanol is obtained at the bottom of the distillation column. In one embodiment, the anhydrous ethanol comprises greater than 95 wt. %, 95 wt. %, 97 wt. %, 98 wt. %, 99 wt. %, or 99.5 wt. % ethanol. In one embodiment, the anhydrous ethanol comprises about 99 wt. % ethanol. In one embodiment, the anhydrous ethanol has a flow rate of between about 1 kg/h and 100 kg/h, about 10 kg/h and 100 kg/h, about 10 kg/h and 90 kg/h, about 20 kg/h and 90 kg/h, about 20 kg/h and 80 kg/h, about 30 kg/h and 80 kg/h, about 30 kg/h and 70 kg/h, about 40 kg/h and 70 kg/h, about 40 kg/h and 60 kg/h, about 45 kg/h and 55 kg/h, or about 47 kg/h. In one embodiment, a contaminant stream comprising one or more contaminants and acetone is obtained at the top of the distillation column. In one embodiment, the contaminant stream is fed into a second distillation column to further purify and obtain the acetone.

In one embodiment, the contaminant stream is fed into the second distillation column at a flow rate of about 0.1 kg/h to 16 kg/h, about 0.1 kg/h to 14 kg/h, about 0.1 kg/h to 12 kg/h, about 0.1 kg/h to 10 kg/h, about 0.1 kg/h to 8 kg/h, about 0.1 kg/h to 6 kg/h, about 1 kg/h to 6 kg/h, about 1 kg/h to 4 kg/h, or about 2.8 kg/h. In one embodiment, the second distillation comprises 15 stages. In one embodiment, the second distillation column operates at between about 0.1 bar and 3.0 bar, about 0.1 bar and 2.8 bar, about 0.2 bar and 2.8 bar, about 0.4 bar and 2.6 bar, about 0.6 bar and 2.4 bar, about 0.8 bar and 2.2 bar, about 1.0 bar and 2.2 bar, about 1.2 bar and 2.2 bar, about 1.4 bar and 2.2 bar, about 1.6 bar and 2.2 bar, about 1.6 bar and 2.0 bar, or about 1.8 bar top absolute pressure. In one embodiment, acetone is recovered at the bottom of the second distillation column. In one embodiment, the acetone has a flow rate of between about 0.1 kg/h to 16 kg/h, about 0.1 kg/h to 14 kg/h, about 0.1 kg/h to 12 kg/h, about 0.1 kg/h to 10 kg/h, about 0.1 kg/h to 8 kg/h, about 0.1 kg/h to 6 kg/h, about 1 kg/h to 6 kg/h, about 1 kg/h to 4 kg/h, or about 2.6 kg/h. In one embodiment, the acetone has a purity of greater than 95 wt. %, 95 wt. %, 97 wt. %, 98 wt. %, 99 wt. %, or 99.5 wt. %. In one embodiment, the acetone has a purity of about 99.6 wt. %. In one embodiment, the one or more light contaminants are removed at the top of the second distillation column. In one embodiment, the light contaminants comprise between about 20 wt. % to 90 wt. %, about 30 wt. % to 90 wt. %, about 30 wt. % to 80 wt. %, about 40 wt. % to 80 wt. 5, about 50 wt. % to 80 wt. %, about 60 wt. % to 80 wt. %, about 65 wt. % to 75 wt. %, or about 69 wt. % acetone. In one embodiment, the light contaminants comprise between about 1 wt. % and 50 wt. %, about 5 wt. % and 45 wt. %, about 10 wt. % and 40 wt. %, about 15 wt. % and 35 wt. %, about 20 wt. % and 35 wt. %, about 25 wt. % and 35 wt. %, or about 28 wt. % acetaldehyde. In one embodiment, the light contaminants are removed at a flow rate of between about 0.01 kg/h to 15 kg/h, about 0.01 kg/h to 10 kg/h, about 0.01 kg/h to 8 kg/h, about 0.01 kg/h to 6 kg/h, about 0.01 kg/h to 4 kg/h, about 0.01 kg/h to 2 kg/h about 0.01 kg/h to 1 kg/h, about 0.05 kg/h to 1 kg/h, about 0.1 kg/h to 0.5 kg/h, or about 0.2 kg/h. In one embodiment, the light contaminants are sent to an adsorption column.

In one embodiment, the adsorption column comprises 10 stages. In one embodiment, the adsorption column operates at between about 0.1 bar and 2.0 bar, about 0.2 bar and 1.9 bar, about 0.3 bar and 1.8 bar, about 0.4 bar and 1.7 bar, about 0.5 bar and 1.6 bar, about 0.6 bar and 1.5 bar, about 0.7 bar and 1.4 bar, about 0.8 bar and 1.3 bar, about 0.8 bar and 1.2 bar, about 0.9 bar and 1.1 bar, or about 1.0 bar of absolute top pressure. In one embodiment, the light contaminants are mixed with one or more additional streams from earlier steps, such as incondensable gases from the first separation unit of step (b), a volatile contaminant top stream removed from the second distillation column of the second separation unit of step (c), and/or an additional side stream from step (d). In one embodiment, the mixture of light contaminants and the one or more additional streams from earlier steps comprises about 1 wt. % to about 70 wt. %, about 1 wt. % to 60 wt. %, about 1 wt. % to 50 wt. %, about 10 wt. % to 50 wt. %, about 20 wt. % to 50 wt. %, about 30 wt. % to 50 wt. %, about 30 wt. % to 40 wt. %, or about 37 wt. % acetone. In one embodiment, the mixture of light contaminants and the one or more additional streams from earlier steps comprises about 1 wt. % to about 70 wt. %, about 1 wt. % to 60 wt. %, about 1 wt. % to 50 wt. %, about 10 wt. % to 50 wt. %, about 10 wt. % to 40 wt. %, about 10 wt. % to 30 wt. %, about 15 wt. % to 25 wt. %, or about 21 wt. % ethanol. In one embodiment, the mixture of light contaminants and the one or more additional streams from earlier steps is flowed into the bottom of the adsorption column at a flow rate of about 0.01 kg/h to 10 kg/h, about 0.01 kg/h to 8 kg/h, about 0.01 kg/h to 6 kg/h, about 0.01 kg/h to 4 kg/h, about 0.1 kg/h to 4 kg/h, about 1 kg/h to 3 kg/h, or about 2 kg/h. In one embodiment, water is added to the top of the adsorption column. In one embodiment, the water is flowed at a flow rate of about 1 kg/h to 40 kg/h, about 1 kg/h to 30 kg/h, about 1 kg/h to 20 kg/h, about 1 kg/h to 10 kg/h, about 5 kg/h to 10 kg/h, or about 7 kg/h. In one embodiment, acetone and ethanol are recovered as an aqueous solution. In some embodiments, the aqueous solution of acetone and ethanol is recycled back to the fermentation broth of step (b).

Solvent Composition

In another aspect, the present invention provides a solvent composition that is environmentally safe. In one embodiment, the solvent composition comprises a low boiling product of industrial relevance of bio-based content and low carbon footprint compared to its fossil counterpart. In another embodiment, the solvent composition is free of benzene, phenol, or aromatic compounds that are harmful to the health of human beings. In one embodiment, the solvent composition comprises a low boiling product selected from a ketone (e.g., acetone), a C3 alcohol (e.g., 1-propanol or 2-propanol), or a combination thereof. In one embodiment, the low boiling products are separated and purified by a process disclosed herein.

In one embodiment, the solvent composition comprises acetone as the low boiling point product of industrial relevance. In one embodiment, the solvent composition comprises acetone within the commercial product specification range for targeted market applications. In one embodiment, acetone has a product purity superior to about 90%, about 91%, about 92%, about 93%, about 94%, about 95%, about 96%, about 97%, about 98%, about 99%, or preferably superior to 99.5%. In another embodiment, the solvent composition comprises >99.5% purity of acetone, may comprise trace amounts of non-harmful contaminants such as ethyl acetate and ethanol, and is free of other undesired aromatic compounds such as benzene. In one embodiment, the present disclosure provides a solvent composition wherein acetone has a purity of >90%, specific gravity of about 0.78 to about 0.80, color of "Clear, Colorless," water <0.5% m/m, and distillation range of about 55.6° C. to about 56.6° C. In yet another and preferred embodiment, the present disclosure provides a solvent composition wherein acetone has a purity of >99.5%, specific gravity of about 0.7910 to about 0.7930, color of <5 ASTM Pt—Co, solids content of <1 mg/L, water <0.4% m/m, acidity of <0.002, and distillation range of about 55.6° C. to about 56.6° C.

In one embodiment, the present disclosure provides a solvent composition that can be used in numerous applications either as a direct solvent including adhesives, primers, enamels, lacquers, thinners, surface coatings, household cleaners, cosmetics (e.g., nail polish removers), and for other applications including pharmaceuticals or as a monomer building block for derivatives including isopropanol (e.g., printing inks, coatings, cleaners, enamels), hexylene glycol (e.g., ingredient in lacquers, varnishes and printing inks; intermediate for agrochemicals; detergent formulations), solketal (e.g., household cleaners, fragrances, automotive finishing), isophorone (e.g., paintings), ketals (e.g., formulations for household cleaners, coalescing agents) and polymers like BPA (e.g., polycarbonate resins for automotive systems, mobile phones and tablets, personal computers, cameras and windows and doors; electronic devices; epoxy resins), MMA and PMMA resins (e.g., automotive and construction; window glazing; disposable medical instruments such as tubing connectors and fittings, needle adapters and syringes; houseware accessories such as plates, bowls, tableware, meat platers; acrylic latexes used in wood furniture and architectural coatings), DAA (e.g., intermediate of MIBK and MIBC (or MIBCol); solvent for nitrocellulose resins, cellulose acetate resins, various oils and waxes; lacquer thinners and wood stains, household cleaners), MIBK (e.g., high-solids coatings for wood and furniture finishing; polyurethane paints and lacquers; rubber antiozonant; automotive refinishing), DIBK (e.g., solvent for coatings primarily for leather finishes; carrier for insecticides), IPDI (e.g., polyester resins, outdoor furniture coatings; automotive) and MIBC (e.g., manufacturing of ZDDP anti-wear and corrosion inhibitor additives for lube oils; flotation frother in copper ore and coal treatments).

In one embodiment, the present disclosure provides a solvent composition comprising 2-propanol as the low boiling point product of industrial relevance within the commercial specification range for targeted market applications. In one embodiment, the present disclosure provides a solvent composition comprising a bio-based 2-propanol that can be used in numerous applications including as direct solvents (e.g., surface coatings, inks, pesticides, household cleaners), intermediate for manufacturing other chemical derivatives (e.g., methyl isobutyl ketone, MIBK; methyl isobutyl carbinol, MIBC; diisobutyl ketone, DIBK, and isopropyl acetate), cosmetics (e.g., rubbing alcohols, disinfectants, cosmetics, and other personal care products), pharmaceuticals, and electronics.

In one embodiment, the present disclosure provides a solvent composition comprising 1-propanol as the low boiling point product of industrial relevance within the commercial specification range for targeted market applications. In one embodiment, the present disclosure provides a solvent composition comprising a bio-based 1-propanol that can be used in numerous applications including as direct solvents (e.g., printing, food packaging and insecticide formulations), as intermediate for manufacturing n-propyl acetate (e.g., printings and surface coatings), glycol ethers and others (e.g., flavors, fragrances, and pesticides).

In yet another embodiment, the present disclosure provides a solvent composition comprising acetone, 1-propanol, 2-propanol, ethanol, or a combination thereof. In yet another embodiment, the present disclosure provides a solvent composition comprising a mixture of acetone, 1-propanol, 2-propanol and/or ethanol in different range of concentrations and can be used in numerous market applications including as direct solvents (e.g., thinner, nail polish, nail polish remover, cleaning formulations, industrial cleaning formulations, inks).

Clauses of the Disclosure

Clause 1. A process for the isolation of one or more low boiling compounds from a fermentation broth and a fermentation off-gas, the process comprising:

(a) flowing a fermentation off-gas coming from one or more fermenters through a product recovery unit wherein the flow of the off-gas is counter to a solvent flowing through the product recovery unit and obtaining a solvent stream comprising the one or more low boiling compounds and ethanol;

(b) mixing the solvent stream of (a) with the fermentation broth and passing the resulting fermentation mixture through a first separation unit to form a high water content stream, comprising ethanol and the one or more low boiling compounds;

(c) passing the high water content stream of (b) through a second separation unit to form an intermediate water content stream, comprising ethanol and the one or more low boiling compounds;

(d) passing the ethanol intermediate water content stream of (c) through a dewatering unit to form a low water content stream; and (e) passing the low water content stream of (d) through one or more operational units, separating the ethanol and the one or more low boiling compounds.

Clause 2. The process of clause 1, wherein the fermentation broth and fermentation off-gas comprise water, the one or more low boiling compounds, ethanol, and one or more contaminants.

Clause 3. The process of clause 2, wherein the fermentation broth comprises between about 5 g/L and about 30 g/L, more preferably about 10 g/L to 20 g/L, of the one or more low boiling compounds and between about 40 g/L and about 140 g/L ethanol.

Clause 4. The process of any one of clauses 1-3, wherein the fermentation off-gas of (a) comprises one or more incondensable gases, water, ethanol, and the one or more low boiling compounds.

Clause 5. The process of clause 4, wherein the fermentation off-gas of (a) comprises about 80% w/w to about 98%, preferentially about 92% w/w to about 98% w/w, of an incondensable gas and about 0.5% w/w to about 15%, preferentially about 2% w/w to about 5% w/w, of the one or more low boiling compounds and ethanol.

Clause 6. The process of clause 4 or 5, wherein the incondensable gas is primarily carbon dioxide.

Clause 7. The process of any one of clauses 1-6, wherein the product recovery unit of (a) is an absorption column or a scrubber column.

Clause 8. The process of any one of clauses 1-7, wherein the solvent of (a) is water at a temperature of about 5° C. to about 45° C., more preferably of about 15° C. to about 35° C.

Clause 9. The process of any one of clauses 1-8, wherein the fermentation mixture of (b) is stored in a tank that is integrated with a stillage heat exchanger and the stillage heat exchanger preheats the fermentation mixture before it is passed through the first separation unit.

Clause 10. The process of any one of clauses 1-9, wherein the first separation unit is an evaporator, a distillation column, a set of distillation columns, or a combination of a centrifuge and a distillation column.

Clause 11. The process of any one of clauses 1-10, wherein the first separation unit removes an output stream comprising water, heavy components, and solids to a stillage tank.

Clause 12. The process of any one of clauses 1-11, further comprising recycling a gas stream output from the first separation unit by passing the gas stream output through steps (a) and (b).

Clause 13. The process of clause 12, wherein the gas stream output comprises an incondensable gas which is removed as the gas stream is passed through steps (a) and (b) and wherein the gas stream further comprises the one or more low boiling compounds and ethanol which are recovered.

Clause 14. The process of clause 12 or 13, wherein the gas stream output comprises about 20% w/w to about 95% w/w, preferentially about 40% w/w to about 85% w/w, of an incondensable gas and about 1% w/w to about 75% w/w, preferentially about 15% w/w to about 60% w/w, of the one or more low boiling compounds and ethanol.

Clause 15. The process of any one of clauses 1-14, wherein the second separation unit of (c) is a rectifier column.

Clause 16. The process of any one of clauses 1-15, wherein the second separation unit of (c) removes a bottom output stream comprising primarily water and a side output stream comprising fusel oil.

Clause 17. The process of clause 16, further comprising: recycling the bottom output stream of (c) to an upstream fermentation process which produces the fermentation broth; or recycling the bottom output stream of (c) by passing the bottom output stream through steps (b) and (c).

Clause 18. The process of any one of clauses 1-17, wherein the intermediate water content stream of (c) comprises ethanol, water, and the one or more low boiling compounds.

Clause 19. The process of any one of clauses 1-18, wherein the intermediate water content stream of (c) comprises one or more high boiling compounds, in negligible amounts, that were present in the fermentation broth or a raw material from which the fermentation broth is obtained.

Clause 20. The process of clause 18 or 19, wherein the intermediate water content stream of (c) comprises about 75% w/w to about 95% w/w ethanol, about 5% w/w to about 10% w/w water, and about 1% w/w to about 15% w/w of the one or more low boiling compounds.

Clause 21. The process of any one of clauses 1-20, wherein the dewatering unit of (d) is a membrane separation system or a molecular sieve system.

Clause 22. The process of any one of clauses 1-21, wherein the low water content stream of (d) comprises less than about 2.5% w/w water or between about 0.5% w/w to about 2.5% w/w water.

Clause 23. The process of any one of clauses 1-22, further comprising recycling water removed by the dewatering unit of (d) by passing the removed water through steps (c) and (d).

Clause 24. The process of any one of clauses 1-23, wherein the one or more low boiling compounds are selected from a C3 alcohol, a C3 ketone, or a combination thereof.

Clause 25. The process of any one of clauses 1-24, wherein the one or more low boiling compounds are selected from 1-propanol, 2-propanol, acetone, or a combination thereof.

Clause 26. The process of any one of clauses 1-25, wherein the fermentation broth comprises C4 alcohols at a negligible amount compared to the amount of ethanol and the one or more low boiling compounds such that the amount of C4 alcohols does not justify their purification as target products.

Clause 27. The process of clause 26, wherein the C4 alcohol is 1-butanol, 2-butanol, or a combination thereof.

Clause 28. The process of any one of clauses 1-27, wherein the low boiling compound is acetone and the one or more operational units of (e) is a pervaporation system, a single distillation column, a sequence of distillation columns, a vacuum column, or a combination thereof, which separates the ethanol from the acetone.

Clause 29. The process of clause 28, wherein the pervaporation system, the single distillation column, the sequence of distillation columns, the vacuum column, or the combination thereof of (e) each independently optionally comprise a heat exchanger or a reboiler that can be heat integrated with the second separation unit of (c) or with any other process unit that has proper heat available.

Clause 30. The process of any one of clauses 1-27, wherein the low boiling compounds are acetone and 1-propanol and the one or more operational units of (e) are:
    (i) a first distillation system which separates 1-propanol from a mixture comprising ethanol and acetone,
    (ii) a second distillation system which purifies the 1-propanol from (i) to a desired purity, and
    (iii) a third distillation system which separates the mixture of (i) into ethanol and acetone to a desired purity.

Clause 31. The process of clause 30, wherein distillation systems (i) and (iii) each independently optionally comprise a reboiler that can be heat integrated with the second separation unit of (c) or with any other process unit that has proper heat available.

Clause 32. The process of any one of clauses 1-27, wherein the low boiling compounds are 1-propanol and 2-propanol and the one or more operational units of (e) are:
    (i) one or more distillation columns which separate 1-propanol from a mixture comprising ethanol and 2-propanol,
    (ii) an extractive distillation unit which uses a solvent to extract 2-propanol from a vapor phase mixture comprising ethanol and 2-propanol while obtaining a first fraction of ethanol at a desired purity and a second fraction comprising solvent, 2-propanol, and ethanol,
    (iii) one or more distillation columns which separate the second fraction of (ii) into solvent and a mixture of ethanol and 2-propanol, and
    (iv) one or more distillation columns which separate 2-propanol at a desired purity from the mixture of (iii), leaving a solution of primarily ethanol with 2-propanol, wherein the operational units (ii) to (iv) can be replaced with a system comprising two distillation columns operating under vacuum conditions.

Clause 33. The process of clause 32, further comprising recycling the solvent of (iii) for use in the extractive distillation unit of (ii).

Clause 34. The process of clause 32 or 33, further comprising: recycling the solution of (iv) by heating the solution to form a vapor and passing the vapor through the extractive distillation unit of (ii); or
    recycling the solution of (iv) by passing the solution through the extractive distillation unit of (ii).

Clause 35. The process of any one of clauses 32-34, wherein:
    distillation columns (i) and (iv) each independently optionally comprise a reboiler that can be heat integrated with the second separation unit of (c), the extractive distillation unit of (ii), a combination thereof, or with any other process unit that has proper heat available; or operational units (ii), (iii), and (iv) are replaced by two distillation columns operating under vacuum conditions which each independently optionally comprise a reboiler that can be heat integrated with a condenser of (c), a condenser of (i), or a combination thereof.

Clause 36. The process of any one of clauses 1-27, wherein the low boiling compound is 2-propanol and the one or more operational units of (e) comprise:
    (i) an extractive distillation unit which uses a solvent to extract 2-propanol from a vapor phase mixture comprising ethanol and 2-propanol while obtaining a first fraction of ethanol at a desired purity and a second fraction comprising solvent, 2-propanol, and ethanol,
    (ii) one or more distillation columns which separate the second fraction of (i) into solvent and a mixture of ethanol and 2-propanol, and
    (iii) one or more distillation columns which separate 2-propanol at a desired purity from the mixture of (ii), leaving a solution of primarily ethanol with 2-propanol, wherein the operational units (i) to (iii) can be replaced with a system comprising two distillation columns operating under vacuum conditions.

Clause 37. The process of clause 36, further comprising recycling the solvent of (ii) for use in the extractive distillation unit of (i).

Clause 38. The process of clause 36 or 37, further comprising: recycling the solution of (iii) by heating the solution to form a vapor and passing the vapor through the extractive distillation unit of (i); or recycling the solution of (iii) by passing the solution through the extractive distillation unit of (i).

Clause 39. The process of any one of clauses 36-38, wherein:

distillation column (iii) comprises a reboiler that is optionally heat integrated with the extractive distillation unit of (i) or with any other process unit that has proper heat available; or operational units (i), (ii), and (iii) are replaced by two distillation columns under vacuum conditions which each independently optionally comprise a reboiler that can be heat integrated with a condenser of (c).

Clause 40. The process of any one of clauses 1-39, wherein the fermentation broth is obtained by a process comprising: contacting a fermentable carbon source with an ethanol-producing yeast in a fermentation medium; and fermenting the carbon source by the yeast in the fermentation medium, to produce a fermentation broth and a fermentation off-gas comprising ethanol and the one or more low boiling compounds.

Clause 41. The process of clause 40, wherein ethanol is produced at a greater concentration in mg/mL than the one or more low boiling compounds.

Clause 42. The process of clause 40 or 41, wherein the carbon source is a C5 sugar, a C6 sugar, or a C12 sugar.

Clause 43. The process of any one of clauses 40-42, wherein the carbon source is derived from a renewable source used in an ethanol mill.

Clause 44. The process of clause 43, wherein the carbon source is derived from sugarcane, corn, cellulose, beets, biomass, or biomass waste.

Clause 45. The process of any one of clauses 40-44, wherein the ethanol-producing yeast is a genetically modified *Saccharomyces cerevisiae*.

Clause 46. The process of any one of clauses 40-45, wherein the ethanol-producing yeast produces greater than about 40 g/L, about 60 g/L, about 80 g/L, about 100 g/L, about 120 g/L, about 140 g/L of ethanol after fermentation for less than about 72 hours, about 60 hours, about 55 hours, about 50 hours, about 10 hours, or about 5 hours at an industrial scale.

Clause 47. The process of any one of clauses 40-46, wherein the ethanol-producing yeast produces greater than about 1 g/L, about 3 g/L, about 5 g/L, about 10 g/L, about 15 g/L or about 30 g/L of the one or more low boiling compounds after fermentation for less than about 72 hours, about 60 hours, about 55 hours, about 50 hours, about 10 hours, or about 5 at an industrial scale.

Clause 48. The process of any one of clauses 40-47, wherein the ethanol-producing yeast produces greater than about 1 g/L, about 3 g/L, about 5 g/L, about 10 g/L, about 15 g/L or about 30 g/L of the one or more low boiling compounds after fermentation for less than about 72 hours, about 60 hours, about 55 hours, or about 10 hours, or about 5 hours at an industrial scale.

Clause 49. The process of any one of clauses 40-48, wherein the low boiling compounds have, at a standard pressure of 100 kPa (1 bar), a boiling point of less than about 100° C., about 99° C., about 98° C., about 97° C., about 95° C., about 90° C., about 85° C., about 80° C., about 75° C., about 70° C., about 65° C., or about 60° C.

Clause 50. The process of any one of clauses 40-49, wherein the one or more low boiling compounds are selected from a C3 alcohol, a C3 ketone, or a combination thereof.

Clause 51. The process of any one of clauses 40-50, wherein the one or more low boiling compounds are selected from 1-propanol, 2-propanol, acetone, or a combination thereof.

Clause 52. The process of any one of clauses 40-51, wherein the yeast produces negligible amounts of C4 compounds in comparison to ethanol.

Clause 53. The process of any one of clauses 40-52, wherein the yeast does not produce 1-butanol and 2-butanol or produces 1-butanol and 2-butanol at a negligible amount compared to the amount of ethanol and the one or more low boiling compounds.

Clause 54. A process for the production and isolation of ethanol and one or more low boiling compounds, the process comprising:

(a) contacting a fermentable carbon source with an ethanol-producing yeast in a fermentation medium;

(b) fermenting the carbon source by the yeast in the fermentation medium of (a) to produce a fermentation broth and a fermentation off-gas comprising ethanol and the one or more low boiling compounds;

(c) flowing a fermentation off-gas coming from one or more fermenters in (b) through a product recovery unit wherein the flow of the off-gas is counter to a solvent flowing through the product recovery unit and obtaining a solvent stream comprising the one or more low boiling compounds and ethanol;

(d) mixing the solvent stream of (c) with the fermentation broth and passing the resulting fermentation mixture through a first separation unit to form a high water content stream comprising ethanol and the one or more low boiling compounds;

(e) passing the high water content stream of (d) through a second separation unit to form an intermediate water content stream comprising ethanol and the one or more low boiling compounds;

(f) passing the intermediate water content stream of (e) through a dewatering unit to form a low water content stream; and (g) passing the low water content stream of (f) through one or more operational units, separating the ethanol and the one or more low boiling compounds.

Clause 55. A solvent composition substantially free of aromatic compounds harmful to human health, the composition comprising one or more low boiling compounds isolated by the process of any one of clauses 1-54.

Clause 56. The solvent composition of clause 55, wherein the one or more low boiling compounds comprise acetone, 1-propanol, 2-propanol, or a combination thereof.

Clause 57. The solvent composition of clause 55 or 56, wherein the composition is substantially free of benzene, phenol, or a combination thereof.

Clause 101. A process for the isolation of one or more low boiling compounds from a fermentation broth and a fermentation off-gas, the process comprising:

(a) flowing a fermentation off-gas coming from one or more fermenters through a product recovery unit wherein the flow of the off-gas is counter to a solvent flowing through the product recovery unit and obtaining a solvent stream comprising the one or more low boiling compounds and ethanol;

(b) mixing the solvent stream of (a) with the fermentation broth and passing the resulting fermentation mixture through a first separation unit to form a high water content stream, comprising ethanol and the one or more low boiling compounds;

(c) passing the high water content stream of (b) through a second separation unit to form an intermediate water content stream, comprising ethanol and the one or more low boiling compounds;

(d) passing the ethanol intermediate water content stream of (c) through a dewatering unit to form a low water content stream; and (e) passing the low water content stream of (d) through one or more operational units, separating the ethanol and the one or more low boiling compounds.

Clause 102. The process of clause 101, wherein the fermentation broth and fermentation off-gas comprise water, the one or more low boiling compounds, ethanol, and one or more contaminants.

Clause 103. The process of clause 102, wherein the fermentation broth comprises between about 5 g/L and about 30 g/L, more preferably about 10 g/L to 20 g/L, of the one or more low boiling compounds and between about 40 g/L and about 140 g/L ethanol.

Clause 104. The process of any one of clauses 101-103, wherein the fermentation off-gas of (a) comprises one or more incondensable gases, water, ethanol, and the one or more low boiling compounds.

Clause 105. The process of clause 104, wherein the fermentation off-gas of (a) comprises about 80% w/w to about 98%, preferentially about 92% w/w to about 98% w/w, of an incondensable gas and about 0.5% w/w to about 15%, preferentially about 2% w/w to about 5% w/w, of the one or more low boiling compounds and ethanol.

Clause 106. The process of clause 104 or 105, wherein the incondensable gas is primarily carbon dioxide.

Clause 107. The process of any one of clauses 101-106, wherein the product recovery unit of (a) is an absorption column or a scrubber column.

Clause 108. The process of any one of clauses 101-107, wherein the solvent of (a) is water at a temperature of about 5° C. to about 45° C., more preferably of about 15° C. to about 35° C.

Clause 109. The process of any one of clauses 101-108, wherein the fermentation mixture of (b) is stored in a tank that is integrated with a stillage heat exchanger and the stillage heat exchanger preheats the fermentation mixture before it is passed through the first separation unit.

Clause 110. The process of any one of clauses 101-109, wherein the first separation unit is an evaporator, a distillation column, a set of distillation columns, or a combination of a centrifuge and a distillation column.

Clause 111. The process of any one of clauses 101-110, wherein the first separation unit removes an output stream comprising water, heavy components, and solids to a stillage tank.

Clause 112. The process of any one of clauses 101-111, further comprising recycling a gas stream output from the first separation unit by passing the gas stream output through steps (a) and (b).

Clause 113. The process of clause 112, wherein the gas stream output comprises an incondensable gas which is removed as the gas stream is passed through steps (a) and (b) and wherein the gas stream further comprises the one or more low boiling compounds and ethanol which are recovered.

Clause 114. The process of clause 112 or 113, wherein the gas stream output comprises about 20% w/w to about 95% w/w, preferentially about 40% w/w to about 85% w/w, of an incondensable gas and about 1% w/w to about 75% w/w, preferentially about 15% w/w to about 60% w/w, of the one or more low boiling compounds and ethanol.

Clause 115. The process of any one of clauses 101-114, wherein the second separation unit of (c) is a rectifier column, a distillation column, or a set of distillation columns.

Clause 116. The process of any one of clauses 101-115, wherein the second separation unit of (c) removes a bottom output stream comprising primarily water and a side output stream comprising fusel oil.

Clause 117. The process of clause 116, further comprising:

recycling the bottom output stream of (c) to an upstream fermentation process which produces the fermentation broth;

recycling the bottom output stream of (c) by passing the bottom output stream through step (c); or recycling the bottom output stream of (c) by passing the bottom output stream through steps (b) and (c).

Clause 118. The process of any one of clauses 101-117, wherein the intermediate water content stream of (c) comprises ethanol, water, and the one or more low boiling compounds.

Clause 119. The process of any one of clauses 101-118, wherein the intermediate water content stream of (c) comprises one or more high boiling compounds, in negligible amounts, that were present in the fermentation broth or a raw material from which the fermentation broth is obtained.

Clause 120. The process of clause 118 or 119, wherein the intermediate water content stream of (c) comprises about 75% w/w to about 95% w/w ethanol, about 5% w/w to about 10% w/w water, and about 1% w/w to about 15% w/w of the one or more low boiling compounds.

Clause 121. The process of any one of clauses 101-120, further comprising removing a top vapor stream from the second separation unit of (c) and recycling the top vapor stream by combining the top vapor stream with the fermentation off-gas and passing the combined stream through steps (a), (b), and (c).

Clause 122. The process of any one of clauses 101-121, wherein the dewatering unit of (d) is a membrane separation system or a molecular sieve system.

Clause 123. The process of any one of clauses 101-122, wherein the low water content stream of (d) comprises less than about 2.5% w/w water or between about 0.5% w/w to about 2.5% w/w water.

Clause 124. The process of any one of clauses 101-123, further comprising recycling water removed by the dewatering unit of (d) by passing the removed water through steps (c) and (d).

Clause 125. The process of any one of clauses 101-124, further comprising removing a top vapor stream from the dewatering unit of (d) and recycling the top vapor stream by combining the top vapor stream with the fermentation off-gas and passing the combined stream through steps (a), (b), (c), and (d).

Clause 126. The process of any one of clauses 101-125, wherein the one or more low boiling compounds are selected from a C3 alcohol, a C3 ketone, or a combination thereof.

Clause 127. The process of any one of clauses 101-126, wherein the one or more low boiling compounds are selected from 1-propanol, 2-propanol, acetone, or a combination thereof.

Clause 128. The process of any one of clauses 101-127, wherein the fermentation broth comprises C4 alcohols at a negligible amount compared to the amount of ethanol and the one or more low boiling compounds such that the amount of C4 alcohols does not justify their purification as target products.

Clause 129. The process of clause 128, wherein the C4 alcohol is 1-butanol, 2-butanol, or a combination thereof.

Clause 130. The process of any one of clauses 101-129, wherein the low boiling compound is acetone and the one or more operational units of (e) is a pervaporation system, a single distillation column, a sequence of distillation columns, a vacuum column, or a combination thereof, which separates the ethanol from the acetone.

Clause 131. The process of clause 130, wherein the pervaporation system, the single distillation column, the sequence of distillation columns, the vacuum column, or the combination thereof of (e) each independently optionally comprise a heat exchanger or a reboiler that can be heat integrated with the second separation unit of (c) or with any other process unit that has proper heat available.

Clause 132. The process of clause 130 or 131, wherein the one or more operational units of (e) further separate a contaminant stream.

Clause 133. The process of clause 132, wherein the contaminant stream comprises acetaldehyde and acetone.

Clause 134. The process of clause 132 or 133, further comprising combining the contaminant stream with one or more side streams from steps (b), (c), and/or (d), wherein the one or more side streams comprise contaminants, ethanol, and/or acetone.

Clause 135. The process of clause 134, further comprising passing the combined stream through an adsorption column to recover the ethanol and/or the acetone.

Clause 136. The process of clause 135, further comprising passing the recovered acetone and/or ethanol through steps (b), (c), (d), and (e) to purify the recovered acetone and/or ethanol to a desired purity.

Clause 137. The process of any one of clauses 101-129, wherein the low boiling compounds are acetone and 1-propanol and the one or more operational units of (e) are:
   (i) a first distillation system which separates 1-propanol from a mixture comprising ethanol and acetone,
   (ii) a second distillation system which purifies the 1-propanol from (i) to a desired purity, and
   (iii) a third distillation system which separates the mixture of (i) into ethanol and acetone to a desired purity.

Clause 138. The process of clause 137, wherein distillation systems (i) and (iii) each independently optionally comprise a reboiler that can be heat integrated with the second separation unit of (c) or with any other process unit that has proper heat available.

Clause 139. The process of clause 137 or 138, wherein the acetone separated in distillation system (iii) comprises one or more contaminants and the one or more operational units of (e) further comprise (iv) a fourth distillation system which separates the acetone from the one or more contaminants.

Clause 140. The process of clause 139, wherein the one or more contaminants comprise acetaldehyde.

Clause 141. The process of clause 139 or 140, wherein the one or more contaminants further comprise one or more desired products selected from ethanol and acetone, and the process further comprises passing the one or more contaminants through steps (a), (b), (c), (d), and (e) to obtain the one or more desired products.

Clause 142. The process of clause 139 or 140, wherein the one or more contaminants further comprise one or more desired products selected from ethanol, acetone, and 1-propanol and the process further comprises feeding the one or more contaminants into a scrubber and recovering the one or more desired products by adsorption with a solvent.

Clause 143. The process of clause 142, wherein the one or more contaminants are also adsorbed by the solvent and the process further comprises passing the solvent through steps (b), (c), (d), and (e) to obtain the one or more desired products.

Clause 144. The process of clause 142 or 143, further comprising feeding one or more vapor streams from steps (a), (d), or (e) into the scrubber.

Clause 145. The process of any one of clauses 101-129, wherein the low boiling compounds are 1-propanol and 2-propanol and the one or more operational units of (e) are:
   (i) one or more distillation columns which separate 1-propanol from a mixture comprising ethanol and 2-propanol,
   (ii) an extractive distillation unit which uses a solvent to extract 2-propanol from a vapor phase mixture comprising ethanol and 2-propanol while obtaining a first fraction of ethanol at a desired purity and a second fraction comprising solvent, 2-propanol, and ethanol,
   (iii) one or more distillation columns which separate the second fraction of (ii) into solvent and a mixture of ethanol and 2-propanol, and
   (iv) one or more distillation columns which separate 2-propanol at a desired purity from the mixture of (iii), leaving a solution of primarily ethanol with 2-propanol, wherein the operational units (ii) to (iv) can be replaced with a system comprising two distillation columns operating under vacuum conditions.

Clause 146. The process of clause 145, further comprising recycling the solvent of (iii) for use in the extractive distillation unit of (ii).

Clause 147. The process of clause 145 or 146, further comprising: recycling the solution of (iv) by heating the solution to form a vapor and passing the vapor through the extractive distillation unit of (ii); or recycling the solution of (iv) by passing the solution through the extractive distillation unit of (ii).

Clause 148. The process of any one of clauses 145-147, wherein:
   distillation columns (i) and (iv) each independently optionally comprise a reboiler that can be heat integrated with the second separation unit of (c), the extractive distillation unit of (ii), a combination thereof, or with any other process unit that has proper heat available; or
   operational units (ii), (iii), and (iv) are replaced by two distillation columns operating under vacuum conditions which each independently optionally comprise a reboiler that can be heat integrated with a condenser of (c), a condenser of (i), or a combination thereof.

Clause 149. The process of any one of clauses 101-129, wherein the low boiling compound is 2-propanol and the one or more operational units of (e) comprise:
   (i) an extractive distillation unit which uses a solvent to extract 2-propanol from a vapor phase mixture comprising ethanol and 2-propanol while obtaining a first fraction of ethanol at a desired purity and a second fraction comprising solvent, 2-propanol, and ethanol,
   (ii) one or more distillation columns which separate the second fraction of (i) into solvent and a mixture of ethanol and 2-propanol, and
   (iii) one or more distillation columns which separate 2-propanol at a desired purity from the mixture of (ii), leaving a solution of primarily ethanol with 2-propanol, wherein the operational units (i) to (iii) can be replaced with a system comprising two distillation columns operating under vacuum conditions.

Clause 150. The process of clause 149, further comprising recycling the solvent of (ii) for use in the extractive distillation unit of (i).

Clause 151. The process of clause 149 or 150, further comprising: recycling the solution of (iii) by heating the solution to form a vapor and passing the vapor through the extractive distillation unit of (i); or recycling the solution of (iii) by passing the solution through the extractive distillation unit of (i).

Clause 152. The process of any one of clauses 149-151, wherein:

distillation column (iii) comprises a reboiler that is optionally heat integrated with the extractive distillation unit of (i) or with any other process unit that has proper heat available; or operational units (i), (ii), and (iii) are replaced by two distillation columns under vacuum conditions which each independently optionally comprise a reboiler that can be heat integrated with a condenser of (c).

Clause 153. The process of any one of clauses 101-152, wherein the fermentation broth is obtained by a process comprising:

contacting a fermentable carbon source with an ethanol-producing yeast in a fermentation medium; and fermenting the carbon source by the yeast in the fermentation medium, to produce a fermentation broth and a fermentation off-gas comprising ethanol and the one or more low boiling compounds.

Clause 154. The process of clause 153, wherein ethanol is produced at a greater concentration in mg/mL than the one or more low boiling compounds.

Clause 155. The process of clause 153 or 154, wherein the carbon source is a C5 sugar, a C6 sugar, or a C12 sugar.

Clause 156. The process of any one of clauses 153-155, wherein the carbon source is derived from a renewable source used in an ethanol mill.

Clause 157. The process of clause 156, wherein the carbon source is derived from sugarcane, corn, cellulose, beets, biomass, or biomass waste.

Clause 158. The process of any one of clauses 153-157, wherein the ethanol-producing yeast is a genetically modified *Saccharomyces cerevisiae*.

Clause 159. The process of any one of clauses 153-158, wherein the ethanol-producing yeast produces greater than about 40 g/L, about 60 g/L, about 80 g/L, about 100 g/L, about 120 g/L, about 140 g/L of ethanol after fermentation for less than about 72 hours, about 60 hours, about 55 hours, about 50 hours, about 10 hours, or about 5 hours at an industrial scale.

Clause 160. The process of any one of clauses 153-159, wherein the ethanol-producing yeast produces greater than about 1 g/L, about 3 g/L, about 5 g/L, about 10 g/L, about 15 g/L or about 30 g/L of the one or more low boiling compounds after fermentation for less than about 72 hours, about 60 hours, about 55 hours, about 50 hours, about 10 hours, or about 5 at an industrial scale.

Clause 161. The process of any one of clauses 153-160, wherein the ethanol-producing yeast produces greater than about 1 g/L, about 3 g/L, about 5 g/L, about 10 g/L, about 15 g/L or about 30 g/L of the one or more low boiling compounds after fermentation for less than about 72 hours, about 60 hours, about 55 hours, or about 10 hours, or about 5 hours at an industrial scale.

Clause 162. The process of any one of clauses 153-161, wherein the low boiling compounds have, at a standard pressure of 100 kPa (1 bar), a boiling point of less than about 100° C., about 99° C., about 98° C., about 97° C., about 95°

C., about 90° C., about 85° C., about 80° C., about 75° C., about 70° C., about 65° C., or about 60° C.

Clause 163. The process of any one of clauses 153-162, wherein the one or more low boiling compounds are selected from a C3 alcohol, a C3 ketone, or a combination thereof.

Clause 164. The process of any one of clauses 153-163, wherein the one or more low boiling compounds are selected from 1-propanol, 2-propanol, acetone, or a combination thereof.

Clause 165. The process of any one of clauses 153-164, wherein the yeast produces negligible amounts of C4 compounds in comparison to ethanol.

Clause 166. The process of any one of clauses 153-165, wherein the yeast does not produce 1-butanol and 2-butanol or produces 1-butanol and 2-butanol at a negligible amount compared to the amount of ethanol and the one or more low boiling compounds.

Clause 167. A process for the production and isolation of ethanol and one or more low boiling compounds, the process comprising:

(a) contacting a fermentable carbon source with an ethanol-producing yeast in a fermentation medium;

(b) fermenting the carbon source by the yeast in the fermentation medium of (a) to produce a fermentation broth and a fermentation off-gas comprising ethanol and the one or more low boiling compounds;

(c) flowing a fermentation off-gas coming from one or more fermenters in (b) through a product recovery unit wherein the flow of the off-gas is counter to a solvent flowing through the product recovery unit and obtaining a solvent stream comprising the one or more low boiling compounds and ethanol;

(d) mixing the solvent stream of (c) with the fermentation broth and passing the resulting fermentation mixture through a first separation unit to form a high water content stream comprising ethanol and the one or more low boiling compounds;

(e) passing the high water content stream of (d) through a second separation unit to form an intermediate water content stream comprising ethanol and the one or more low boiling compounds;

(f) passing the intermediate water content stream of (e) through a dewatering unit to form a low water content stream; and (g) passing the low water content stream of (f) through one or more operational units, separating the ethanol and the one or more low boiling compounds.

Clause 168. A solvent composition substantially free of aromatic compounds harmful to human health, the composition comprising one or more low boiling compounds isolated by the process of any one of clauses 101-167.

Clause 169. The solvent composition of clause 168, wherein the one or more low boiling compounds comprise acetone, 1-propanol, 2-propanol, or a combination thereof.

Clause 170. The solvent composition of clause 168 or 169, wherein the composition is substantially free of benzene, phenol, or a combination thereof.

EXAMPLES

Example 1: Process for the Recovery of Low-Boiling Point Component(s) from an Ethanol Stream The present disclosure relates to a novel downstream configuration for the cost-efficient and/or energy-efficient production and recovery of low-boiling point compound(s), including ketones and alcohols, from an ethanol strain of industrial sugar-ethanol production processes. In some aspects, the low boiling point compound(s) are recovered from a diluted stream with ethanol at higher relative concentrations, enabling the low boiling compound(s) to be obtained from the new and unique fermentation composition—with limited (negligible) impact or preferably without impacting—the ethanol, DDGS, and oil specifications. In some embodiments, the equipment disclosed herein used to obtain such ketones and alcohols is energetically integrated with the traditional industrial ethanol production and separation assets (e.g. by heat integration between rectification column and specification column). In some embodiments, the process disclosed herein may be particularly used to recover acetone, 1-propanol, and 2-propanol from an ethanol stream in the industrial production of ethanol derived from corn, sugarcane, sugar beets, and sorghum. In some embodiments, the disclosed process can be applied to an existing ethanol producing facility while maintaining most of the existing equipment, adding only the downstream separation, utilities, and storage equipment while generating new commercially relevant products. In some embodiments, there will be the necessity of additional equipment in the fermentation area. The ethanol stream comprising a mixture of ethanol, water, congeners (or contaminants e.g., acetaldehyde, methanol, and others) and the low boiling compound(s) results from a sugar-fermentation process using a unique genetically modified yeast that was developed and used industrially. The process disclosed herein leverages industrial ethanol fermentation and distillation assets, reducing the capital investment to what is needed for the separation and purification of the low boiling compound(s) from an ethanol stream. The limited capital investment increases the cost-competitiveness of the target low boiling compound(s).

The low-boiling point components described herein have a lower boiling point than water at standard atmosphere conditions. For example, acetone, 1-propanol, and 2-propanol have a lower boiling point (56° C., 97° C. and 82.5° C., respectively) compared to water (100° C.) at standard atmospheric pressure conditions. A high boiling point product has a higher boiling point than water at standard atmosphere conditions. For example, 1-butanol and 2-butanol are molecules with higher boiling point (117.7° C.) than water at standard atmospheric pressure conditions.

The present disclosure further relates to a novel process to enable the production and recovery of acetone from sugar fermentation bioreactors producing ethanol, delivering a low-cost acetone free of phenol and phthalate traces. The most common method to produce petrochemical acetone is directly or indirectly from propylene. More than 80% of global petrochemical acetone is produced via the cumene process, and as a result, the production of acetone is tied to the production of phenol. In the petrochemical production of acetone via the cumene process, benzene is alkylated with propylene producing cumene, which is further oxidized by air to produce phenol and acetone. Therefore, the petrochemical acetone has traces of the phenol, which is an undesirable product due to its toxicity effect to human beings and to the environment. Instead, the present disclosure described relates to the production of a bio-based acetone free of phenol traces, and so more eco-friendly.

The present disclosure is directed to the efficient recovery of low boiling compounds by reducing the product losses due to the recycling points in the process, including but not limited to, the recovery of off-gas from fermenters and vapors from the beer column, and streams from the molecular sieve operation. The low boiling compounds of interest are of high volatility and are produced and present in both fermentation broth and off-gas. Aiming to recover the low boiling compounds from the off-gas phase, the gas stream needs to flow inside a product recovery unit, for example an absorption column or preferably a scrubber column. The off-gas flows in counter current with a solvent, preferably water, in a proportion of 14 to 8 parts of water for one part of off-gas in a mole basis, or 0.5 to 5 parts of water for one part of off-gas in a mass basis. This water stream absorbs the low-boiling compounds and will be recycled back to the fermentation broth in a tank. This mixture, typically called beer, will be introduced in the beer column but will exchange heat with the stillage exiting the bottom of this column making the process energetically integrated what represents reduction in cost with steam and heat. The top of this column will be recycled to recover the products and, a side stream will pass through different processes depending on the target low-boiling point compounds.

This present disclosure also relates to a novel downstream process for the separation and purification of low boiling chemicals such as acetone, 1-propanol, and 2-propanol, in particular wherein the side stream of the beer column needs to be almost completely dewatered from 0 to 1% w/w of water content. In some embodiments wherein a low water content side stream is needed, a molecular sieve or other drying (also known as de-watering) technology is used as a key step for the implementation of the claimed process in a corn-ethanol mill. Specifically, disclosed herein is a novel process design for a more energy efficient separation and purification of low boiling products—such as acetone— from industrial corn-ethanol fermentation bioreactors, wherein all or part of the heat required in the specification column to separate and purify the low-boiling products from an ethanol stream in some embodiments can come from the vapor stream generated at the top of the rectification column of the industrial corn-ethanol plant, reducing additional costs with steam by providing already available heat for obtaining the low-boiling products.

In the industrial corn-ethanol production, the traditional dry-grind process grinds the whole corn kernel and mixes it with water and enzymes. The mash is then cooked to liquefy the starch further. The mash is then cooled and mixed with more enzymes to convert the remaining sugar polymers to the available glucose before fermenting it into ethanol. The components of the kernel not fermented include the germ, fiber, and protein, and are concentrated in the distillers dried grains that are produced as co-products. This method is relatively cost effective and requires less equipment than wet milling, which separates the fiber, germ (oil), and protein from the starch before it is fermented into ethanol. The main products of dry milling are ethanol, $CO_2$, and dried distiller grain with solubles (DDGS). The six key process steps are: 1) grinding, 2) cooking and liquefaction, 3) saccharification, 4) fermentation, 5) distillation, and 6) de-watering.

After the sugar fermentation by the yeast, the resulting "beer," a dilute aqueous mixture of ethanol, congeners, residual sugars, proteins, and mash solids is concentrated via distillation. Congeners may include, but are not limited to, aldehydes (e.g. acetaldehyde), ketones (e.g. acetone and diacetyl), esters (e.g. ethyl formate, ethyl acetate, propyl acetate, 2-methylpropyl acetate, 3-methylbutyl acetate, ethyl hexanoate, hexyl acetate, ethyl lactate, 2-methylpropyl hexanoate, ethyl lactate, 2-methylpropyl hexanoate, ethyl octanoate, 3-methylbutyl hexanoate, ethyl phenylacetate, phenyl ethyl acetate, ethyl decanoate, ethyl dodecanoate, and ethyl tetradecanoate), alcohols (e.g. methanol, 2-propanol, 1-propanol, 2-methylbutan-1-ol, 3-methylbutan-1-ol, 1-pentanol, 2-phenylethan-1-ol, and glycerol), and organic acids (e.g. acetic acid, lactic acid, propionic acid, i-butyric acid, butyric acid, valeric acid, i-valeric acid, hexanoic acid, octanoic acid, decanoic acid, and dodecanoric acid). Several flow schemes exist, generally containing beer/mash columns and rectifier/stripper columns. The beer column is usually a reboiled stripper that takes the so-called beer and strips out a stream containing the ethanol and the volatile byproducts in the overhead or as a side stream. This step also removes water, heavy components, and solids at the bottom of the column, with product loss limited to low levels at the so-called stillage. The stillage can have different end uses, according to the feedstock selected. The stripped ethanol from the beer column is concentrated in a distillation tower, or often two separate towers that perform rectification and stripping separately. The overhead product approaches the ethanol/water azeotrope concentration, with approximately 5% water. Final dehydration beyond the azeotropic concentration is typically done using molecular sieves.

As one of the novel aspects of this disclosure is the production, separation, and purification of low-boiling products from a stream of ethanol, it is expected that at the top or side stream of the rectification column there will be, in addition to ethanol in greater amounts, the target low-boiling products (co-products with ethanol) such as acetone, iso-propanol, and/or other molecules less volatile than water. Therefore, additional equipment is needed in the pre-existing ethanol plant to separate and purify the target low-boiling products from ethanol. The add-on equipment, in this case, is called the specification column. The specification column receives the ethanol plus acetone (or any other product with a boiling point equal or lower than water) mixture from the top of the rectification column. Acetone (or any other product with a boiling point equal or lower than water) can be specified as a side product in this specification column, with incondensable gases leaving at the top, and purified ethanol at bottom. The condenser of rectification column can be heat integrated with the reboiler of the specification column. This heat integration can minimize or eliminate the amount of additional steam needed for additional equipment, making the process more cost efficient when compared to other process for the synthesis of biobased acetone, such as the ABE process.

The add-on equipment is a single distillation column suitable for the recovery of the low-boiling point compound of interest from the ethanol stream. In some embodiments, the process design is further customized to recover the low-boiling point compound(s) of interest from ethanol stream, wherein the add-on equipment is one or more distillation columns. The presence of congeners in the ethanol stream alongside with ethanol and the low-boiling point compound(s) of interest may require a sequential distillation equipment (more than one specification column) to enable the recovery of the low-boiling point compound(s) of interest in the desired market specification.

There are more recent, but still exploratory, bio-based ABE processes being proposed aiming to alleviate the butanol inhibition to *Clostridium* cells by using techniques coupling both fermentation and separation (liquid extraction, adsorption, stripping, etc.) processes, simultaneously. This means that butanol could be recovered as it is produced, reducing the energy requirement for distillation of a final, extremely diluted fermentation broth. However, the process disclosed herein provides a more cost-effective process for the production, separation, and purification of low-boiling products from a different and new fermentation composition free of butanol or with butanol at negligible amounts, wherein a novel engineered ethanol yeast strain is used to produce ethanol as the main product with the low-boiling product(s) by leveraging existing industrial ethanol fermentation and distillation processes, as well as using add-on equipment that can be energetically integrated with the pre-existing heat exchangers aiming to separate and purify such low-boiling products from an ethanol stream.

Therefore, the present disclosure invention provides a novel process design, alternative to existing ones, for the lower-cost production, separation, and purification of low-boiling products including, but not restricted to, acetone from an ethanol stream. The novel process design is effective, simple, and has reduced capital expenses and optimized operating expenses, thus increasing its cost-competitiveness and the potential that it is adopted by industrial ethanol millers to diversify their products portfolio and maximize profits.

The disclosure provides several novel elements described below.

1. The process recovers low-boiling compounds, including ketones and alcohols, from ethanol stream of industrial sugar-ethanol production processes;

2. The process provides the cost-effective recovery of acetone, 1-propanol, 2-propanol, or a combination thereof, from ethanol stream of industrial sugar-ethanol production processes, wherein a low capex investment is required being preferably restricted to downstream equipment and utilities for the recovery and storage of the low-boiling components of interest.

3. The process provides for the energy-efficient recovery of acetone, 1-propanol, 2-propanol, or a combination thereof from industrial sugar-ethanol production processes through energy integration, wherein available heat from the pre-existing ethanol production process can be recovered to run all or part of the add-on equipment required for the separation of the target products.

4. The disclosure provides a novel process downstream configuration for the recovery of acetone, 1-propanol, 2-propanol, or a combination thereof, from ethanol strain wherein the stream composition is derived from a process as described in, but not limited to, U.S. 2021/0261987A1.

The present disclosure describes the design of a novel process for the low-cost production, separation, and purification of low-boiling point products, including but not limited to, acetone and C3 alcohols from ethanol fermentation bioreactors, wherein the low-boiling products were produced by an engineered yeast strain alongside ethanol as major product at high concentrations.

The genetically modified yeast is derived from an industrial ethanol-producing yeast and is preferably a *Saccharomyces cerevisiae*, such the ones described in U.S. 2021/0261987A1, but not limited to them. The genetically modified yeast is derived from, but are not limited to, the *S. cerevisiae* PE-2, CAT-1, and Red strains. The genetically modified yeast is derived from an industrial ethanol-producing yeast that typically produces >80 g/L, >90 g/L, >100 g/L, >110 g/L, >120 g/L, or preferably >130 g/L of ethanol in <72 hs, <60 hs, <55 hs, or preferably <50 hs of fermentation time at industrial scale. The genetically modified yeast particularly produces >1 g/L, >3 g/L, >5 g/L, >10 g/L, and preferably >15 g/L of the low-boiling C3-product alongside with >100 g/L, >110 g/L, >120 g/L, or preferably >130 g/L of ethanol in <72 hs, <60 hs, <55 hs, or preferably <50 hs of fermentation time at industrial scale.

The present disclosure describes a novel process design to enable the production and recovery of such low-boiling products from ethanol, wherein the genetically modified yeast produces at least about 5 g/L acetone alongside with ~135 g/L ethanol ideally in 50-60 hs of fermentation time reaching high titer (>140 g/L of total solvents) and productivity (>2.5 g/L·h of solvents). In some embodiments, the novel process design enables the production and recovery of such low-boiling products from ethanol, wherein the genetically modified yeast produces at least about 10 g/L acetone alongside with ~130 g/L ethanol ideally in 50-60 hs of fermentation time reaching high titer (>140 g/L of total solvents) and productivity (>2.5 g/L·h of solvents). In some embodiments, the novel process design enables the production and recovery of such low-boiling products from ethanol, wherein the genetically modified yeast produces at least about 15 g/L acetone alongside with ~125 g/L ethanol ideally in 50-60 hs of fermentation time reaching high titer (>140 g/L of total solvents) and productivity (>2.5 g/L·h of solvents).

In the context of the disclosure, the fermentation step may be carried out either in accordance with a batch operation mode, a multi-stage batch operation mode, a semi-continuous operational mode (or "fed-batch" mode), or in accordance with an operational mode known as a continuous mode; these are well known to the person skilled in the art. Fermentation is carried out with a genetically modified yeast that produces at least about 5 g/L acetone alongside with ~135 g/L ethanol ideally in 50-60 hs of fermentation time reaching high titer (>140 g/L of total solvents) and productivity (>2.5 g/L·h of solvents). The genetically modified yeast produces at least about 5 g/L acetone alongside with ~135 g/L ethanol ideally in 50-60 hs of fermentation time reaching high titer (>140 g/L of total solvents) and productivity (>2.5 g/L·h of solvents). In some embodiments, the novel process design enables the production and recovery of such low-boiling products from ethanol, wherein the genetically modified yeast produces at least about 10 g/L acetone alongside with ~130 g/L ethanol ideally in 50-60 hs of fermentation time reaching high titer (>140 g/L of total solvents) and productivity (>2.5 g/L·h of solvents). In some embodiments, the novel process design enables the production and recovery of such low-boiling products from ethanol, wherein the genetically modified yeast produces at least about 15 g/L acetone alongside with ~125 g/L ethanol ideally in 50-60 hs of fermentation time reaching high titer (>140 g/L of total solvents) and productivity (>2.5 g/L·h of solvents).

The purification process in accordance with this disclosure can treat an alcoholic fermentation broth containing said low-boiling compound(s) diluted in ethanol and water, wherein such low-boiling compound (product) range in concentration from 5 g/L to 30 g/L, and ethanol as the main product from 80 g/L to 140 g/L, depending on the industrial ethanol fermentation processes based on corn, wheat, sugar beets, cellulose, sugarcane, or other biomass materials. Said fermentation low-boiling products can be obtained from solutions of C6-sugars brought in contact with anaerobic microorganisms, preferably genetically modified yeast strains, capable of converting theses sugars in ethanol and such commercially relevant low-boiling products. The carbon source is not limited to a C6 sugar, other carbon sources, such as 5-carbon sugars from biomass waste could be used as feedstock. As by-products of the yeast fermentation process, the so-called congeners are formed and their presence in the beer may require an additional separation equipment or sequence of equipment to enable the recovery of the low-boiling point compound of interest in the desired market specification.

The solution of C6-sugars may have different origins, but preferably originates from renewable sources already used in ethanol mills, like sugarcane, corn, beet, etc. With reference to FIG. 1, the C6-sugar solution enters the fermenter (FE) in order to undergo the fermentation step, wherein the genetically modified microorganism produces the target low-boiling product(s) like acetone, 1-propanol, and 2-propanol along with ethanol.

The output of this fermentation process leaves the fermenter (FE) either in the off-gas (vapor phase, 101) and in the broth (liquid phase, 102). Typically, the off-gas (101) contains incondensable gases (mainly $CO_2$) in a concentration between 92% w/w to 98% w/w, water in a concentration between 0.5% w/w to 3% w/w, and the main products in a concentration between 2% w/w to 5% w/w (preferably 2.5% w/w), with the ones with low boiling points present in more quantity than the ones with high boiling points. The fermentation broth (102) typically will contain water, the target low-boiling product in a range of concentration between 5 g/L and 30 g/L, the ethanol as the main product in a concentration between 40 g/L and 140 g/L, and other components present in smaller amounts than the main products, here called contaminants or congeners. The later were already present in the feedstock or were produced by the fermentation process, and may be organic acids, organic alcohols, proteins, saccharides, fats, minerals, and fibers for example.

The fermentation process may be conducted by different engineered yeast strains, keeping the industrial ethanol performance (titer, yield, productivity) similar to what is expected or already obtained by the ethanol millers, all always producing ethanol in larger quantities than the target low-boiling products (acetone, 1-propanol, and 2-propanol), and may be carried out at a temperature in a range of 30° C. to 37° C. This feature allows the technology to be implemented in existing industrial ethanol mills with little or ideally no modification in the industrial fermentation area.

For all cases wherein the low-boiling product is acetone, 1-propanol and/or 2-propanol, as shown in FIG. 1, the fermentation off-gas always undergoes a product recovery unit, in which the products present in the off-gas are absorbed by the water added at the top of the equipment (AC1); along with fermentation off-gas, vapors coming from the top of DC1 (109), the top of DC2 (205) and from MS (206) can also undergo this step in AC1, minimizing product loss in vapor phase. An absorption column or preferably a scrubber column can be used in this step, in which the off-gas and vapors from DC1, DC2 and MS combined (103) flow in preferably counter current with a solvent like water in a proportion of 0.5 to 2 parts of water for one part of off-gas in a mass basis. This process produces a purified gas stream with small quantities of products and a water stream with recovered C3-products. The solvent used in this is step (104) is preferably, but not limited to, water and must be at a temperature in a range of 5° C. to 45° C.

The stream containing recovered products (105) is mingled with the fermentation broth (102) forming a mixture typically called beer, which will be stored in the beer tank (BT). The beer (107) is sent to the DC1 separation unit. This beer is preheated by heat integration with stillage (E1) and passes through DC1 separation unit. The DC1 separation unit is one distillation column capable of treating solids and is usually called beer or mash column. This step removes water, heavy components, and solids at the bottom of the column DC1, with product loss limited to low levels at the so-called stillage. The stillage can have different end uses, according to the feedstock selected and may have a content of 65% w/w to 99% w/w of water, and the rest will be composed of solids present in the feedstock and C6-sugars that were not consumed during fermentation. The stream coming out from the top of the DC1 step (109) may be composed from 15% w/w to 60% w/w of low boiling points products, ethanol, and from 40% w/w to 85% w/w of carbon dioxide. The stream from the top of the DC1 step (109) will be recycled to AC1 to recover products and remove incondensable gases. The side stream in DC1 contains products and water both at a concentration in a range of 35% to 80% w/w. If a distillation column is used in the DC1 step, it may operate at a range of pressure between 0.1 and 3 bar, the beer must be at temperature between 70° C. and 115° C., and the side stream at temperature between 70° C. and 135° C. Eventual heat integrations with column condensers will depend on the products being separated.

Figure 2:
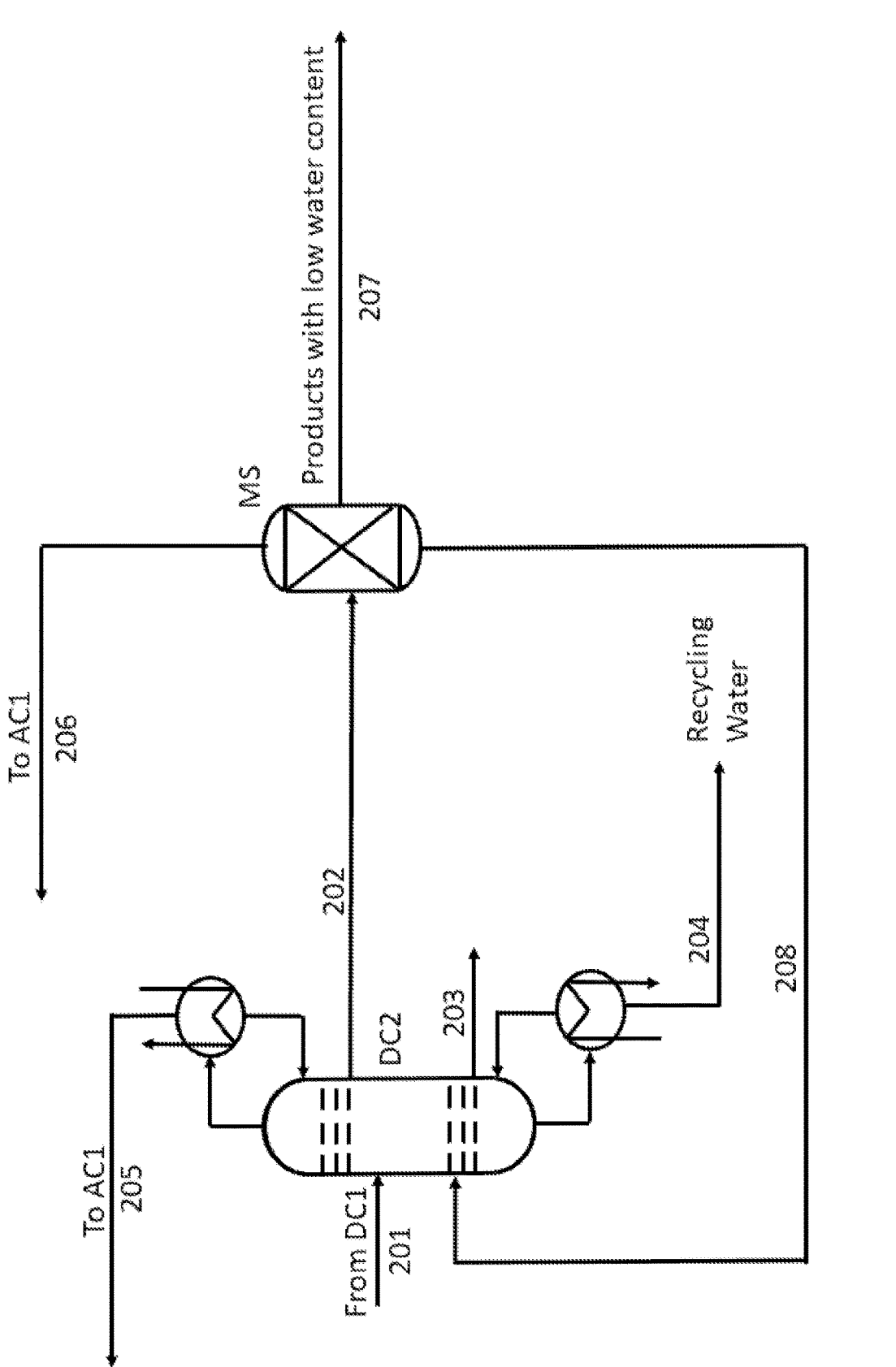
FIG. 2 is a process flowsheet representation for the second common part of the process in which water content is reduced from high to low water content.

As shown in FIG. 2, this side product stream from DC1 (201) then passes through a second separation unit (DC2), preferably a distillation column, usually called rectifier column. The DC2 bottom stream (204) is mainly composed of water (80% to 100%) at a range of temperature between 65° C. and 135° C. and that water can be recycled to the fermentation process upstream, saving water consumption in the process. The intermediate water content stream (202) of this equipment operates at a range of temperature between 50° C. and 110° C. and it may have from 5% w/w to 10% w/w of water, from 1% w/w to 15% w/w of low-boiling products like acetone, 1-propanol, 2-propanol, congeners, etc., and from 75% w/w to 95% w/w of ethanol. The DC2 distillation column operates at a pressure in a range from 0.1 bar to 3 bar. The vents from the top of DC2 (205) return to the AC1 unit to avoid the loss of desired products. If desired, for specific applications, additional operational units can be added to purify fusel oil stream (203) to be sold as a product. Optionally, the fusel oil stream (203) can undergo a separation phase step, with or without water addition, and the phase rich in water can be recycled to any previous process step; the organic phase—that contains the fusel oil—could be either isolated or could be added to the final ethanol stream without disturbing the ethanol fuel specification. Alternatively, a flash tank could be used to recover acetone, propanol, and ethanol from the fusel oil stream before the separation steps abovementioned. In some process configurations, DC2 could have additional side draws to remove light superior alcohols. In such configurations, additional unit operations may be required to reduce acetone, propanol, and ethanol losses. The intermediate water content stream exiting DC2 (202) is forwarded to a drying/dewatering unit (MS) to have its water content reduced in a range of 2.5% to 0.5% w/w, a key step to operating expense reduction, preservation of product specification, and economic viability. This drying process can be performed by a membrane separation system or any other de-watering industrial equipment or preferably by adsorption using a molecular sieve system. This step is critical for the process when propanol is present because the presence of higher amounts of water will complicate the separation of ethanol from propanol. The water removed in this MS unit may contain any of the products, so this stream (208) is recycled back to the DC2. The stream with low water content leaving the MS (207) is sent to a set of distillation steps that will vary according to the products being generated at fermentation.

Figure 3:
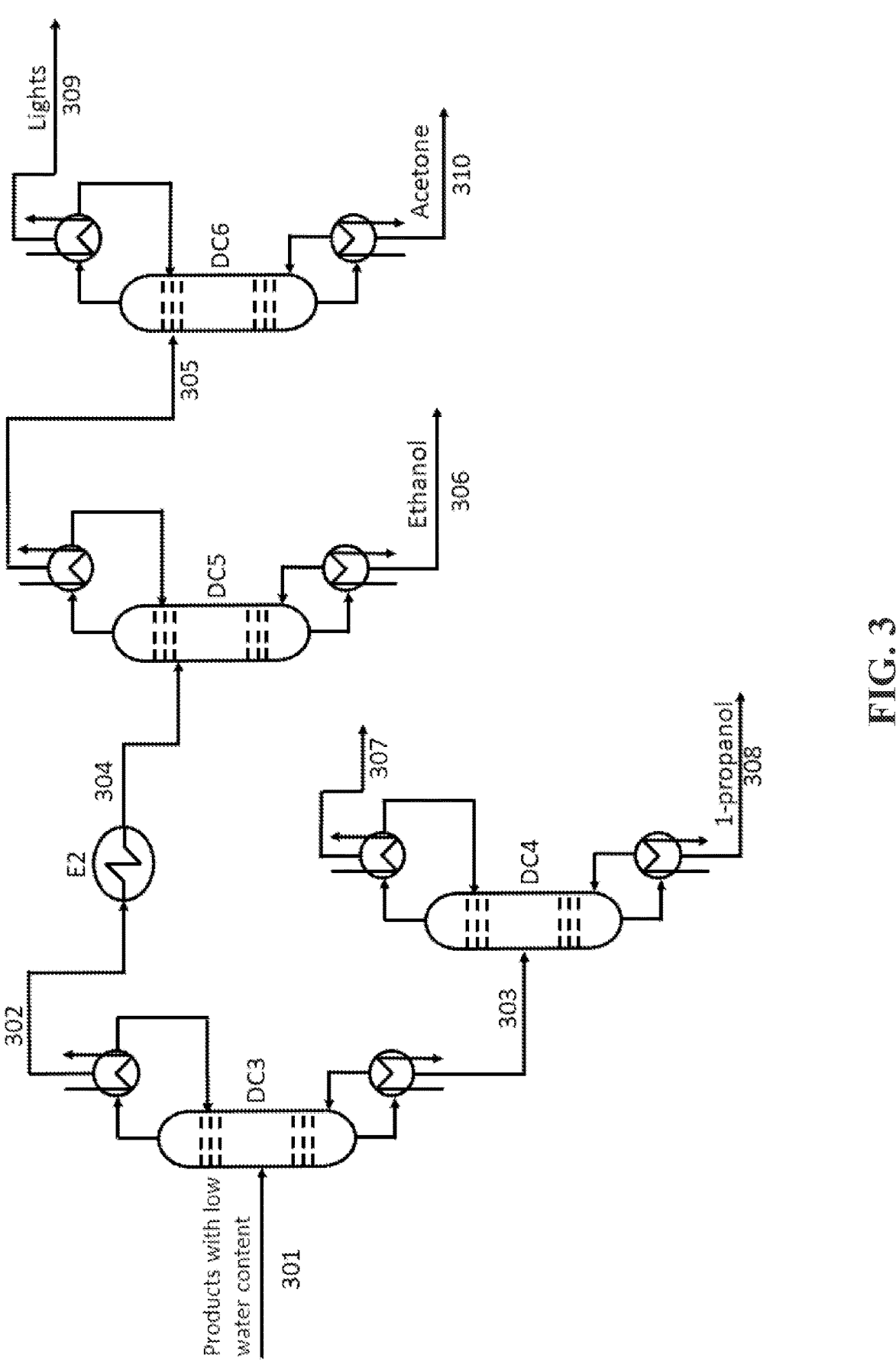
FIG. 3 is a process flowsheet representation for the distillation set required when ethanol, 1-propanol, and acetone are produced as main products. For processes that produce only ethanol and acetone, DC3 and DC4 are removed.

When the engineered yeast strain produces both 1-propanol and acetone along with ethanol as the major component, a set of at least two distillation columns are required to obtain the three products at purity required for final application (see FIG. 3). The first column (DC3) is fed with the fermentation products such as 1-propanol, acetone, ethanol and contaminants (301) and removes most of the 1-propanol at the bottom (303) at a high purity. A second column (DC4) may be added to mainly polish the 1-propanol to desired purity, with impurities leaving at the top of the column (307) and 1-propanol leaving at the bottom stream of this column (308). Impurities may refer to any fermentation co-product different from 1-propanol.

A third column (DC5), here called the ethanol specification column, receives the ethanol at high concentration (302) with acetone and contaminants mixture condensed in E1. An acetone rich stream (305) can be drawn from the side or top product in column DC5, and purified ethanol at the bottom (306). If desired acetone purity is not reached in DC5, an additional distillation system can be added, with acetone, acetaldehyde, and other contaminants (305), also called "lights," leaving at the top as a mixture and condensed to the fourth column (DC6). Acetone can be specified as a bottom product stream (310) in column DC6, with acetaldehyde and other contaminants left at the top (309). More columns could be added in the process to remove more contaminants. DC4, DC5, and DC6 can be single distillation columns, vacuum columns, or a set of distillation columns, since the presence of congeners alongside ethanol and the co-products of interest may require a sequence of distillation equipment to enable the recovery of the target molecules within the desired market specification. Also, to increase the recovery of desired products, in some embodiments, stream 309 could be partially or totally recycled to AC1. In another embodiment, a new scrubber can be added after DC6 which is fed with stream 309 at the bottom. A solvent (such as water) can be added at the top which adsorbs the products, allowing them to be recovered in an aqueous solution at the bottom of this scrubber which is then recycled to the beer tank (BT). In another embodiment, this new scrubber could also receive more vapor streams, like the top streams from the other distillation columns (109, 205, 307), the vent from the molecular sieve system (206) and even the top stream of AC1 (106).

When the engineered yeast strain produces just acetone as the target low-boiling product along with ethanol as the main product of the fermentation, the columns DC3 and DC4, presented in FIG. 3, are no longer required—the process design is simpler and requires smaller capex expense.

Figure 4:
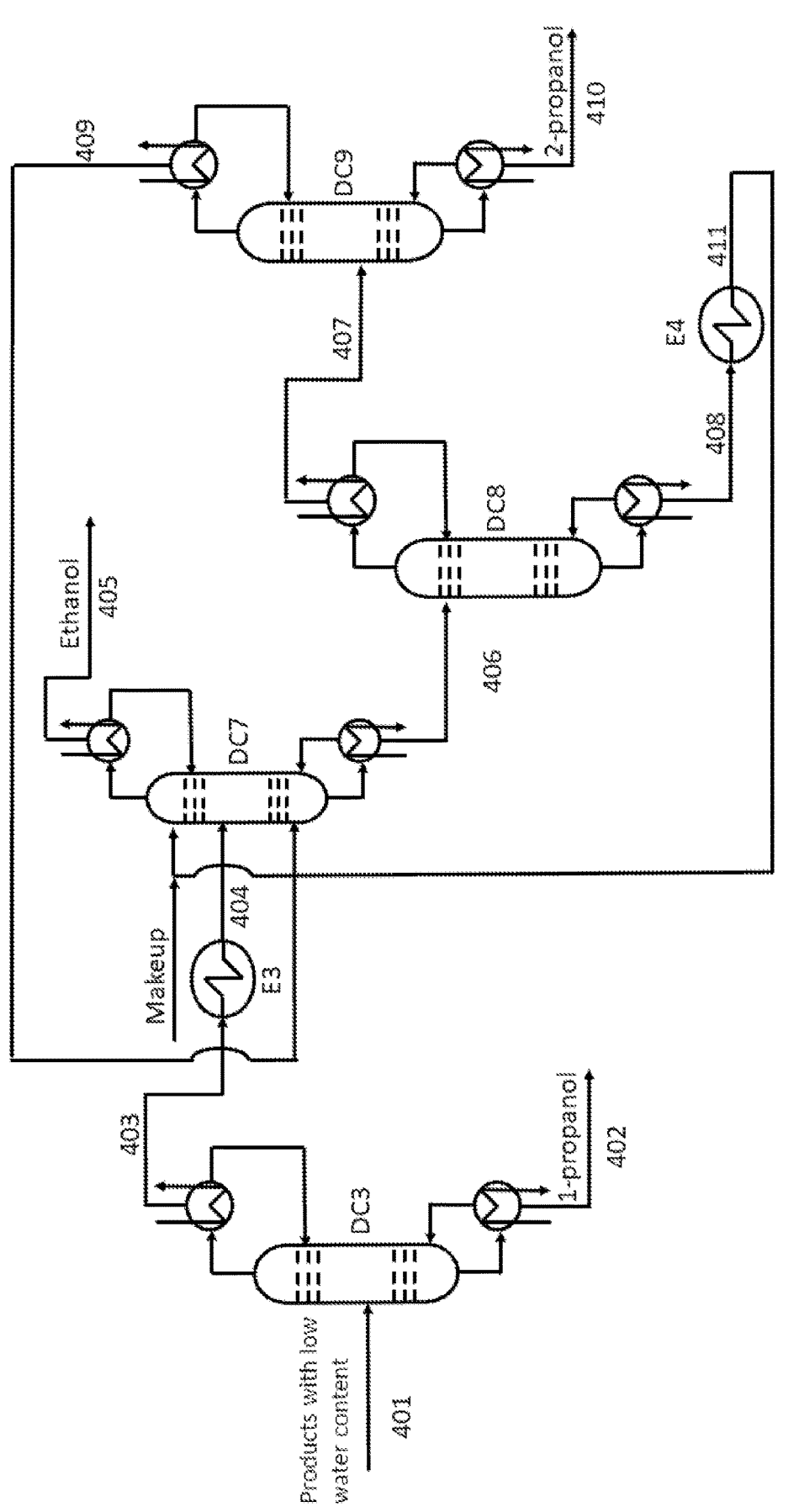
FIG. 4 is process flowsheet representation for the distillation set required when ethanol, 1-propanol, and 2-propanol are produced as main products. For processes that produce only ethanol and 2-propanol, DC3 is removed.

In the case an engineered yeast strain produces both 1-propanol and 2-propanol as the target low-boiling products along with ethanol as the major component of the fermentation, at least one distillation column or a set of two or more distillation columns is required to obtain the three products at purity required for the final application (see FIG. 4). The products with low water content (401) are fed into a first column (DC3), which specifies 1-propanol at the bottom stream (402) since 1-propanol has a higher boiling point than ethanol and 2-propanol. DC3 can be a single distillation column or a series of columns to polish 1-propanol to desired purity. Ethanol and 2-propanol leave at the top stream of column DC3 (403). Since they have very low relative volatilities, the option selected for separation can be preferentially extractive distillation. Vacuum distillation can also be used, but in this case, one less column would be required, since no solvent recovery would be required. The solvent selected was limonene, but any solvent with more affinity for 2-propanol could be used. The ethanol and 2-propanol mixture enters DC7 as stream (404) in a vapor state after passing through E3, and the solvent is fed as a liquid at the top, mainly extracting the 2-propanol from the vapor phase, but also carrying part of the ethanol. The mixture of solvent, 2-propanol and ethanol leaves at the bottom stream (406), and ethanol can be obtained at desired purity at the top (405). In column DC8, the solvent (408) can be recovered at the bottom and recycled back to DC7 after being cooled in E4, becoming (411). The mixture of ethanol and 2-propanol leaving at the top of DC8 (407) goes to the last column DC9, in which 2-propanol is obtained specified at the bottom (410) and a mixture of the ethanol with 2-propanol returns to DC7 (409). The reboilers of DC9 and DC3 could be heat integrated with DC7 and DC2 condensers, respectively, if the equipment operates in favorable temperature conditions. DC3, DC7, and DC9 can be single distillation columns or a set of distillation columns, since the presence of congeners alongside ethanol and the co-products of interest (1-propanol and 2-propanol, respectively) may require a sequence of distillation equipment to enable the recovery of the target molecules within the desired market specification.

In the case an engineered yeast strain produces 2-propanol alongside ethanol as the major component of the fermentation, the column DC3, presented in FIG. 4, is no longer required, and only the DC9 reboiler heat integration with the DC7 condenser could be maintained if the process allows it.

Example 2: Industrial Plant Recovery of Low-Boiling Point Component(s) from an Ethanol Stream The following non-limiting example refers to FIG. 1, FIG. 2, FIG. 3, and FIG. 4. The process described herein was demonstrated by simulation using the software of process design and simulation Aspen Plus. Thermodynamic model NRTL-HOC was selected based on the components considered in the simulation, and experimental liquid-vapor equilibrium data was used to evaluate the quality of the existing binary parameters and also to do regression of the so called inadequate or even inexistent parameters. The mass balance for an industrial scale plant in metric tons per hour is shown in Tables 1, 2, and 3, and the equipment information is presented in Table 4.

In the simulation, one or more fermentative units FE producing acetone and ethanol as the main products at a temperature of 35° C. and an absolute pressure of 1.1 bar were considered. Additionally, other fermentative by-products, such as acetaldehyde, methanol, ethyl-acetate, isopropyl alcohol, 1-propanol, isoamyl alcohol, and acetic acid were produced, referred to as "Contaminants" in this example due to their low concentration in the process. Along with other components, like soluble and insoluble solids, they were referred to as "Others" in the mass balance.

The off-gas generated during fermentation 101, mainly composed of carbon dioxide (about 94 wt %), was mixed with two recycle off-gas streams 109 and 205, the first one coming from DC1 and the second one coming from DC2, resulting in stream 103, with a flow of about 23 t/h and a composition similar to 101 in terms of high carbon dioxide concentration. Stream 206 was considered with mass flow equal to zero for the purpose of this example.

The gas mixture in stream 103 was bottom fed into AC1, that operated at 1.0 bar in absolute top pressure and contained 10 stages for the recovery of the products present in 103, for that, the water stream 104 with a flow rate of about 26 t/h was fed into the top of the column. The contact between water and the off-gas stream resulted in the absorption of some components in the liquid phase, forming stream 105 at the bottom of AC1, an aqueous stream with the recovered products, which is conducted to BT, where it was be mixed with the fermentation broth, stream 102. Therefore, AC1 produced stream 106 at the top, which is rich in carbon dioxide and poor in main products.

The fermentation broth was discharged from FE through 102 at a flow rate of about 135 t/h, containing approximately 13 wt. % in main products. The broth was fed into BT simultaneously with 105, resulting in stream 107.

Stream 107 had a temperature of 36° C. and was preheated in E1, exchanging heat with stream 111, and reached a temperature of 100° C., becoming stream 108. After the heat exchanger, the stream was fed into the first distillation column DC1, which operated at 2.0 bar in absolute top pressure, with 32 stages.

In the DC1 separation unit, the removal of incondensable gases was done in the top stream 109, which was recycled to AC1 for the recovery of main products. The side stream 110 that goes to DC2 contained the majority of main products separated by DC1, with a flow rate of approximately 31 t/h, 56 wt % of which was ethanol and 4 wt % was acetone. Lastly, the bottom stream 111 was where the removal of solids, heavy components, and the majority of the water occurs, with stream 112 going to stillage.

The DC2 distillation column operated at 1.6 bar in absolute top pressure, with 60 stages and was fed by stream 201 discharged from DC1 as stream 110. In this column, most of the main products were recovered as a side stream 202. Part of the volatile contaminants were removed at the top as stream 205 and recycled to AC1 for the recovery of main products. Most of the remaining water was removed at the bottom of DC2 as stream 204. Lastly, a second side stream, 203, was removed from DC2, the so-called fusel oil by-product.

Stream 202 contained about 8 wt % of water so it was passed through the dewatering unit MS, which was represented by a molecular sieve system in the simulation. Stream 202 was superheated before entering the zeolite bed. In one bed, the adsorption of water occurred while the other bed was being regenerated. The system contained two outlet streams, a products stream with low water content 207 and a recycle stream 208. Stream 207 contains 93 wt. % ethanol, 6 wt. % acetone, and 0.5% w/w water at a flow rate of about 19 t/h. The recycle stream 208, contained a significant quantity of main products, 67 wt. % ethanol, 28 wt. % water and 5 wt. % acetone, so it was returned to DC2, at a flow rate of about 7 t/h.

In this example, the stream coming from MS as stream 207, had a low amount of 1-propanol, about 0.03 wt. %, so it was fed directly to the distillation column DC5 as stream 304, which contained 55 stages and was operated at 0.7 bar absolute top pressure. This column was designed such that anhydrous ethanol at desired specification was obtained at the bottom as stream 306, with an ethanol content of 99.0 wt. %, and flow rate of about 18 t/h. Stream 305, obtained at the top of DC5 was sent to DC6 for further purification and to obtain acetone.

Stream 305 was fed to DC6 with a flow rate of 1.2 t/h, this distillation column contained 45 stages and operated at top absolute pressure of 1.8 bar. Light contaminants were removed at the top stream 309, at a flow rate of 30 kg/h, which contained about 87 wt. % of acetaldehyde. Acetone at desired specification can be obtained at the bottom as stream 310, with a flow rate of 1.2 t/h, with 99.5 wt. % purity.

US 12,674,183 B2

63 64

TABLE 1

|  | 101 | 102 | 103 | 104 | 105 | 106 | 107 | 108 | 109 | 110 | 111 | 112 |
|---|---|---|---|---|---|---|---|---|---|---|---|---|
| T (° C.) | 35 | 34 | 35 | 30 | 39 | 33 | 36 | 100 | 61 | 108 | 124 | 45 |
| P (bara) | 1.1 | 1.1 | 1.1 | 3.0 | 1.0 | 1.0 | 3.0 | 2.7 | 2.0 | 2.1 | 2.3 | 2.7 |
| Carbon dioxide (t/h) | 21.4 | 0.2 | 21.6 | 0.0 | 0.0 | 21.6 | 0.2 | 0.2 | 0.2 | 0.0 | 0.0 | 0.0 |
| Acetone (t/h) | 0.2 | 1.1 | 0.3 | 0.0 | 0.3 | 0.1 | 1.3 | 1.3 | 0.1 | 1.3 | 0.0 | 0.0 |
| Ethanol (t/h) | 0.7 | 16.9 | 0.7 | 0.0 | 0.7 | 0.0 | 17.6 | 17.6 | 0.1 | 17.5 | 0.1 | 0.1 |
| Water (t/h) | 0.4 | 95.1 | 0.5 | 25.6 | 25.6 | 0.5 | 120.7 | 120.7 | 0.0 | 12.5 | 108.1 | 108.1 |
| Others (t/h) | 0.0 | 21.7 | 0.0 | 0.0 | 0.0 | 0.0 | 21.7 | 21.7 | 0.0 | 0.2 | 21.5 | 21.5 |

TABLE 2

|  | 201 | 202 | 203 | 204 | 205 | 206 | 207 | 208 |
|---|---|---|---|---|---|---|---|---|
| T (° C.) | 108 | 90 | 103 | 119 | 75 |  | 40 | 70 |
| P (bara) | 2.1 | 1.6 | 1.8 | 1.9 | 1.6 |  | 3.0 | 2.7 |
| Carbon dioxide (t/h) | 0.0 | 0.0 | 0.0 | 0.0 | 0.0 |  | 0.0 | 0.0 |
| Acetone (t/h) | 1.3 | 1.5 | 0.0 | 0.0 | 0.1 |  | 1.2 | 0.3 |
| Ethanol (t/h) | 17.5 | 21.8 | 0.1 | 0.0 | 0.0 |  | 17.4 | 4.4 |
| Water (t/h) | 12.5 | 1.9 | 0.2 | 12.2 | 0.0 |  | 0.1 | 1.8 |
| Others (t/h) | 0.2 | 0.2 | 0.0 | 0.0 | 0.0 |  | 0.1 | 0.0 |

TABLE 3

|  | 301 | 302 | 303 | 304 | 305 | 306 | 307 | 308 | 309 | 310 |
|---|---|---|---|---|---|---|---|---|---|---|
| T (° C.) |  |  |  | 40 | 44 | 78 |  |  | 44 | 78 |
| P (bara) |  |  |  | 3.0 | 0.7 | 1.0 |  |  | 1.8 | 2.0 |
| Carbon dioxide (t/h) |  |  |  | 0.0 | 0.0 | 0.0 |  |  | 0.0 | 0.0 |
| Acetone (t/h) |  |  |  | 1.2 | 1.2 | 0.0 |  |  | 0.0 | 1.2 |
| Ethanol (t/h) |  |  |  | 17.4 | 0.0 | 17.4 |  |  | 0.0 | 0.0 |
| Water (t/h) |  |  |  | 0.1 | 0.0 | 0.1 |  |  | 0.0 | 0.0 |
| Others (t/h) |  |  |  | 0.1 | 0.0 | 0.1 |  |  | 0.0 | 0.0 |

TABLE 4

| Equipment | AC1 | DC1 | DC2 | DC5 | DC6 |
|---|---|---|---|---|---|
| Top pressure (bara) | 1.0 | 2.0 | 1.6 | 0.7 | 1.8 |
| Top temperature (° C.) | 33 | 61 | 75 | 44 | 44 |
| Number of stages (without condenser and/or reboiler) | 10 | 32 | 60 | 55 | 45 |
| Reboiler energy consumption (MW) | — | 15.8 | 10.5 | 4.0 | 0.3 |

Figure 5:
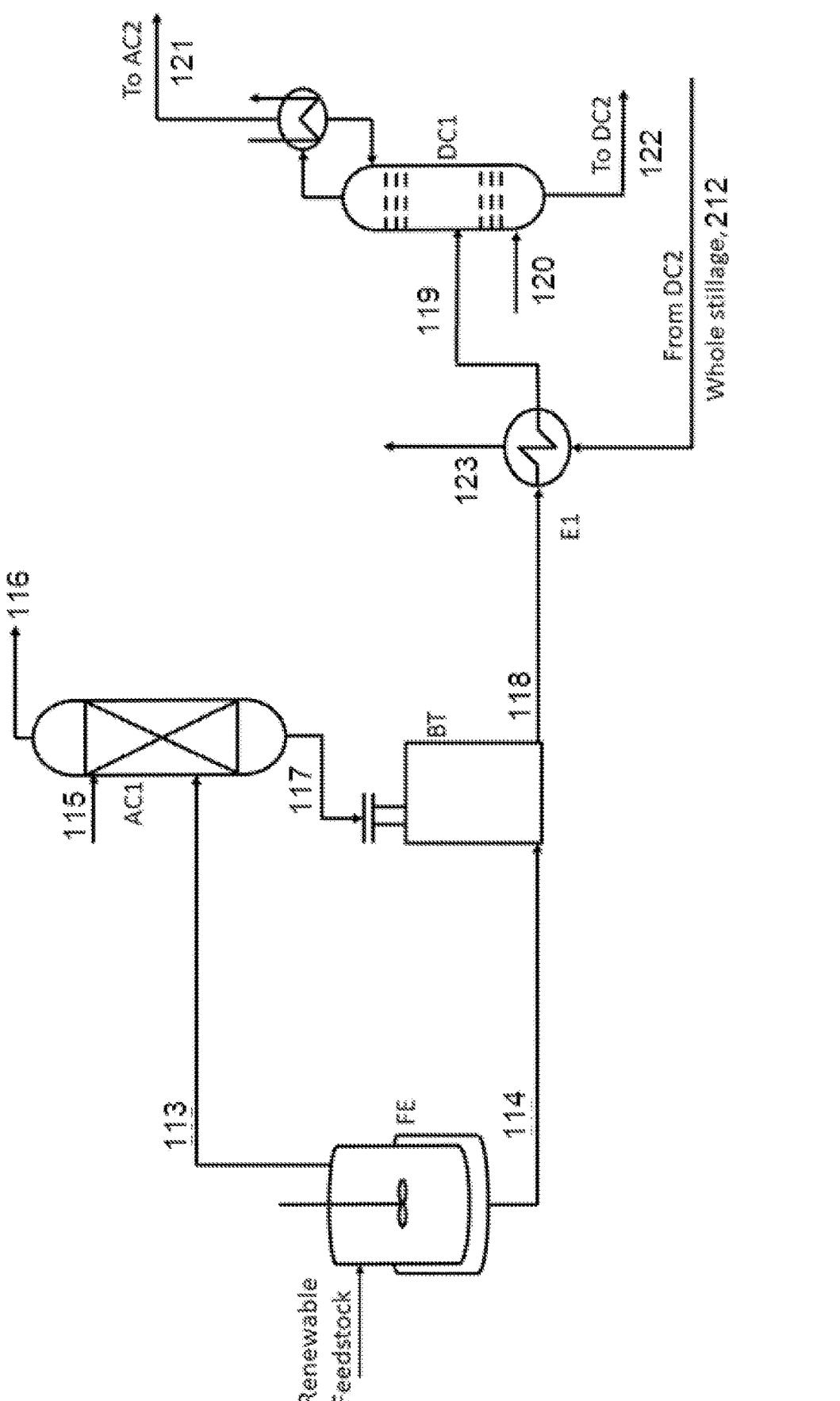
FIG. 5 is a process flowsheet representation for the first part of a simulation of the pilot plant recovery of low-boiling point component(s) from an ethanol stream.
Figure 6:
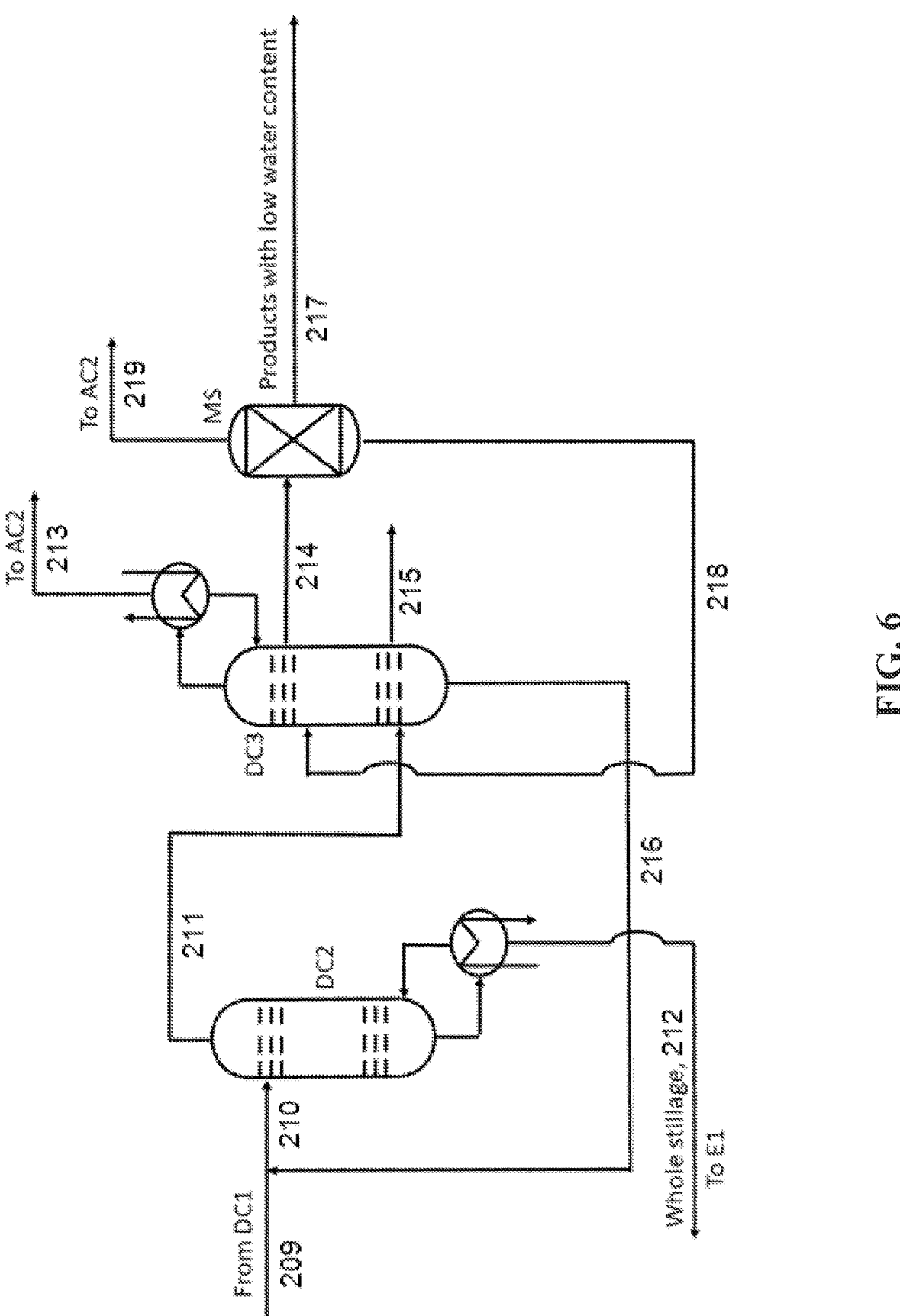
FIG. 6 is a process flowsheet representation for the second part of the simulation of the pilot plant recovery of low-boiling point component(s) from an ethanol stream.
Figure 7:
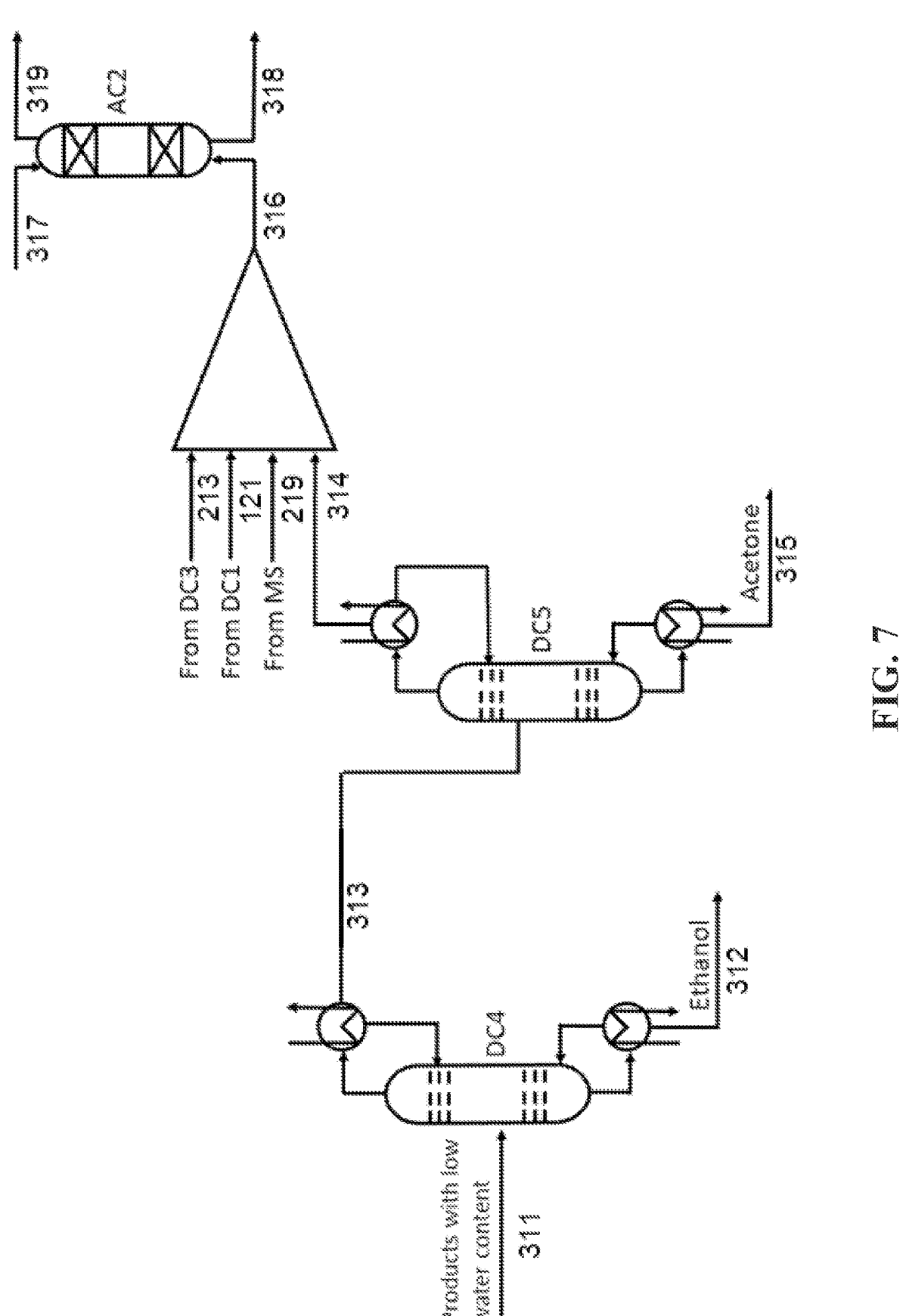
FIG. 7 is a process flowsheet representation for the third part of the simulation of the pilot plant recovery of low-boiling point component(s) from an ethanol stream.

Example 3: Pilot Plant Recovery of Low-Boiling
Point Component(s) from an Ethanol Stream The following non-limiting example refers to FIG. 5, FIG. 6, and FIG. 7. The process described herein was demonstrated by simulation using the software of process design and simulation Aspen Plus. Thermodynamic model NRTL-HOC was selected based on the components considered in the simulation, and experimental liquid-vapor equilibrium data was used to evaluate the quality of the existing binary parameters and also to do regression of the so called inadequate or even inexistent parameters. The mass balance for a pilot scale plant in kilograms per hour is shown in Tables 5, 6, and 7, and the equipment information is presented in Table 8.

In the simulation, one or more fermentative units FE producing acetone and ethanol as the main products at a temperature of 35° C. and an absolute pressure of 1.1 bar were considered. Additionally, other fermentative by-products, such as acetaldehyde, methanol, ethyl-acetate, isopropyl alcohol, 1-propanol, isoamyl alcohol, and acetic acid were produced, which were referred to as "Contaminants" in this example due their low concentration in the process. Along with other components, like soluble and insoluble solids, they were referred to as "Others" in the mass balance.

The off-gas generated during the fermentation process 113, with a flow rate of about 62 kg/h, and mainly composed of carbon dioxide (about 94 wt. %), was bottom fed into AC1, that operated at 1 bar in absolute top pressure and contained 10 stages for the recovery of the products present in 113, for that, the water stream 115 with a flow rate of about 70 kg/h was fed into the top of the column. The contact between water and the off-gas stream resulted in the absorption of some components in the liquid phase, forming stream 117 at the bottom of AC1, an aqueous stream with the recovered products, which was conducted to BT, where it was mixed with the fermentation broth, stream 114. Therefore, AC1 produces stream 116 at the top, which was rich in carbon dioxide and poor in main products.

The fermentation broth was discharged from FE through 114 at a flow rate of about 366 kg/h, containing approximately 13 wt. % in main products. The broth was fed into BT simultaneously with 117, resulting in stream 118.

Stream 118 had a temperature of 36° C. and was preheated in E1, exchanging heat with stream 212, and reached a temperature of 100° C., becoming stream 119. After the heat exchanger, the stream was fed into the first distillation column DC1, which operated at 1.1 bar in absolute top pressure, with 6 stages.

In the DC1 separation unit, steam was injected directly at the bottom as stream 120, and the removal of incondensable gases was done in the top stream 121, which was led to AC2 for the recovery of main products. The bottom stream 122, that goes to DC2, contained the majority of main products, with a flow rate of approximately 460 kg/h, 10 wt. % of which was ethanol and 1 wt. % of which was acetone.

The DC2 distillation column operated at 1.7 bar in absolute top pressure, with 22 stages and was fed by stream 210, which is a mix of streams 216 and 209, the first stream was a recycle stream from DC3 and the later stream was discharged from DC1 as stream 122. In this column, most of the main products were recovered at the top stream 211. The bottom stream 212 was where the removal of solids, heavy components, and the majority of the water occurred, which was passed through E1, becoming stream 123.

Stream 211 contained 30 wt. % ethanol and 2 wt. % acetone, and was bottom fed into the DC3 distillation column, which operated at 1.1 bar top absolute pressure, and had 28 stages. The main products were recovered as a side stream, 214. Part of the volatile contaminants were removed at the top as stream 213 and sent to AC2 for recovery of the main products. Most of the remaining water was removed at the bottom of DC3 as stream 216 and, due to significant concentration of main products, this stream was recycled to DC2. Lastly, a second side stream, 215, was removed from DC3, the so-called fusel oil by-product.

Stream 214 contained about 8 wt. % of water and thus was passed through the dewatering unit MS, which was represented by a molecular sieve system in the simulation. Stream 214 was superheated before entering the zeolite bed. In one bed, the adsorption of water occurred while the other bed was being regenerated. The system contained two outlet streams, a products stream with low water content 217 and a recycle stream 218. Stream 219 was considered with a mass flow equal to zero for the purpose of this example. Stream 217 contained 93 wt. % ethanol, 5 wt. % acetone, and 0.5% w/w water at a flow rate of about 50 kg/h. The recycle stream 218, contained a significant quantity of main products, 68 wt. % ethanol, 28 wt. % water and 4 wt. % acetone, so it was returned to DC3, at a flow rate of about 17 kg/h.

Stream 311, coming from MS as stream 217 was fed to the distillation column DC4, which contained 29 stages and was operated at 0.7 bar absolute top pressure. This column was designed to obtain anhydrous ethanol at the desired specification at the bottom as stream 312, with an ethanol content of 99.0 wt. %, and flow rate of about 47 kg/h. Stream 313, obtained at the top of DC4 was sent to DC5 for further purification and to obtain acetone.

Stream 313 was fed to DC5 with a flow rate of 2.8 kg/h, this distillation column contained 15 stages and operated at top absolute pressure of 1.8 bar. Acetone at the desired specification could be obtained at the bottom as stream 315, with a flow rate of 2.6 kg/h and with 99.6 wt. % purity. Light contaminants were removed at the top stream 314, at a flow rate of 0.2 kg/h, which contained about 69 wt. % acetone and 28 wt. % of acetaldehyde, and were sent to AC2, for the recovery of main products.

AC2, an absorption column, operated at 1.0 bar in absolute top pressure, with 10 stages and was bottom fed by stream 316, which was a mix of streams 121, 213, 219, and 314, with a flow rate of about 2 kg/h, 37 wt. % acetone, and 21 wt. % ethanol. Water, as stream 317, was added at the top stage at a flow rate of about 7 kg/h, and products were recovered as an aqueous solution at the bottom stream 318, while the top stream 319 was rich is carbon dioxide and poor in main products.

If desired, to increase the overall downstream process recovery of acetone and ethanol, stream 318 could be recycled back to BT.

TABLE 5

| | 113 | 114 | 115 | 116 | 117 | 118 | 119 | 120 | 121 | 122 | 123 |
|---|---|---|---|---|---|---|---|---|---|---|---|
| T (° C.) | 35 | 34 | 30 | 32 | 39 | 36 | 100 | 178 | 59 | 93 | 52 |
| P (bara) | 1.1 | 1.1 | 3.0 | 1.0 | 1.0 | 3.0 | 3.0 | 9.6 | 1.1 | 1.2 | 3.0 |
| Carbon dioxide (kg/h) | 58.0 | 0.5 | 0.0 | 57.9 | 0.1 | 0.6 | 0.6 | 0.0 | 0.6 | 0.0 | 0.0 |
| Acetone (kg/h) | 0.5 | 2.9 | 0.0 | 0.1 | 0.4 | 3.3 | 3.3 | 0.0 | 0.5 | 2.9 | 0.0 |
| Ethanol (kg/h) | 1.8 | 45.7 | 0.0 | 0.0 | 1.8 | 47.5 | 47.5 | 0.0 | 0.3 | 47.2 | 0.0 |
| Water (kg/h) | 1.2 | 257.8 | 69.5 | 1.2 | 69.5 | 327.3 | 327.3 | 23.8 | 0.1 | 351.1 | 350.5 |
| Others (kg/h) | 0.1 | 58.9 | 0.0 | 0.0 | 0.0 | 58.9 | 58.9 | 0.0 | 0.0 | 58.9 | 58.4 |

TABLE 6

| | 209 | 210 | 211 | 212 | 213 | 214 | 215 | 216 | 217 | 218 | 219 |
|---|---|---|---|---|---|---|---|---|---|---|---|
| T (° C.) | 93 | 95 | 106 | 118 | 72 | 81 | 95 | 102 | 40 | 28 | |
| P (bara) | 3.0 | 3.0 | 1.7 | 1.9 | 1.1 | 1.2 | 1.2 | 1.3 | 3.0 | 3.0 | |
| Carbon dioxide (kg/h) | 0.0 | 0.0 | 0.0 | 0.0 | 0.0 | 0.0 | 0.0 | 0.0 | 0.0 | 0.0 | |
| Acetone (kg/h) | 2.9 | 3.0 | 3.0 | 0.0 | 0.1 | 3.4 | 0.0 | 0.1 | 2.7 | 0.7 | |
| Ethanol (kg/h) | 47.2 | 51.8 | 51.8 | 0.0 | 0.1 | 58.4 | 0.3 | 4.6 | 46.8 | 11.7 | |
| Water (kg/h) | 351.1 | 466.2 | 115.7 | 350.5 | 0.0 | 5.1 | 0.4 | 115.1 | 0.2 | 4.8 | |
| Others (kg/h) | 58.9 | 59.0 | 0.5 | 58.4 | 0.0 | 0.4 | 0.1 | 0.1 | 0.3 | 0.1 | |

TABLE 6-continued

| | 209 | 210 | 211 | 212 | 213 | 214 | 215 | 216 | 217 | 218 | 219 |
|---|---|---|---|---|---|---|---|---|---|---|---|

TABLE 7

| | 311 | 312 | 313 | 314 | 315 | 316 | 317 | 318 | 319 |
|---|---|---|---|---|---|---|---|---|---|
| T (° C.) | 40 | 72 | 44 | 66 | 76 | 61 | 30 | 68 | 37 |
| P (bara) | 3.0 | 10.0 | 0.7 | 1.8 | 10.0 | 1.1 | 3.0 | 1.0 | 1.0 |
| Carbon dioxide (kg/h) | 0.0 | 0.0 | 0.0 | 0.0 | 0.0 | 0.6 | 0.0 | 0.0 | 0.6 |
| Acetone (kg/h) | 2.7 | 0.0 | 2.7 | 0.1 | 2.6 | 0.7 | 0.0 | 0.7 | 0.0 |
| Ethanol (kg/h) | 46.8 | 46.7 | 0.0 | 0.0 | 0.0 | 0.4 | 0.0 | 0.4 | 0.0 |
| Water (kg/h) | 0.2 | 0.2 | 0.0 | 0.0 | 0.0 | 0.1 | 6.9 | 6.9 | 0.0 |
| Others (kg/h) | 0.3 | 0.3 | 0.1 | 0.1 | 0.0 | 0.1 | 0.0 | 0.1 | 0.0 |

TABLE 8

| Equipment | AC1 | DC1 | DC2 | DC3 | DC4 | DC5 | AC2 |
|---|---|---|---|---|---|---|---|
| Top pressure (bara) | 1.0 | 1.1 | 1.7 | 1.1 | 0.7 | 1.8 | 1.0 |
| Top temperature (° C.) | 32 | 59 | 106 | 72 | 44 | 66 | 37 |
| Number of Stages (without condenser and/or reboiler) | 10 | 6 | 22 | 28 | 29 | 15 | 10 |
| Reboiler energy consumption (kW) | — | — | 96 | — | 13 | 3 | — |

In summary, the present disclosure provides a novel process design, alternative to existing processes of higher technology complexity or operational costs like ABE and IBE systems. Compared to existing processes, the disclosed process provides for the lower-cost production, separation, and purification of low-boiling products including, but not restricted to, acetone from an ethanol stream. The disclosed process is simpler, more efficient and has reduced capital expenses compared to existing processes since the process described herein has optimized operating expenses, increasing its cost-competitiveness and adoption by industrial ethanol millers.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of and/or consisting essentially of language. Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A process for the isolation of one or more low boiling compounds from a fermentation broth and a fermentation off-gas, the process comprising:

(a) flowing a fermentation off-gas coming from one or more fermenters through a product recovery unit wherein the flow of the off-gas is counter to a solvent flowing through the product recovery unit and obtaining a solvent stream comprising the one or more low boiling compounds and ethanol;

(b) mixing the solvent stream of (a) with the fermentation broth and passing the resulting fermentation mixture through a first separation unit to form a high water content stream comprising about 30-90% w/w water, ethanol, and the one or more low boiling compounds;

(c) passing the high water content stream of (b) through a second separation unit to form an intermediate water content stream comprising water, ethanol, and the one or more low boiling compounds;

(d) passing the intermediate water content stream of (c) through a dewatering unit to form a low water content stream comprising ≤2.5% w/w water; and (e) passing the low water content stream of (d) through one or more operational units, separating the ethanol and the one or more low boiling compounds;

wherein the process further comprises recycling a gas stream output from at least one of the first separation unit, the second separation unit, or the dewatering unit to the product recovery unit.

2. The process of claim 1, wherein the fermentation broth and fermentation off-gas comprise water, the one or more low boiling compounds, ethanol, and one or more contaminants.

3. The process of claim 1, wherein the fermentation off-gas of (a) comprises one or more incondensable gases, water, ethanol, and the one or more low boiling compounds.

4. The process of claim 1, wherein the process comprises recycling a gas stream output from the first separation unit by passing the gas stream output through steps (a) and (b).

5. The process of claim 1, wherein the second separation unit of (c) removes a bottom output stream comprising primarily water and a side output stream comprising fusel oil.

6. The process of claim 5, further comprising:

recycling the bottom output stream of (c) to an upstream fermentation process which produces the fermentation broth;

recycling the bottom output stream of (c) by passing the bottom output stream through step (c); or recycling the bottom output stream of (c) by passing the bottom output stream through steps (b) and (c).

7. The process of claim 1, wherein the process comprises removing a top vapor stream from the second separation unit of (c) and recycling the top vapor stream by combining the top vapor stream with the fermentation off-gas and passing the combined stream through steps (a), (b), and (c).

8. The process of claim 1, further comprising recycling water removed by the dewatering unit of (d) by passing the removed water through steps (c) and (d).

9. The process of claim 1, wherein the process comprises removing a top vapor stream from the dewatering unit of (d) and recycling the top vapor stream by combining the top vapor stream with the fermentation off-gas and passing the combined stream through steps (a), (b), (c), and (d).

10. The process of claim 1, wherein the fermentation broth comprises C4 alcohols in an amount of ≤0.5 wt. % relative to ethanol and the one or more low boiling compounds, and the C4 alcohol is 1-butanol, 2-butanol, or a combination thereof.

11. The process of claim 1, wherein the low boiling compound is acetone and the one or more operational units of (e) is a pervaporation system, a single distillation column, a sequence of distillation columns, a vacuum column, or a combination thereof, which separates the ethanol from the acetone.

12. The process of claim 1, wherein the low boiling compounds are acetone and 1-propanol and the one or more operational units of (e) are:

(i) a first distillation system which separates 1-propanol from a mixture comprising ethanol and acetone, (ii) a second distillation system which purifies the 1-propanol from (i) to a desired purity, and (ii) a third distillation system which separates the mixture of (i) into ethanol and acetone to a desired purity.

13. The process of claim 1, wherein the low boiling compounds are 1-propanol and 2-propanol and the one or more operational units of (e) are:

(i) one or more distillation columns which separate 1-propanol from a mixture comprising ethanol and 2-propanol, (ii) an extractive distillation unit which uses a solvent to extract 2-propanol from a vapor phase mixture comprising ethanol and 2-propanol while obtaining a first fraction of ethanol at a desired purity and a second fraction comprising solvent, 2-propanol, and ethanol, (iii) one or more distillation columns which separate the second fraction of (ii) into solvent and a mixture of ethanol and 2-propanol, and (iv) one or more distillation columns which separate 2-propanol at a desired purity from the mixture of (iii), leaving a solution of primarily ethanol with 2-propanol, wherein the operational units (ii) to (iv) can be replaced with a system comprising two distillation columns operating under vacuum conditions.

14. The process of claim 13, further comprising recycling the solvent of (iii) for use in the extractive distillation unit of (ii).

15. The process of claim 13, further comprising:

recycling the solution of (iv) by heating the solution to form a vapor and passing the vapor through the extractive distillation unit of (ii); or recycling the solution of (iv) by passing the solution through the extractive distillation unit of (ii).

16. The process of claim 1, wherein the low boiling compound is 2-propanol and the one or more operational units of (e) comprise:

(i) an extractive distillation unit which uses a solvent to extract 2-propanol from a vapor phase mixture comprising ethanol and 2-propanol while obtaining a first fraction of ethanol at a desired purity and a second fraction comprising solvent, 2-propanol, and ethanol, (ii) one or more distillation columns which separate the second fraction of (i) into solvent and a mixture of ethanol and 2-propanol, and (iii) one or more distillation columns which separate 2-propanol at a desired purity from the mixture of (ii), leaving a solution of primarily ethanol with 2-propanol, wherein the operational units (i) to (iii) can be replaced with a system comprising two distillation columns operating under vacuum conditions.

17. The process of claim 16, further comprising recycling the solvent of (ii) for use in the extractive distillation unit of (i).

18. The process of claim 16, further comprising:

recycling the solution of (iii) by heating the solution to form a vapor and passing the vapor through the extractive distillation unit of (i); or recycling the solution of (iii) by passing the solution through the extractive distillation unit of (i).

19. The process of claim 1, wherein the fermentation broth is obtained by a process comprising:

contacting a fermentable carbon source with an ethanol-producing yeast in a fermentation medium; and fermenting the carbon source by the yeast in the fermentation medium, to produce a fermentation broth and a fermentation off-gas comprising ethanol and the one or more low boiling compounds.

20. A process for the production and isolation of ethanol and one or more low boiling compounds, the process comprising:

(a) contacting a fermentable carbon source with an ethanol-producing yeast in a fermentation medium;

(b) fermenting the carbon source by the yeast in the fermentation medium of (a) to produce a fermentation broth and a fermentation off-gas comprising ethanol and the one or more low boiling compounds;

(c) flowing the fermentation off-gas coming from one or more fermenters in (b) through a product recovery unit wherein the flow of the off-gas is counter to a solvent flowing through the product recovery unit and obtaining a solvent stream comprising the one or more low boiling compounds and ethanol;

(d) mixing the solvent stream of (c) with the fermentation broth and passing the resulting fermentation mixture through a first separation unit to form a high water content stream comprising about 30-90% w/w water, ethanol, and the one or more low boiling compounds;

(e) passing the high water content stream of (d) through a second separation unit to form an intermediate water content stream comprising water, ethanol, and the one or more low boiling compounds;

(f) passing the intermediate water content stream of (e) through a dewatering unit to form a low water content stream comprising ≤2.5% w/w water; and (g) passing the low water content stream of (f) through one or more operational units, separating the ethanol and the one or more low boiling compounds;

wherein the process further comprises recycling a gas stream output from at least one of the first separation unit, the second separation unit, or the dewatering unit to the product recovery unit.

*     *     *     *     *